(12) United States Patent
Gaweco et al.

(10) Patent No.: US 9,133,164 B2
(45) Date of Patent: *Sep. 15, 2015

(54) MIF INHIBITORS AND THEIR USES

(75) Inventors: Anderson Gaweco, Brooklyn, NY (US); John Walker, St. Charles, MO (US); Joseph B. Monahan, St. Louis, MO (US); Jerry W. Cubbage, Wildwood, MO (US); Jeffery Carroll, St. Louis, MO (US)

(73) Assignee: INNOV88 LLC, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/237,136

(22) PCT Filed: Apr. 13, 2012

(86) PCT No.: PCT/US2012/033640
§ 371 (c)(1),
(2), (4) Date: Nov. 7, 2014

(87) PCT Pub. No.: WO2012/142498
PCT Pub. Date: Oct. 18, 2012

(65) Prior Publication Data
US 2015/0065480 A1    Mar. 5, 2015

Related U.S. Application Data

(60) Provisional application No. 61/474,975, filed on Apr. 13, 2011.

(51) Int. Cl.
| | | |
|---|---|---|
| *C07D 215/227* | (2006.01) | |
| *C07D 401/12* | (2006.01) | |
| *C07D 215/56* | (2006.01) | |
| *C07D 295/185* | (2006.01) | |
| *C07D 401/04* | (2006.01) | |
| *C07D 401/14* | (2006.01) | |
| *C07D 409/14* | (2006.01) | |
| *C07D 205/04* | (2006.01) | |

(52) U.S. Cl.
CPC ............ *C07D 401/12* (2013.01); *C07D 215/56* (2013.01); *C07D 295/185* (2013.01); *C07D 401/04* (2013.01); *C07D 401/14* (2013.01); *C07D 409/14* (2013.01); *C07D 205/04* (2013.01); *C07D 215/227* (2013.01)

(58) Field of Classification Search
CPC ............ C07D 215/227; C07D 215/38; C07D 215/58; C07D 205/04; C07D 409/14; C07D 401/14
See application file for complete search history.

(56) References Cited

U.S. PATENT DOCUMENTS

| | | | |
|---|---|---|---|
| 7,173,036 B2 * | 2/2007 | Sircar et al. ............... | 514/253.07 |
| 7,235,546 B2 * | 6/2007 | Sircar et al. ............... | 514/218 |
| 7,312,220 B2 * | 12/2007 | Sircar et al. ............... | 514/253.07 |
| 7,312,221 B2 * | 12/2007 | Sircar et al. ............... | 514/253.07 |
| 2012/0035150 A1 * | 2/2012 | Gaweco et al. .......... | 514/210.18 |

FOREIGN PATENT DOCUMENTS

| | | | |
|---|---|---|---|
| WO | 2004/074218 | * | 9/2004 |
| WO | 2005/021546 | * | 3/2005 |

OTHER PUBLICATIONS

Mekheimer, CA151:221083, abstract only of J CHem Res, vol. 12, p. 735-737, 2008.*

* cited by examiner

*Primary Examiner* — D M Seaman

(57) ABSTRACT

The invention relates to MIF inhibitors; compositions comprising an effective amount of a MIF inhibitor; and methods for treating or preventing diseases associated with MIF.

14 Claims, 1 Drawing Sheet

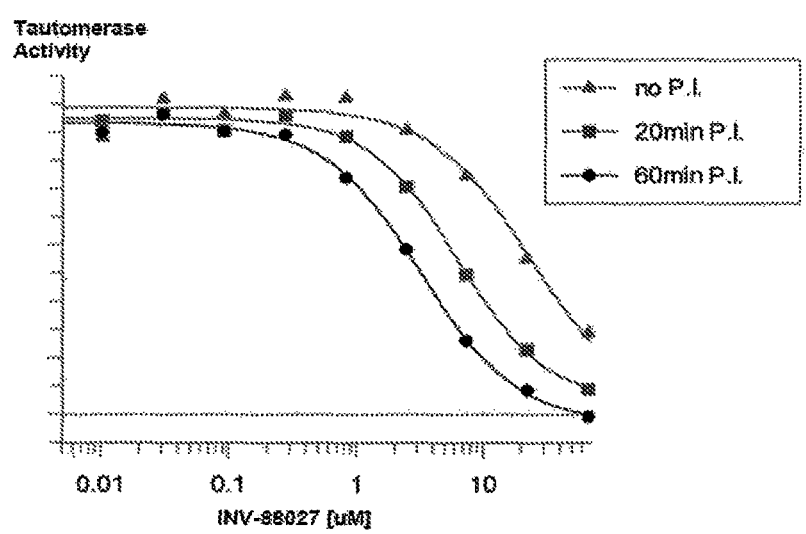

MIF INHIBITORS AND THEIR USES

FIELD OF THE INVENTION

The invention relates to Macrophage Migration Inhibitory Factor (MIF) associated diseases and disorders. More particularly, the invention relates to MIF inhibitors; compositions comprising an effective amount of a MIF inhibitor; and methods for treating or preventing MIF associated diseases and disorders.

BACKGROUND OF THE INVENTION

There are high unmet medical needs in the few established therapies for several cardiovascular and cerebrovascular diseases, autoimmune diseases and inflammatory disorders, fibrotic diseases, metabolic diseases, and oncologic diseases. Despite the diverse clinical manifestations of these diseases, they share a unique common disease pathogenesis characterized by organ and tissue damage arising from dysregulated immune responses and production of critical inflammatory mediators. Only recently has the overlapping mechanistic role of MIF been well-characterized and target validated in several animal models of some of these diseases.

MIF is a pro-inflammatory cytokine secreted by activated. T cells and macrophages that critically regulates inflammation. MIF plays an important role in the host innate and adaptive immune responses through its direct biological function and also through downstream signaling events following its binding with its known receptors CD74, CXCR2, and CXCR4. MIF is an important mediator in the initiation and perpetuation of the inflammatory process through T-cell proliferation, B-cell antibody production, macrophage activation and induction of inflammatory mediators, as well as cell growth promotion, angiogenesis and counter-regulation of glucocorticoids contributing to disease progression. MIF has been implicated in the pathogenesis of a wide range of disorders including cardiovascular and cerebrovascular diseases, autoimmune and inflammatory diseases, fibrotic diseases, metabolic diseases, and oncologic diseases. Thus MIF is a therapeutic target for many diseases and disorders.

Among cytokines, MIF is unique because it functions as an enzyme exhibiting tautomerase catalytic activity which was initially thought to underlie MIF's biologic function. The tautomerase enzyme catalytic activity site is located within the canonical deep pocket of MIF. As such, most first generation MIF inhibitors selectively target this MIF catalytic activity site. It has recently been demonstrated that inhibition of MIF tautomerase activity is not tantamount to complete inhibition of MIF biological properties In particular, a tautomerase-null, Pro to Gly1 MIF protein (P1G-MIF) knock-in mouse model showed that intrinsic tautomerase enzyme activity is dispensable for MIF's biological properties. Catalytically inactive P1G-MIF shows preservation, albeit attenuated, of MIF biological functions and of CD74- and CXCR2- binding, supporting the important role for other specific residues and motifs in MIF within and outside the catalytic site that regulates function and receptor interactions.

Recent advances in the structural biology and chemistry of MIF have revealed critical pharmacophores in addition to those in the MIF tautomerase catalytic site that should serve as important targets for the development of MIF inhibitors which display better target binding specificity and enhanced therapeutic efficacy against MIF-related diseases. For example, a new allosteric surface binding pocket has been discovered at the mouth of the canonical deep pocket catalytic site that contains specific residues important for MIF conformational changes and receptor binding. These specific MIF residues within the canonical deep pocket and the surface allosteric binding site of MIF have been identified to be important contact sites for CD74 and CXCR2 receptor binding which mediate critical MIF signal transduction activity.

Recent advances in understanding the complex biology of MIF have demonstrated MIF functioning not only through interaction with CD74, but also through CXCR2 and CXCR4 receptors. Furthermore, specific residues on MIF have been described as critical for interaction with CD74, CXCR2, and CXCR4 receptors and these have not been specifically targeted by first generation MIF tautomerase inhibitors. Lack of inhibition by these first generation MIF inhibitors of MIF/receptor binding and thus numerous MIF-induced downstream signal transduction events have limited their therapeutic potential in MIF-related diseases. Most of the first generation. MIF inhibitors do not reflect the scientific developments on MIF biology and chemistry which have recently emerged. These first generation MIF inhibitors mostly targeted the MIF enzymatic tautomerase activity located at the canonical deep pocket site around the N-terminal Pro-1 region and do not target either the surface allosteric site or the specific MIF residues within both binding sites critical for receptor interactions. Such a catalytic site-specific approach utilized by the first generation MIF inhibitors may be the reason that certain MIF biological functions and MIF-mediated signal transduction events remain partially uninhibited in the presence of these inhibitors due to insufficient conformational change of MIF and incomplete inhibition of MIF: receptor binding. In contrast, inhibitors which interact with a combination of allosteric and catalytic sites may induce a conformational change and block both tautomerase activity and critical MIF:receptor interactions resulting in effective functional antagonism and blockade of downstream, signaling.

Thus, new inhibitors of MIF are currently needed for use in treating MIF associated diseases and disorders.

SUMMARY OF THE INVENTION

The invention is based in part on the discovery of MIF inhibitors which interact with multiple binding sites on MIF and thereby inhibit interaction of MIF with its biological targets through both reversible and/or covalent binding to MIF. The invention is also based on compositions comprising an effective amount of a MIF inhibitor; and methods for treating or preventing disorders associated with high MIF expression and/or activity, comprising the administration of an effective amount of a MIF inhibitor.

In one aspect, compounds are described which inhibit the binding of MIF to CD74, CXCR2, and/or CXCR4 receptors. These compounds comprise two regions, A and B, linked by a chemical tether, with the A region binding to the allosteric surface binding pocket site and the B region binding to the canonical deep pocket tautomerase catalytic site The A region interacts with Tyr36, Trp108, Phe113, and/or other residues of MIF. Thus A is a substituent capable of pi stacking with Tyr36 causing a rotational displacement of this residue which is critical for effective receptor binding. The B region interacts with a combination of Pro1, Tyr95, Ile64 and/or other residues in the MIF catalytic site through hydrophobic interactions, hydrogen and/or covalent bonding. The tether between the A and B regions of the compound must be of appropriate length and flexibility to allow optimal association with the residues mentioned above while at the same time being rigid enough to maintain conformational integrity needed for initial interaction with the two receptor binding sites. Furthermore the tether is able to form a hydrophobic interaction with Asn97 in the catalytic pocket.

In another aspect, compounds of the Formula I are described:

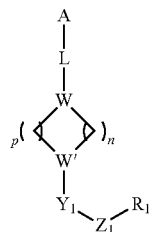

and pharmaceutically acceptable salts, hydrates, solvates, prodrugs, and tautomers thereof;
wherein A is a monocyclic or bicyclic aryl or a monocyclic or bicyclic heteroaryl;

L is a bond, —$CH_2$—, —$NR_2$—, S, or O;

each n and p is independently 1, 2, or 3;

each W and W' is independently N or CH;

$Y_1$ is null, a bond, —C(O)—, —$CH_2$—, —$SO_2$—, —S(O)— or —$NR_2$—;

$Z_1$ is a bond, —C(O)—, —$CH_2$—, —N($R_3$)($R_4$)—, —$SO_2$—, —O—, —S—, or —S(O)—;

$R_1$ is null, a substituted straight chain or branched $C_1$-$C_6$ alkyl, a straight chain or branched $C_2$-$C_6$ alkene, a straight chain or branched $C_2$-$C_6$ alkyne, a $C_3$-$C_4$ cyclic alkyl, CN, —S($O_2$)—, a —C(O)—$C_1$-$C_3$ alkyl, a C(O)—$C_2$-$C_3$ alkene, aromatic or nonaromatic monocyclic carbocycle, or aromatic or nonaromatic monocyclic heterocycle, wherein $R_1$ is optionally substituted;

$R_2$ is H, —$C_1$-$C_6$ alkyl, —$C_2$-$C_6$ alkene, —C(O)($C_1$-$C_6$ alkyl), —C(O)NH($C_1$-$C_6$ alkyl), —($C_0$-$C_3$)—($C_3$-$C_6$)cycloalkyl, or benzyl, wherein $R_2$ is optionally substituted;

$R_3$ and $R_4$ are each independently null, H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, a C(O)—$C_2$-$C_3$ alkene, or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, A is selected from indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazoppidinyl, dihydropurinonyl, pyrrolopyrimidinyl, purinyl, pyrazolopyridinyl, pyrazolopyrimidinyl, phthalimidyl, phthalitnidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, benzisobiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl. In some embodiments, A can be optionally substituted.

In other embodiments, A is selected from the group consisting of

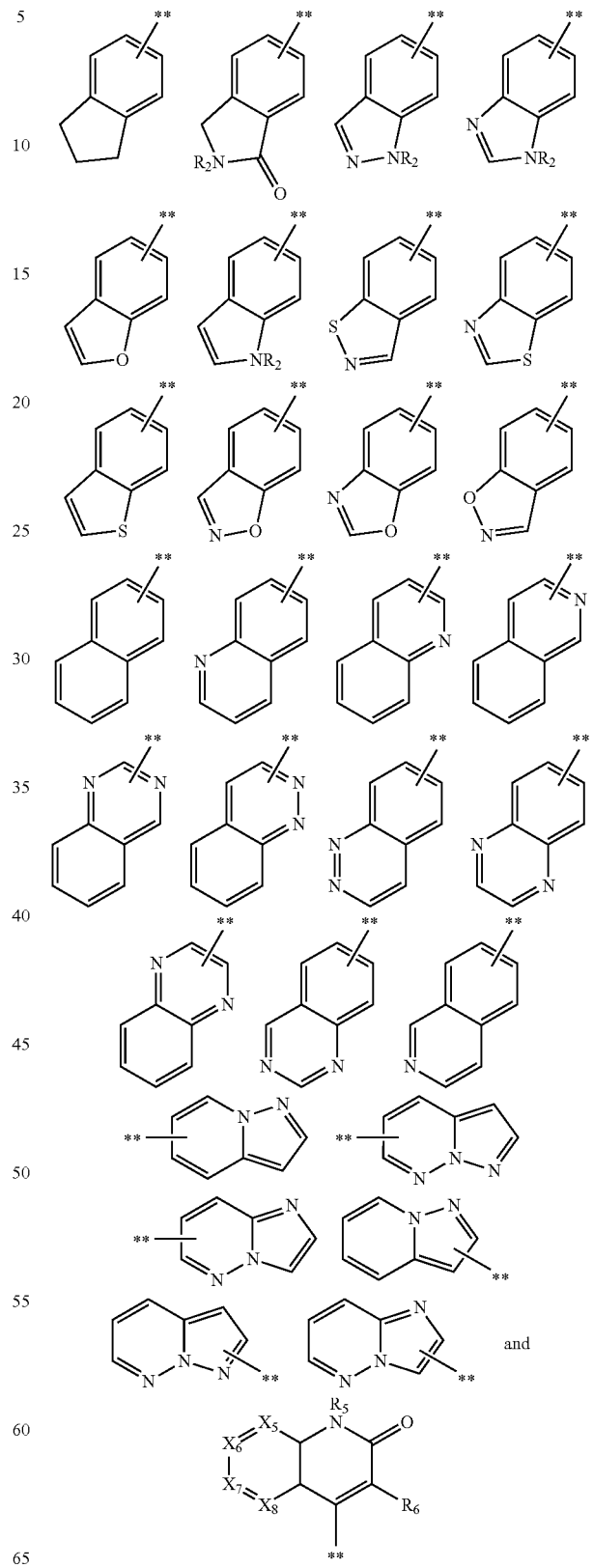

wherein

** is the site of attachment to L;

each of $X_5$, $X_6$, $X_7$, and $X_8$ is independently $CR_7$ or N;

$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is an electron withdrawing group;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl; and A is optionally substituted.

In still other embodiments, A is selected from the group consisting of

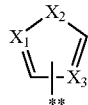 and 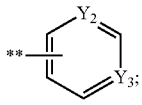

and wherein each of $X_1$, $X_2$, and $X_3$ is independently CH, O, S or $NR_2$;

each of $Y_2$ and $Y_3$ is independently CH or N; and

A is optionally substituted.

In some embodiments, $R_1$ is selected from the group consisting of straight chain or branched $C_1$-$C_6$ alkyl, straight chain or branched $C_2$-$C_6$ alkene,

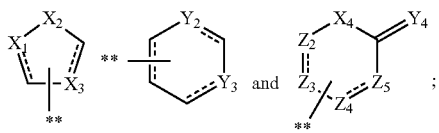

wherein each ------- represents a single or double bond;

each of $X_1$ and $X_3$ is independently CH, O, S, or $NR_2$; provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_{45}$ and $Z_5$ are attached to a single bond, then each of $Z_2$, $Z_3$, $Z_4$, and $Z_5$ is independently $CH_2$, or $NR_2$;

and $R_1$ is optionally substituted.

In certain embodiments, A is

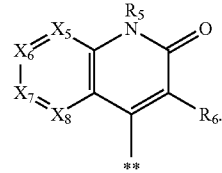

In a particular embodiment, each of $X_5$, $X_6$, $X_7$, and $X_8$ is CH; and $R_6$ is selected from —CN, —$NO_2$, —$CO_2$H, C(O)—Rx; —$CO_2$Rx; and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In other embodiments, $R_1$ is

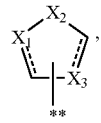

$X_1$ and $X_3$ are each CH; and each ------- represents a double bond.

In some embodiments, $R_1$ is

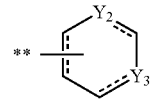

and $Y_3$ is CH and each ------- represents a double bond.

In some embodiments, n is 2 and p is 2.

In some embodiments, W is N and W' is CH.

In some embodiments, n is 1 and p is 1.

In some embodiments, when L is a bond and p and n are each 2 then W and W' can not simultaneously both be N.

In some embodiments, W is CH and W' is N.

In some embodiments, W and W' are each CH.

In some embodiments, $Y_1$ is a bond and Z is —C(O)—.

In some embodiments, L is a bond.

In some embodiments, L is $NR_2$ and $R_2$ is selected from —$C_1$-$C_6$ alkyl, benzyl, and —($C_0$-$C_3$)—($C_3$-$C_6$ cycloalkyl), and $R_2$ is optionally substituted.

In some embodiments, $R_2$ is -cyclopropylmethyl, -benzyl or —$CH_2CH_2OH$.

In some embodiments, $R_2$ is selected from H or methyl.

In some embodiments, $R_6$ is —CN.

In some embodiments, $R_5$ is $C_1$-$C_6$ alkyl.

In some embodiments, $R_5$ is $CH_3$.

In some embodiments, $R_5$ is benzyl.

In another aspect, compounds of Formula II are described:

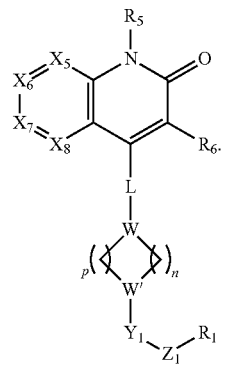

II and pharmaceutically acceptable salts, hydrates, solvates, prodrugs, and tautomers thereof;

wherein each of $X_5$, $X_6$, $X_7$, and $X_8$ is independently $CR_7$ or N;

L is a bond, —$CH_2$—, —$NR_2$—, S, or O;

each n and p is independently 1, 2, or 3;

each W and W' is independently N or CH;

$Y_1$ is null, a bond, —C(O)—, —$CH_2$—, —SO—, —$SO_2$—, or $NR_2$—;

$Z_1$ is a bond, —C(O)—, —N($R_3$)($R_4$)—, —$SO_2$—, —O—, —S—, or —S(O)—;

$R_1$ is null, a substituted straight chain or branched $C_1$-$C_6$ alkyl, a straight chain or branched $C_2$-$C_6$ alkene, a straight chain or branched $C_2$-$C_6$ alkyne, a $C_3$-$C_4$ cyclic alkyl, CN, a —C(O)—$C_1$-$C_3$ alkyl, a C(O)—$C_2$-$C_3$ alkene, an aromatic or nonaromatic monocyclic carbocycle, or aromatic or nonaromatic monocyclic heterocycle, wherein $R_1$ is optionally substituted;

$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;

$R_3$ and $R_4$ are each independently null, H, —$C_1$-$C_6$ alkyl, —($C_0$-$C_6$ alkyl)aryl, —$C_3$-$C_6$(cycloalkyl), a —C(O)—$C_1$-$C_3$ alkyl, a C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is an electron withdrawing group; and $R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl.

In some embodiments, $R_1$ is selected from the group consisting of straight chain or branched $C_1$-$C_6$ alkyl, straight chain or branched $C_2$-$C_6$ alkene,

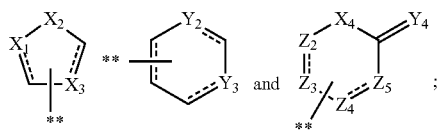

wherein each ------- represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$;

and $R_1$ is optionally substituted.

In some embodiments, $R_1$ is

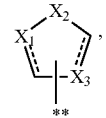

$X_1$ and $X_3$ are each CH; and each ------- represents a double bond.

In some embodiments, $R_1$ is

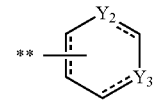

and $Y_3$ is CH and each ------- represents a double bond.

In some embodiments, $R_6$ is selected from the group consisting of —CN, —$NO_2$, —$CO_2$H, C(O)—Rx; —$CO_2$Rx; and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, p is 2 and n is 2.

In some embodiments, p is 1 and n is 1.

In some embodiments, n is 3.

In some embodiments, L is a bond or $NR_2$ and $R_2$ is H or $CH_3$.

In some embodiments, when L is a bond and p and n are each 2 then W and W' can not simultaneously both be N In another aspect, compounds of Formula IIa are described:

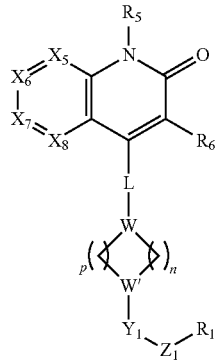

and pharmaceutically acceptable salts, hydrates, solvates, prodrugs, and tautomers thereof;
wherein
each of $X_5$, $X_6$, $X_7$, and $X_8$ is independently $CR_7$ or N;
L is a bond, —$CH_2$—, —$NR_2$—, S, or O;
each n and p is independently 1, 2, or 3;
each W and W' is independently N or CH;
$Y_1$ is null, a bond, —C(O)—, —$CH_2$—, or —$NR_2$—;
$Z_1$ is a bond, —C(O)—, —$CH_2$—, —$N(R_3)(R_4)$—, —$SO_2$—, —O—, —S—, or —S(O)—;
R is -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle, wherein $R_1$ is optionally substituted;
$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;
$R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_5$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is an electron withdrawing group; and
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl, and
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.
In some embodiments, $R_1$ is selected from -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle or,

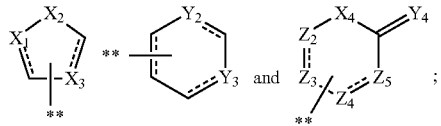

wherein
each ------ represents a single or double bond;
each of $X_1$ and $X_3$ is independently CH, O, S, $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$;
and
$R_1$ is optionally substituted.
In some embodiments, $R_1$ is

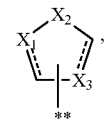

$X_1$ and $X_3$ are each CH; and
each ------ represents a double bond.
In some embodiments, $R_1$ is

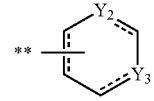

and $Y_3$ is CH and
each ------ represents a double bond.
In some embodiments, $R_6$ is selected from the group consisting of —CN, —$NO_2$, —$CO_2H$, C(O)—Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.
In some embodiments, when L is a bond and p and n are each 2 then W and W' can not simultaneously both be N In another aspect, compounds of Formula III are described:

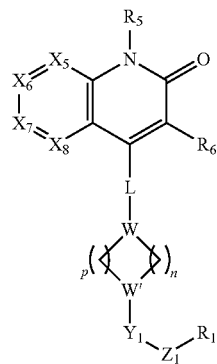

and pharmaceutically acceptable salts, hydrates, solvates, prodrugs, and tautomers thereof;
wherein
- each of $X_5$, $X_6$, $X_7$, and $X_8$ is independently CRS or N;
- L is a bond, —$CH_2$—, —$NR_2$—, S, or O;
- each W and W' is independently N or CH;
- each n and p is independently 1, 2, or 3;
- $Y_1$ is null, a bond, —C(O)—, —$CH_2$—, —SO—, —$SO_2$—, or —$NR_2$—;
- $Z_1$ is a bond, —C(O)—, —$CH_2$—, —N($R_3(R_4)$)—, —O—, —S—, —$SO_2$—, or —S(O)—;
- $R_1$ is -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle, or

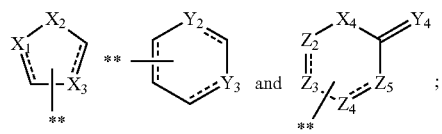

wherein
- each ------- represents a single or double bond;
- each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
- $X_2$ is $CH_2$, O, S, or $NR_2$;
- $X_4$ is $NR_2$, $CH_2$, or O;
- each of $Y_2$ and $Y_3$ is CH or N; provided that when $Y_2$ or $Y_3$ are attached to a single bond, then each of $Y_2$ and $Y_3$ is independently $CH_2$, or $NR_2$;
- $Y_4$ is O or S;
- each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
- $R_1$ is optionally substituted;
- $R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;
- $R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;
- $R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
- $R_6$ is an electron withdrawing group; and
- $R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl, and
- $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, $R_1$ is

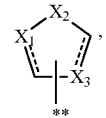

$X_1$ and $X_3$ are each CH; and
each ------- represents a double bond.

In some embodiments, $R_1$ is

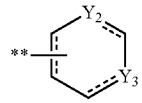

and $Y_3$ is CH and
each ------- represents a double bond.

In some embodiments, $R_6$ is selected from the group consisting of —CN, —$NO_2$, —$CO_2H$, C(O)—Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, p is 2 and n is 2.

In some embodiments, p is 1 and n is 1.

In some embodiments; n is 3.

In some embodiments, L is a bond or $NR_2$ and $R_2$ is H or $CH_3$.

In some embodiments, when L is a bond and p and n are each 2 then W and W' can not simultaneously both be N.

In another aspect, compounds of Formula IIIa are described:

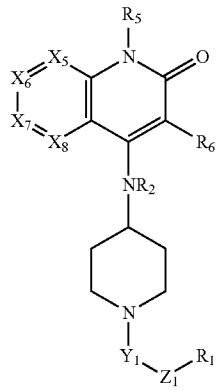

and pharmaceutically acceptable salts, hydrates, solvates, prodrugs, and tautomers thereof;
wherein
each of $X_5$, $X_6$, $X_7$, and $X_8$ is independently $CR_7$ or N;
$Y_1$ is a bond, —C(O)—, —CH$_2$—, or O;
$Z_1$ is a bond, —C(O)—, —N(R$_3$)(R$_4$)—, —SO$_2$—, or —S(O)—;
$R_1$ is -halogen, —C$_1$-C$_6$ alkyl, —C$_2$-C$_6$ alkene, —C$_2$-C$_6$ alkyne, —C$_3$-C$_4$ cycloalkyl, —CN, a —C(O)—C$_1$-C$_3$ alkyl, an aromatic or nonaromatic monocyclic carbocycle, or aromatic or nonaromatic monocyclic heterocycle, or

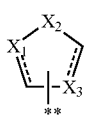 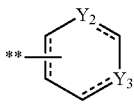 and 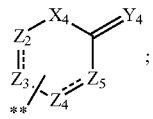 ;

wherein
each ------ represents a single or double bond;
each of $X_1$ and $X_3$ is independently CH, O, S, or NR$_2$, provided that when $X_1$ or $X_3$ are attached to a single bond, then each of $X_1$ and $X_3$ is independently CH$_2$, O, S, or NR$_2$;
$X_2$ is CH$_2$, O, S, or NR$_2$;
$X_4$ is NR$_2$, CH$_2$, or O;
each of $Y_2$ and $Y_3$ is CH or N; provided that when $Y_2$ or $Y_3$ are attached to a single bond, then each of $Y_2$ and $Y_3$ is independently CH$_2$, or NR$_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently CH$_2$, or NR$_2$; and
$R_1$ is optionally substituted;
$R_2$ is H, —C$_1$-C$_6$ alkyl, —C$_2$-C$_6$alkene, —(C$_1$-C$_3$ alkyl)-(C$_3$-C$_6$ cycloalkyl), —C(O)C$_1$-C$_6$ alkyl, —C(O)NH(C$_1$-C$_6$ alkyl), or benzyl; and wherein $R_2$ is optionally substituted;
$R_3$ and $R_4$ are each independently —H, —C$_1$-C$_6$ alkyl, —(C$_1$-C$_6$ alkyl)aryl, aryl, —C$_3$-C$_6$(cycloalkyl), —C(O)—C$_1$-C$_3$ alkyl, —C(O)—C$_1$-C$_3$; or R$_3$ and R$_4$, when taken together with the nitrogen to which they are attached, can form a heterocycle containing from one to three heteroatoms selected from N, O, and S, and wherein $R_3$ and $R_4$ are optionally substituted;
$R_5$ is H, —C$_1$-C$_6$ alkyl, —C$_2$-C$_6$ alkene, —(C$_0$-C$_3$ alkyl)-(C$_3$-C$_6$)cycloalkyl, —(C$_2$-C$_6$alkyl)-O—(C$_1$-C$_3$ alkyl), —(C$_2$-C$_6$ alkyl)-O—(C$_3$-C$_6$)cycloalkyl, —(C$_2$-C$_6$alkyl)-O-aryl, —(C$_2$-C$_6$ alkyl)-O-heteroaryl, —(C$_2$-C$_6$alkyl)-NR$_8$R$_9$, —(C$_1$-C$_3$ alkyl)heteroaryl or —(C$_1$-C$_3$ alkyl)aryl, wherein $R_5$ is optionally substituted;
$R_6$ is an electron withdrawing group; and
$R_7$ is H, F, Cl, —CF$_3$, —CN, —CO$_2$-alkyl, —C$_1$-C$_6$ alkyl, —C$_3$-C$_7$(cycloalkyl), —O—(C$_1$-C$_6$ alkyl), —OCF$_3$, —SO$_2$NH$_2$, SO$_2$-alkyl,
$R_8$ and $R_9$ are each independently H, —C$_1$-C$_6$ alkyl, —(C$_0$-C$_6$ alkyl)aryl, C$_0$-C$_3$ alkyl)-C$_3$-C$_6$(cycloalkyl), —C(O)—C$_1$-C$_3$ alkyl, —C(O)—C$_2$-C$_3$ alkene; or R$_3$ and R$_4$, when taken together with the nitrogen to which they are attached, can form a heterocycle containing from one to three heteroatoms selected from N, O, and S, and wherein $R_3$ and $R_4$ are optionally substituted,
In some embodiments, $R_1$ is

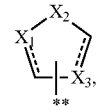

$X_1$ and $X_3$ are each CH; and
each ------ represents a double bond.
In some embodiments, $R_1$ is

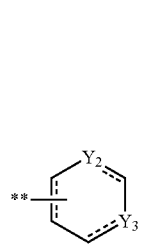

and $Y_3$ is CH and
each ------ represents a double bond.
In some embodiments, $R_6$ is selected from the group consisting of —CN, —NO$_2$, —CO$_2$H, C(O)—Rx; —CO$_2$Rx; and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S. In a particular embodiment, $R_6$ is —CN.
In some embodiments, $R_2$ is -cyclopropylmethyl, benzyl, or —CH$_2$CH$_2$OH;
In some embodiments, $R_2$ is H, or CH3.

In another aspect, compounds of Formula IIIb are described:

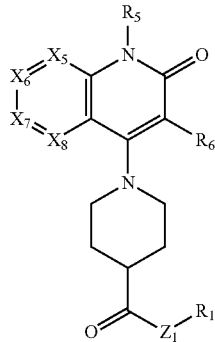

IIIb and pharmaceutically acceptable salts, hydrates, solvates, prodrugs, and tautomers thereof;
wherein
each of $X_5$, $X_6$, $X_7$, and $X_8$ is independently $CR_7$ or N;
$Z_1$ is a bond, —C(O)—, $CH_2$—, —N($R_3$)($R_4$)—, —SO$_2$—, —S—, or —O—;
$R_1$ is -halogen, —$C_1$-$C_6$ alkyl, —$C_2$-$C_6$ alkene, —$C_2$-$C_6$ alkyne, —$C_3$-$C_4$ cycloalkyl, —CN, —C(O)—$C_1$-$C_3$ alkyl, an aromatic or nonaromatic monocyclic carbocycle, or aromatic or nonaromatic monocyclic heterocycle, or

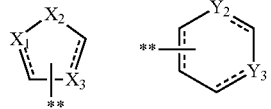 and 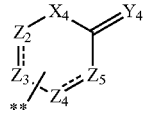;

wherein
each ------ represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
$R_1$ is optionally substituted;
$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;
$R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is an electron withdrawing group; and
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl, and
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted,
In some embodiments, $R_1$ is

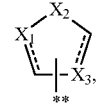

$X_1$ and $X_3$ are each CH; and
each ------ represents a double bond.
In some embodiments, $R_1$ is

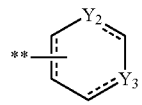

and $Y_3$ is CH and
each ------ represents a double bond.
In some embodiments, $R_6$ is selected from the group consisting of —CN, —$NO_2$, —$CO_2H$, C(O)—Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.
In some embodiments, $Z_1$ is $NR_3R_4$, $R_3$ is H and $R_4$ is null.
In some embodiments, $R_6$ is CN.
In another aspect, compounds of Formula IIIc are described:

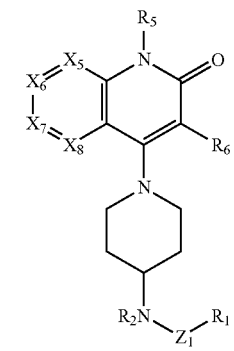

IIIc and pharmaceutically acceptable salts, hydrates, solvates, prodrugs, and tautomers thereof;

wherein
each of $X_5$, $X_6$, $X_7$, and $X_8$ is independently $CR_7$ or N;
$Z_1$ is a bond, —C(O)—, —CH$_2$—, —N(R$_3$)(R$_4$)—, —SO$_2$—, —O—, or —S—;
$R_1$ is -halogen, —C$_1$-C$_6$ alkyl, —C$_2$-C$_6$ alkene, —C$_2$-C$_6$ alkyne, —C$_3$-C$_4$ cycloalkyl, —CN, a —C(O)—C$_1$-C$_3$ alkyl, an aromatic or nonaromatic monocyclic carbocycle, or aromatic or nonaromatic monocyclic heterocycle, or

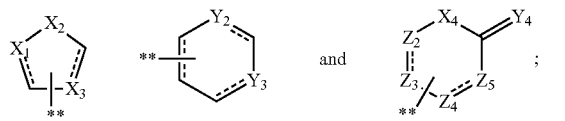

wherein
each ------ represents a single or double bond;
each of $X_1$ and $X_3$ is independently CH, O, S, or NR$_2$, provided that when $X_1$ or $X_3$ are attached to a single bond, then each of $X_1$ and $X_3$ is independently CH$_2$, O, S, or NR$_2$;
$X_2$ is CH$_2$, O, S, or NR$_2$;
$X_4$ is NR$_2$, CH$_2$, or O;
each of $Y_2$ and $Y_3$ is CH or N; provided that when $Y_2$ or $Y_3$ are attached to a single bond, then each of $Y_2$ and $Y_3$ is independently CH$_2$, or NR$_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently CH$_2$, or NR$_2$; and
$R_1$ is optionally substituted;
$R_2$ is H, —C$_1$-C$_6$ alkyl, —C$_2$-C$_6$ alkene, —(C$_1$-C$_3$ alkyl)-(C$_3$-C$_6$ cycloalkyl), —C(O)C$_1$-C$_6$ alkyl, —C(O)NH(C$_1$-C$_6$ alkyl), or benzyl; and wherein $R_2$ is optionally substituted;
$R_3$ and $R_4$ are each independently —H, —C$_1$-C$_6$ alkyl, —(C$_1$-C$_6$ alkyl)aryl, aryl, —C$_3$-C$_6$(cycloalkyl), —C(O)—C$_1$-C$_3$ alkyl, —C(O)—C$_1$-C$_3$; or $R_3$ and $R_4$, when taken together with the nitrogen to which they are attached, can form a heterocycle containing from one to three heteroatoms selected from N, O and S, and wherein $R_3$ and $R_4$ are optionally substituted;
$R_5$ is H, —C$_1$-C$_6$ alkyl, —C$_2$-C$_6$ alkene, —(C$_0$-C$_3$ alkyl)-(C$_3$-C$_6$)cycloalkyl, —(C$_2$-C$_6$ alkyl)-O—(C$_1$-C$_3$ alkyl), —(C$_2$-C$_6$ alkyl)-O—(C$_3$-C$_6$)cycloalkyl, —(C$_2$-C$_6$ alkyl)-O-aryl, —(C$_2$-C$_6$ alkyl)-O-heteroaryl, —(C$_2$-C$_6$alkyl)-NR$_8$R$_9$, —(C$_1$-C$_3$ alkyl)heteroaryl or —(C$_1$-C$_3$ alkyl)aryl, wherein $R_5$ is optionally substituted;
$R_6$ is an electron withdrawing group; and
$R_7$ is H, F, Cl, —CF$_3$, —CN, —CO$_2$-alkyl, —C$_1$-C$_6$ alkyl, —C$_3$-C$_7$(cycloalkyl), —O—(C$_1$-C$_6$ alkyl), —OCF$_3$, —SO$_2$NH$_2$, SO$_2$-alkyl,
$R_8$ and $R_9$ are each independently H, —C$_1$-C$_6$ alkyl, —(C$_0$-C$_6$ alkyl)aryl, C$_0$-C$_3$ alkyl)-C$_3$-C$_6$(cycloalkyl), —C(O)—C$_1$-C$_3$ alkyl, —C(O)—C$_2$-C$_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, $R_1$ is

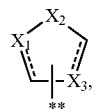

$X_1$ and $X_3$ are each CH; and
each ------ represents a double bond.

In some embodiments, $R_1$ is

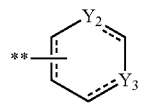

and $Y_3$ is CH and
each ------ represents a double bond.

In some embodiments, $R_6$ is selected from the group consisting of —CN, —NO$_2$, —CO$_2$H, C(O)—Rx; —CO$_2$Rx; and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S.

In some embodiments, $R_6$ is CN.

In another aspect, compounds of Formula IIId are described:

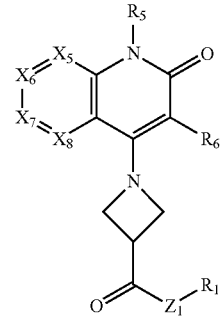

IIId and pharmaceutically acceptable salts, hydrates, solvates, prodrugs, and tautomers thereof;
wherein
each of $X_5$, $X_6$, $X_7$, and $X_8$ is independently $CR_7$ or N;
$Z_1$ is a bond, —S—, —N(R$_3$)(R$_4$);
$R_1$ is -halogen, —C$_1$-C$_6$ alkyl, —C$_2$-C$_6$ alkene, —C$_2$-C$_6$ alkyne, —C$_3$-C$_4$ cycloalkyl, —CN, a —C(O)—C$_1$-C$_3$ alkyl, an aromatic or nonaromatic monocyclic carbocycle, or aromatic or nonaromatic monocyclic heterocycle, or

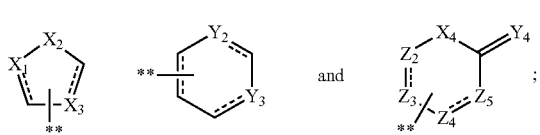

wherein
each ------ represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
$R_1$ is optionally substituted;
$R_2$ is H, —$C_1$-$C_6$ alkyl, —$C_2$-$C_6$ alkene, alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;
$R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$-($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is an electron withdrawing group; and
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl,
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted,
In some embodiments, $R_1$ is

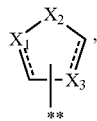

$X_1$ and $X_3$ are each CH; and
each ------ represents a double bond.
In some embodiments, $R_1$ is

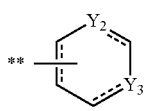

and $Y_3$ is CH and
each ------ represents a double bond.

In some embodiments, $R_6$ is selected from the group consisting of —CN, —$NO_2$, —$CO_2H$, C(O)—Rx; —$CO_2$Rx; and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, $R_6$ is CN.

In another aspect, compounds of Formula IIIe are described:

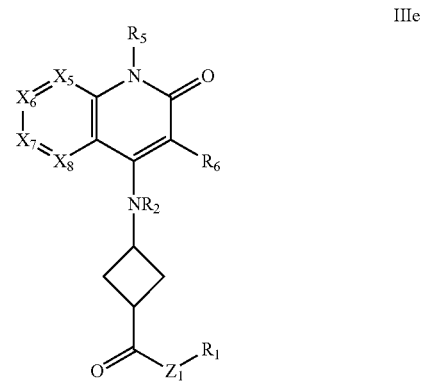

IIIe and pharmaceutically acceptable salts, hydrates, solvates, prodrugs, and tautomers thereof;
wherein
each of $X_5$, $X_6$, $X_7$, and $X_8$ is independently $CR_7$ or N;
$Z_1$ is a bond or —N($R_3$)($R_4$);
$R_1$ is -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle, or

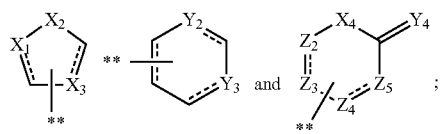

wherein
each ------ represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
$R_1$ is optionally substituted;
$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;

$R_3$ and $R_4$ are each, independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is an electron withdrawing group; and $R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl, and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, $R_1$ is

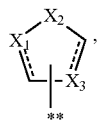

$X_1$ and $X_3$ are each CH; and
each ------- represents a double bond.

In some embodiments $R_1$ is

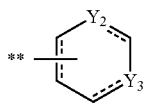

and $Y_3$ is CH and
each ------- represents a double bond.

In another aspect, compounds of Formula IIIf are described:

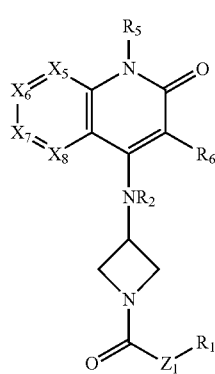

IIIf and pharmaceutically acceptable salts, hydrates, solvates, prodrugs, and tautomers thereof;

wherein each of $X_5$, $X_6$, $X_7$, and $X_8$, is independently $CR_7$ or N;

$Z_1$ is a bond or —$N(R_3)(R_4)$;

$R_1$ is -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle, or

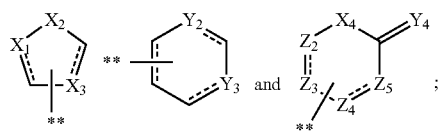

wherein each ------- represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and $R_1$ is optionally substituted;

$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;

$R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is an electron withdrawing group; and $R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl, and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, $R_1$ is $X_1$ and $X_3$ are each CH; and
each ------- represents a double bond.
In some embodiments, $R_1$ is and $Y_3$ is CH and
each ------- represents a double bond.
In another aspect, compounds of Formula IIIg are described:

IIIg and pharmaceutically acceptable salts, hydrates, solvates, prodrugs, and tautomers thereof;
wherein
each of $X_5$, $X_6$, $X_7$, and $X_8$ is independently $CR_7$ or N;
$Z_1$ is a bond or —$N(R_3)(R_4)$;
$R_1$ is -halogen, —$C_1$-$C_6$ alkyl, —$C_2$-$C_6$ alkene, —$C_2$-$C_6$ alkyne, —$C_3$-$C_4$ cycloalkyl, —CN, a —C(O)—$C_1$-$C_3$ alkyl, an aromatic or nonaromatic monocyclic carbocycle, or aromatic or nonaromatic monocyclic heterocycle, or Wherein
each ------- represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
$R_1$ is optionally substituted;
$R_2$ is H, —$C_1$-$C_6$ alkyl, —$C_2$-$C_6$ alkene, —($C_1$-$C_3$ alkyl)-($C_3$-$C_6$ cycloalkyl), —C(O)$C_1$-$C_6$ alkyl, —C(O)NH($C_1$-$C_6$ alkyl), or benzyl; and wherein $R_2$ is optionally substituted;
$R_3$ and $R_4$ are each independently —H, —$C_1$-$C_6$ alkyl, —($C_1$-$C_6$ alkyl)aryl, aryl, —$C_3$-$C_6$(cycloalkyl), —C(O)—$C_1$-$C_3$ alkyl, —C(O)—$C_1$-$C_3$; or $R_3$ and $R_4$, when taken together with the nitrogen to which they are attached, can form a heterocycle containing from one to three heteroatoms selected from N, O, and S, and wherein $R_3$ and $R_4$ are optionally substituted;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is an electron withdrawing group; and
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$, $SO_2$-alkyl,
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_4$ are optionally substituted.
In some embodiments, $R_1$ is $X_1$ and $X_3$ are each CH; and
each ------- represents a double bond.
In some embodiments, $R_1$ is and $Y_3$ is CH and
each ------- represents a double bond.
In some embodiments, $R_6$ is selected from the group consisting of —CN, —$NO_2$, —$CO_2H$, C(O)—Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, $R_6$ is CN.

In another aspect, pharmaceutical formulations are described comprising at least one MIF inhibitor and a pharmaceutically acceptable carrier.

In another aspect, methods of treating a disease associated with high MIF expression is provided, which comprises administering to a subject in need thereof, a therapeutically-effective amount of a MIF inhibitor. In some embodiments, the disease associated with high MIF expression is selected from Cardiovascular and Cerebrovascular diseases, including but not limited to Atherosclerosis, restenosis of an atherosclerotic coronary artery, Acute coronary syndrome, myocardial infarction, cardiac-allograft vasculopathy, Stroke; Autoimmune Diseases and Inflammatory Disorders, including but not limited to Asthma, chronic obstructive pulmonary disease, Rheumatoid arthritis, Juvenile rheumatoid arthritis, neuropathic pain, Fibromyalgia, Psoriasis, Psoriatic arthritis, colitis, Crohn's disease, ulcerative colitis, Multiple sclerosis, Alzheimer's disease, autoimmune uveitis, Castleman's disease, Ankylosing spondylitis, Pemphigus, Myasthenia gravis, Guillain-Barre syndrome, hepatitis, otitis, experimental allergic neuritis, Autoimmune glomerulonephritis, organ transplant rejection, Sepsis, Shock, spondylitis, systemic lupus erythematosus, lupus nephritis, Diabetes mellitus type 1, Diabetes mellitus type 2, sclerosis, vasculitis, sarcoidosis, pulmonary inflammation, Acute respiratory distress syndrome, wet and dry age-related macular degeneration; Fibrotic diseases; Metabolic disorders, including but not limited to Obesity, steroid-resistance, glucose intolerance, metabolic syndrome; and Neoplasia, including but not limited to angiogenesis, multiple myeloma, leukemia, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast non-small cell lung carcinoma, melanoma, skin cancer, teratoma, rhabdomyosarcoma, glioma, and metastatic bone disease.

Also described are methods of inhibiting MIF binding to CD74, CXCR2, CXCR4 and/or other receptors in a subject which comprises administering to a subject in need thereof, a pharmaceutically effective amount of a MIF inhibitor. In some embodiments, the method of inhibiting MIF binding to CD74 includes preventing the interaction between MIF with CD74 alone or MIF with CD74 complexed with CD44, CXCR2, CXCR4 and/or other receptors as receptor signaling heterocomplexes.

Also described are methods of inhibiting MIF-induced activation of and signal transduction through CD74, CXCR2, CXCR4 and/or other receptors in a subject which comprises administering to a subject in need thereof a pharmaceutically effective amount of a MIF inhibitor.

Also described are methods of inhibiting the ability of MIF to form a homomultimer or trimer in a subject which comprises administering to a subject in need thereof a pharmaceutically effective amount of a MIF inhibitor.

Also described are methods of inhibiting MIF tautomerase catalytic activity in a subject which compromises administering to a subject in need thereof a pharmaceutically effective amount of a MIF inhibitor.

Also described are methods of inhibiting MIF biological function in a subject which comprises administering to a subject in need thereof a pharmaceutically effective amount of a MIF inhibitor.

Also described are methods of inhibiting MIF expression, production, and/or secretion in a subject which comprises administering to a subject in need thereof a pharmaceutically effective amount of a MIF inhibitor.

Also described are methods of inhibiting MIF-induced local or systemic inflammatory cell recruitment, infiltration, proliferation or activation; parenchymal cell damage or cellular transformation; or a combination thereof in a subject which comprises administering to a subject in need thereof a pharmaceutically effective amount of a MIF inhibitor.

Also described are methods of inhibiting MIF binding to extracellular and/or intracellular CD74, CXCR2, CXCR4 and/or other targets which comprises contacting a cell with an effective amount of a MIF inhibitor.

Also described are methods of inhibiting MIF binding to soluble receptor forms of CD74, CXCR2, CXCR4 and/or other targets with an effective amount of a MIF inhibitor.

Also described are methods of inhibiting the ability of MIF to form a homomultimer or trimer in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF biological function in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF expression, production, and/or secretion in a cell which comprises a contacting cell with a pharmaceutically effective amount of a MIF inhibitor.

Also described are methods of inhibiting MIF-induced local and/or systemic inflammatory cell recruitment, infiltration, proliferation or activation; parenchymal cell damage or cellular transformation; or a combination thereof which comprises contacting a cell with an effective amount of a MIF inhibitor.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

BRIEF DESCRIPTION OF THE DRAWINGS

FIG. 1 shows the inhibitory properties of Compound 1 on tautomerase activity.

DETAILED DESCRIPTION OF THE INVENTION

Based on emerging data, an in silico screening campaign strategy of known fragment inhibitors coupled with structure based drug design was conducted to identify lead scaffolds that would inhibit both MIF allosteric and catalytic binding sites and interfere with MIF residues important for receptor binding. Dual pocket binding inhibition is hypothesized to exhibit better potency, efficacy and safety for a competitive inhibitor that differentiates it from single-pocket binding of earlier MIF inhibitors. Multiple interaction points within the two pockets of MIF at the catalytic and allosteric binding sites are expected to enhance potency over single pocket early MIF inhibitors that may translate to more potent inhibition of MIF biological function, production, secretion and its receptor binding. The more complex binding conformation should therefore enhance selectivity resulting in a superior safety profile (lower probability of off-target toxicity) and a wider therapeutic index. Critical MIF residues reportedly important for MIF receptor binding are specifically targeted to inhibit MIF binding with CD74, CXCR2 and/or CXCR4 and downstream signaling events which should translate into improved efficacy and anti-inflammatory effects. Interaction with the newly described surface allosteric pocket in addition to the catalytic domain may more effectively disrupt MIF/receptor binding through physical perturbations and conformational disruption. Fragment-based screening coupled with structure-based drug design using scaffold replacement enabled us to develop in silico new chemical entities incorporating fragment inhibitors that directly bind and inhibit the three important MIF pharmacophore target sites in single new chemical entities. Two of the three critical pharmacophoric elements of MIF required for high-affinity binding have only recently been mapped out, thus, not targeted by earlier MIF antagonists.

Definitions

The following definitions are used in connection with the MIF inhibitors:

The term "MIF inhibitor" includes any and all possible isomers, stereoisomers, enantiomers, diastereomers, tautomers, pharmaceutically acceptable salts, hydrates, solvates, and prodrugs of the MIF inhibitors described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated: hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The terms "monocyclic or bicyclic aryl" or "monocyclic or bicyclic heteroaryl" as used herein include but are not limited to, indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, benzisobiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a MIF inhibitor and a pharmaceutically acceptable carrier. The invention includes a MIF inhibitor provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mutate; napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, salfosalicylate, suramate, tannate, tartrate, teoclate, tosylate, triethiodide, and valerate salts.

An "effective amount" when used in connection with a MIF inhibitor is an amount effective for treating or preventing a MIF-associated disease or disorder.

The term "carrier," as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating," with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer," "administering," or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a MIF inhibitor.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O, Suitable substituents are selected from the following which include, but are not limited to, hydroxyl, halogen, perfluorinated $C_3$-$C_6$ alkyl, amine, —$C_1$-$C_{12}$ alkyl, —$C_2$-$C_{12}$ alkene, —$C_2$-$C_{12}$ alkyne, —($C_1$-$C_3$ alkyl)-(cycloalkyl), aryl, alkyl-aryl, —C(O)H, —C(O)OH, —C(O)alkyl, —C(O)—O-alkyl, —C(O)NH(alkyl), benzyl, —C(O)$NH_2$, —C(O)N(alkyl)$_2$, —NHC(O)H, —NHC(O)alkyl, —$SO_2$(alkyl), —$SO_2NH_2$, —$SO_2$NH(alkyl), —$SO_2$N(alkyl)$_2$, S, CN, and SCN. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables: within any of the Formulae represented herein are permissible only if such combinations result in stable compounds or useful synthetic intermediates wherein stable implies a reasonable pharmacologically relevant half-life at physiological conditions.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, ozone is potassium peroxymonosulfate, Pd/C: is palladium on carbon, TFA is trifluoroacetic acid, TGPS is tocopherol propylene glycol succinate, and THF is tetrahydrofuran.

Compounds

Accordingly in one aspect, compounds are described that comprise two regions, A and B, linked by a chemical tether, with the A region binding to the allosteric surface binding pocket site and the B region binding to the canonical deep pocket catalytic site The A region interacts with Tyr36, Trp108 and Phe113 of MIF. Thus A is a substituent capable of pi stacking with Tyr36 causing a rotational displacement of this residue which is critical for effective receptor binding. The B region interacts with a combination of Pro1, Tyr95, Ile64 and or other residues in the MIF catalytic site through hydrophobic interactions, and hydrogen and/or covalent bonding. The tether between the A and B regions of the compound must be of appropriate length and flexibility to allow optimal association with the residues mentioned above while at the same time being rigid enough to maintain conformational integrity needed for initial interaction with the two receptor binding sites. Furthermore the tether is able to form a hydrophobic interaction with Asn97 in the catalytic pocket.

In another aspect, the present invention provides MIF inhibitors according to Formula I:

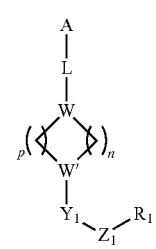

I and pharmaceutically acceptable salts, hydrates, solvates, prodrugs, and tautomers thereof;

wherein A, L, n, p, W, W', $Y_1$, $Z_1$, $R_1$, $R_2$, $R_3$, $R_4$, are as defined above for Formula I.

In some embodiments, A is an aromatic, bicyclic heterocycle.

In some embodiments, L is a bond.
In some embodiments, L is, —$CH_2$—.
In some embodiments, L is —$NR_2$—.
In some embodiments, L is S.
In some embodiments, L is O.
In some embodiments, each n and p is 1.
In some embodiments, each n and p is 2.
In some embodiments, W is N.
In some embodiments, W is CH.
In some embodiments, W' is N.
In some embodiments, W' is CH.
In some embodiments, $Y_1$ is null.
In some embodiments, $Y_1$ is a bond.
In some embodiments, $Y_1$ is, —C(O)—.
In some embodiments, $Y_1$ is —$CH_2$—.
In some embodiments, $Y_1$ is —$NR_2$—.
In some embodiments, $Y_1$ is —O—.
In some embodiments, $Z_1$ is a bond.
In some embodiments, $Z_1$ is —$CH_2$—.
In some embodiments, $Z_1$ is —C(O)—.
In some embodiments, $Z_1$ is —N($R_3$)($R_4$)—.
In some embodiments, $Z_1$ is —$SO_2$—.
In some embodiments, $Z_1$ is —O—.
In some embodiments, $Z_1$ is —S—.
In some embodiments, $Z_1$ is —S(O)—.
In some embodiments, $R_1$ is null.
In some embodiments, $R_1$ is a substituted straight chain or branched $C_1$-$C_6$ alkyl.
In some embodiments, $R_1$ is a straight chain or branched $C_2$-$C_6$ alkene.

In some embodiments, $R_1$ is a straight chain or branched $C_2$-$C_6$ alkyne.

In some embodiments, $R_1$ is a —CN.

In some embodiments, $R_1$ is a Cl.

In some embodiments, $R_1$ is a —$C_3$-$C_6$ carbacyclic ring.

$R_1$ is a saturated a 3-6 membered heterocyclic ring

In some embodiments, $R_1$ is a —C(O)—$C_2$-$C_3$ alkene.

In some embodiments, $R_1$ is aromatic or nonaromatic monocyclic carbocycle.

In some embodiments, $R_1$ is aromatic or nonaromatic monocyclic heterocycle.

In some embodiments, $R_2$ is H.

In some embodiments, $R_2$ is —$C_1$-$C_6$ alkyl.

In some embodiments, $R_2$ is —$C_2$-$C_6$ alkene.

In some embodiments, $R_2$ is —C(O)($C_1$-$C_6$ alkyl).

In some embodiments, $R_2$ is —C(O)NH($C_1$-$C_6$ alkyl).

In some embodiments, $R_2$ is —($C_0$-$C_3$)—($C_3$-$C_6$)cycloalkyl.

In some embodiments, $R_2$ is or benzyl.

In some embodiments, $R_3$ is a bond.

In some embodiments, $R_3$ is H.

In some embodiments, $R_3$ is —$C_1$-$C_6$ alkyl.

In some embodiments, $R_3$ is —($C_1$-$C_6$ alkyl)aryl.

In some embodiments, $R_3$ is aryl.

In some embodiments, $R_3$ is —$C_3$-$C_6$(cycloalkyl).

In some embodiments, $R_3$ and $R_4$, are taken together with the nitrogen to which they are attached and form a heterocycle containing two N.

In some embodiments, A is quinolinyl, isoquinolinyl, phthalazinyl, dihydroquinolinyl, tetrahydroquinolinyl, dihydroisoquinolyl, tetrahydroisoquinolinyl, quinolonyl, isoquinolonyl, or naphthyl, wherein A can be optionally substituted.

In particular embodiments, A is quinolonyl.

In some embodiments, A is pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, or triazinyl, wherein A can be optionally substituted.

In some embodiments, A is selected from the group consisting of

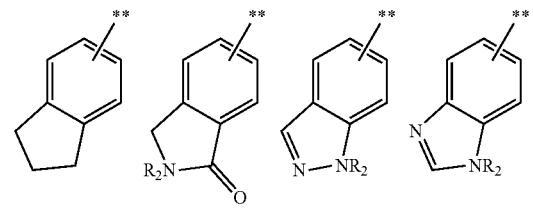

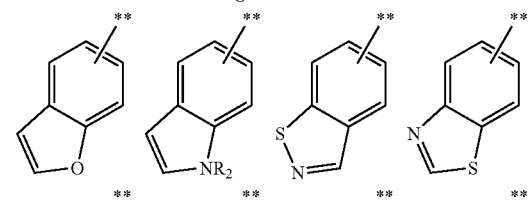

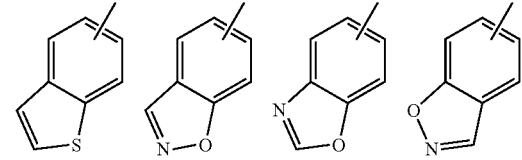

In some embodiments, A is selected from the group consisting of

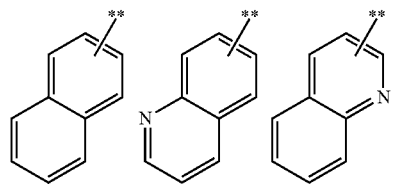

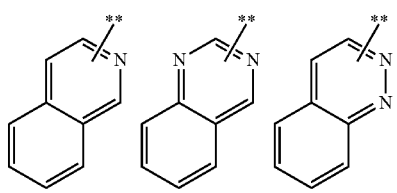

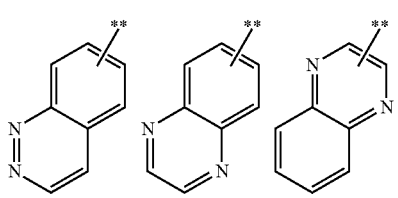

In some embodiments, A is selected from the group consisting of

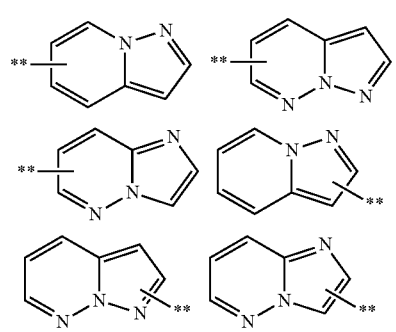

In some embodiments, A is

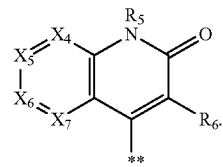

In some embodiments, A is

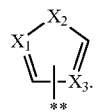

In some embodiments, A is

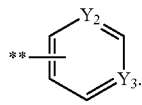

In some embodiments, $X_1$ and $X_3$ are each CH.
In some embodiments, $X_2$ is S.
In some embodiments, $X_2$ is $NR_2$,
In some embodiments, $X_2$ is O.
In some embodiments, $Y_2$ is CH.
In some embodiments, $Y_2$ is N.
In some embodiments, $R_1$ is selected from the group consisting of straight chain or branched $C_1$-$C_6$ alkyl.
In some embodiments, $R_1$ is straight chain or branched $C_2$-$C_6$ alkene.
In some embodiments, $R_1$ is

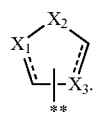

In some embodiments, $R_1$ is

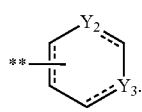

In some embodiments, $R_1$ is

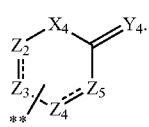

In some embodiments, $X_1$ and $X_3$ are each CH,
In some embodiments, $X_2$ is O.
In some embodiments, $X_2$ is S.
In some embodiments, $X_2$ is $NR_2$.
In some embodiments, $X_4$ is $NR_2$.
In some embodiments, $Y_2$ is CH.
In some embodiments, $Y_2$ is N.
In some embodiments, $Y_4$ is O.
In some embodiments, $Z_2$, $Z_3$, $Z_4$, and $Z_5$ are each CH.
In some embodiments, ------- represents a double bond.

In some embodiments, A is

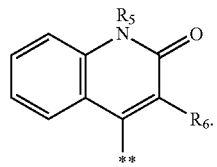

In some embodiments, A is

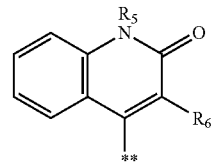

and $R_1$ is

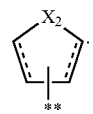

In some embodiments, A is

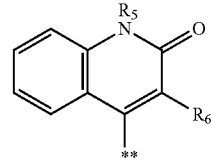

and $R_1$ is

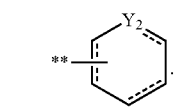

In some embodiments, n is 2 and p is 2.
In some embodiments, W is N and W' is CH.
In some embodiments, n is 1 and p is 1,
In some embodiments, W is CH and W' is N.
In some embodiments, W and W' are each CH.
In some embodiments, $Y_1$ is a bond and Z is —C(O)—.
In some embodiments, L is a bond.
In some embodiments, L is $NR_2$ and $R_2$ is selected from —$C_1$-$C_6$ alkyl, benzyl, and —($C_0$-$C_3$)—($C_3$-$C_6$ cycloalkyl), and $R_2$ is optionally substituted.
In some embodiments, $R_2$ is -cyclopropylmethyl, -benzyl or —$CH_2CH_2OH$.
In some embodiments, $R_2$ is selected from H or methyl.
In some embodiments, $R_6$ is —CN.
In some embodiments, $R_5$ is $C_1$-$C_6$ alkyl.
In some embodiments, $R_5$ is $CH_3$.
In some embodiments, $R_5$ is benzyl.

In another aspect, the present invention provides compounds of the Formula II:

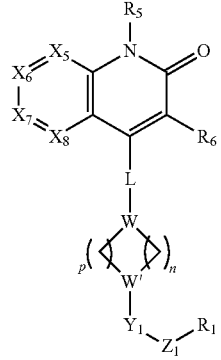

and pharmaceutically acceptable salts, hydrates, solvates, prodrugs, and tautomers thereof;
wherein
$X_5$, $X_6$, $X_7$, and $X_8$, L, n and p, W and W', $Y_1$, $Z_1$, $R_1$, $R_2$, $R_3$, $R_4$, $R_5$, $R_6$ are as defined above for Formula II.

In some embodiments, $R_1$ is selected from the group consisting of substituted straight chain or branched $C_1$-$C_6$ alknyl.

In some embodiments, $R_1$ a 3-6 membered carbacyclic ring
In some embodiments, $R_1$ is a 3-6 membered heterocyclic ring
In some embodiments, $R_1$ is —Cl
In some embodiments, $R_1$ is straight chain or branched $C_2$-$C_6$ alkene.
In some embodiments, $R_1$ is

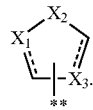

In some embodiments, $R_1$ is

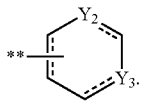

In some embodiments, $R_1$ is

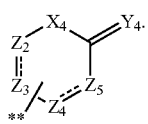

In some embodiments, $X_1$ and $X_3$ are each CH.
In some embodiments, $X_2$ is O.
In some embodiments, $X_2$ is S.
In some embodiments, $X_2$ is $NR_2$.
In some embodiments, $X_4$ is $NR_2$.
In some embodiments, $Y_2$ is CH.
In some embodiments, $Y_2$ is N.
In some embodiments, $Y_4$ is O.

In some embodiments, $Z_2$, $Z_3$, $Z_4$, and $Z_5$ are each CH.
In some embodiments, ------ represents a double bond.
In some embodiments, $R_1$ is

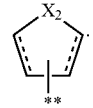

In some embodiments, $R_1$ is

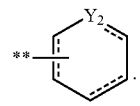

In some embodiments, $R_1$ a 3-6 membered carbacyclic ring
In some embodiments, $R_1$ is a 3-6 membered heterocyclic ring
In some embodiments, $R_1$ is a $C_2$-$C_6$ alkenyl
In some embodiments, $R_1$ is a $C_2$-$C_6$ alkynyl
In some embodiments, $R_1$ is —Cl
In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In another aspect, the present invention provides compounds of the Formula IIa:

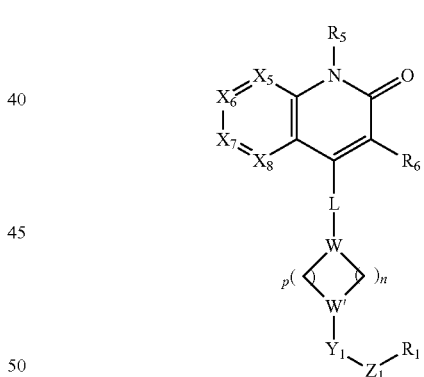

and pharmaceutically acceptable salts, hydrates, solvates, prodrugs, and tautomers thereof;
wherein
L, n and p, W and W', $Y_1$, $Z_1$, $R_1$, $R_2$, $R_3$, and $R_4$, $R_5$, $R_6$ are as defined above for Formula IIa.

In some embodiments, $Y_1$ is a bond.
In some embodiments, $Y_1$ is —$CH_2$—.
In some embodiments, $Y_1$ is —$NR_2$—.
In some embodiments, $Z_1$ is —$N(R_3)(R_4)$—.
In some embodiments, $Z_1$ is —$SO_2$—.
In some embodiments, $R_1$ is a straight chain or branched $C_1$-$C_6$ alkyl.
In some embodiments, $R_1$ is straight chain or branched $C_2$-$C_6$ alkene.

In some embodiments, $R_1$ is

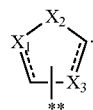

In some embodiments, $R_1$ is

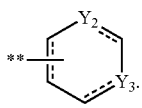

In some embodiments, $R_1$ is

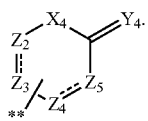

In some embodiments, $R_1$ a 3-6 membered carbacyclic ring
In some embodiments, $R_1$ is a 3-6 membered heterocyclic ring
In some embodiments, $R_1$ is a $C_2$-$C_6$ alkenyl
In some embodiments, $R_1$ is a $C_2$-$C_6$ alkynyl
In some embodiments, $R_1$ is a —Cl
In some embodiments, $X_1$ and $X_3$ are each CH.
In some embodiments, $X_2$ is O.
In some embodiments, $X_2$ is S.
In some embodiments, $X_2$ is $NR_2$.
In some embodiments, $X_4$ is $NR_2$.
In some embodiments, $Y_2$ is CH.
In some embodiments, $Y_2$ is N.
In some embodiments, $Y_4$ is O.
In some embodiments, $Z_2$, $Z_3$, $Z_4$, and $Z_5$ are each CH.
In some embodiments, - - - - - - represents a double bond.
In some embodiments, $R_1$ is

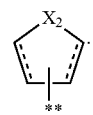

In some embodiments, $R_1$ is

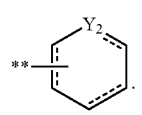

In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In other illustrative embodiments, compounds of Formula IIa are as set forth below:
N-((1-(3-cyano-1-methyl-2-oxo-1,2-dihydroquinolin-4-yl)azetidin-3-yl)methyl)ethenesulfonamide (IIa-1);
N-((3-(3-cyano-1-methyl-2-oxo-1,2-dihydroquinolin-4-ylamino)cyclobutyl)methyl)ethenesulfonamide (IIa-2);
1-methyl-2-oxo-4-(3-(vinylsulfonyl)azetidin-1-yl)-1,2-dihydroquinoline-3-carbonitrile (IIa-3); and
N-((3-(3-cyano-1-methyl-2-oxo-1,2-dihydroquinolin-4-ylamino)cyclobutyl)methyl)acrylamide (IIa-4).

In another aspect, the present invention provides compounds of the Formula III;

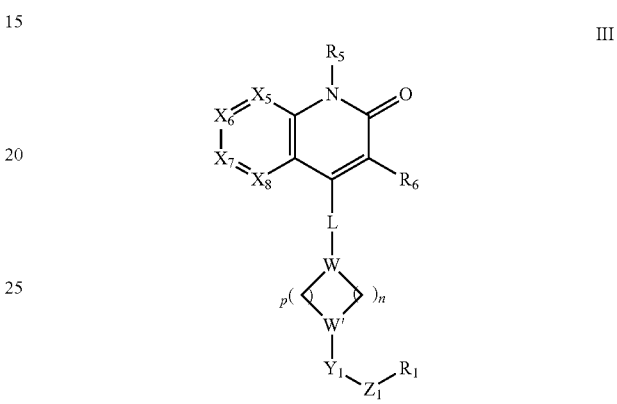

and pharmaceutically acceptable salts, hydrates, solvates, prodrugs, and tautomers thereof;
wherein L, n and p, W and W', Y, $Z_1$, $R_1$, $R_2$, $R_5$, $R_6$ are as defined above for Formula III.
In some embodiments, $Y_1$ is a bond.
In some embodiments, $Y_1$ is —$CH_2$—.
In some embodiments, $Y_1$ is null.
In some embodiments, $Z_1$ is —C(O)—.
In some embodiments, $Z_1$ is —O—.
In some embodiments, $Z_1$ is —N($R_3$)($R_4$)—.
In some embodiments, $Z_1$ is a bond.
In some embodiments, $Z_1$ is —S—.
In some embodiments, $Z_1$ is —$CH_2$—.
In some embodiments, $R_1$ is a straight chain or branched $C_2$-$C_6$ alkyne.
In some embodiments, $R_1$ is a substituted straight chain or branched $C_2$-$C_6$ alkyne.
In some embodiments, $R_1$ is a CN.
In some embodiments, $R_1$ is a straight chain or branched $C_2$-$C_6$ alkene.
In some embodiments, $R_1$ is a substituted straight chain or branched $C_2$-$C_6$ alkene.
In some embodiments, $R_1$ is a straight chain or branched $C_1$-$C_6$ alkyl.
In some embodiments, $R_1$ is a substituted straight chain or branched $C_1$-$C_6$ alkyl.
In some embodiments, $R_1$ is a nonaromatic monocyclic heterocycle.
In some embodiments, $R_1$ is a substituted nonaromatic monocyclic heterocycle.
In some embodiments, $R_1$ is an aromatic monocyclic heterocycle.
In some embodiments, $R_1$ is a substituted aromatic monocyclic heterocycle.
In some embodiments, $R_1$ is an aromatic or nonaromatic monocyclic carbocycle.

In some embodiments, $R_1$ is a substituted aromatic or non-aromatic monocyclic carbocycle.

In some embodiments, $R_1$ is

In some embodiments, $R_1$ is

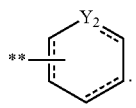

In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In other illustrative embodiments, compounds of Formula III are as set forth below:

1-methyl-2-oxo-4-(-propioloylpiperidin-1-yl)-1,2-dihydroquinoline-3-carbonitrile (III-1);
4-(4-(3-chloropropioloyl)piperidin-1-yl)-1-methyl-2-oxo-1,2-dihydroquinoline-3-carbonitrile (III-2);
4-(4-acryloylpiperidin-1-yl)-1-methyl-2-oxo-1,2-dihydroquinoline-3-carbonitrile (III-3);
4-(4-methacryloylpiperidin-1-yl)-1-methyl-2-oxo-1,2-dihydroquinoline-3-carbonitrile (III-4);
(E)-4-(4-but-2-enoylpiperidin-1-yl)-1-methyl-2-oxo-1,2-dihydroquinoline-3-carbonitrile (III-5);
1-methyl-2-oxo-4-(4-((prop-2-ynyloxy)methyl)piperidin-1-yl)-1,2-dihydroquinoline-3-carbonitrile (III-6);
4-(4-(2-fluoroacetyl)piperidin-1-yl)-1-methyl-2-oxo-1,2-dihydroquinoline-3-carbonitrile (III-7);
4-(4-(2-chloroacetyl)piperidin-1-yl)-1-methyl-2-oxo-1,2-dihydroquinoline-3-carbonitrile (III-8);
1-methyl-2-oxo-4-(4-(2-oxopyrrolidine-1-carbonyl)piperidin-1-yl)-1,2-dihydroquinoline-3-carbonitrile (III-9);
1-methyl-2-oxo-4-(4-((prop-2-ynylamino)methyl)piperidin-1-yl)-1,2-dihydroquinoline-3-carbonitrile (III-10);
3-(1-(3-cyano-1-methyl-2-oxo-1,2-dihydroquinolin-4-yl)piperidin-4-yl)propiolic acid (III-11);
1-methyl-2-oxo-4-(4-(thiocyanatomethyl)piperidin-1-yl)-1,2-dihydroquinoline-3-carbonitrile (III-12);
1-methyl-4-(4-(2-(methylsulfonyl)vinyl)piperidin-1-yl)-2-oxo-1,2-dihydroquinoline-3-carbonitrile (III-13);
4-(1-(3-cyano-1-methyl-2-oxo-1,2-dihydroquinolin-4-yl)piperidin-4-yl)but-2-ynoic acid (III-14);
4-(1-(3-cyano-1-methyl-2-oxo-1,2-dihydroquinolin-4-yl)piperidin-4-yl)-N-methylbut-2-ynamide (III-15);
4-(4-(cyanomethyl)piperidin-1-yl)-1-methyl-2-oxo-1,2-dihydroquinoline-3-carbonitrile (III-16);
N-((1-(3-cyano-1-methyl-2-oxo-1,2-dihydroquinolin-4-yl)piperidin-4-yl)methyl)acrylamide (III-17);
N-(1-(3-cyano-1-methyl-2-oxo-1,2-dihydroquinolin-4-yl)piperidin-4-yl)methacrylamide (III-18);
N-(1-(3-cyano-1-methyl-2-oxo-1,2-dihydroquinolin-4-yl)piperidin-4-yl)propiolamide (III-19);
N-acryloyl-N-(1-(3-cyano-1-methyl-2-oxo-1,2-dihydroquinolin-4-yl)piperidin-4-yl)acrylamide (III-20);
1-methyl-2-oxo-4-(4-(2-oxo-2,5-dihydro-1H-pyrrol-1-yl)piperidin-1-yl)-1,2-dihydroquinoline-3-carbonitrile (III-21);
1-methyl-2-oxo-4-(4-(2-oxo-5,6-dihydropyridin-1(2H)-yl)piperidin-1-yl)-1,2-dihydroquinoline-3-carbonitrile (III-22);
1-methyl-2-oxo-4-(4-(7-oxo-2,3,4,7-tetrahydro-1H-azepin-1-yl)piperidin-1-yl)-1,2-dihydroquinoline-3-carbonitrile (III-23);
4-(4-(cyanomethylamino)piperidin-1-yl)-1-methyl-2-oxo-1,2-dihydroquinoline-3-carbonitrile (III-24);
1-methyl-2-oxo-4-(4-(3-vinyl-1H-pyrazol-5-ylamino)piperidin-1-yl)-1,2-dihydroquinoline-3-carbonitrile (III-25);
1-methyl-2-oxo-4-(4-(thiocyanatomethylamino)piperidin-1-yl)-1,2-dihydroquinoline-3-carbonitrile (III-26);
1-methyl-2-oxo-4-(4-(4-vinylpyrimidin-2-ylamino)piperidin-1-yl)-1,2-dihydroquinoline-3-carbonitrile (III-27);
(E)-ethyl 4-(4-(3-cyano-1-methyl-2-oxo-1,2-dihydroquinolin-4-ylamino)piperidin-1-yl)but-2-enoate (III-28);
(E)-ethyl 3-(1-(3-cyano-1-methyl-2-oxo-1,2-dihydroquinolin-4-yl)azetidin-3-yl)acrylate (III-29); and
(E)-ethyl 3-(3-(3-cyano-1-methyl-2-oxo-1,2-dihydroquinolin-4-ylamino)cyclobutyl)acrylate (III-30).

In another aspect, the present invention provides compounds of the Formula IIIa:

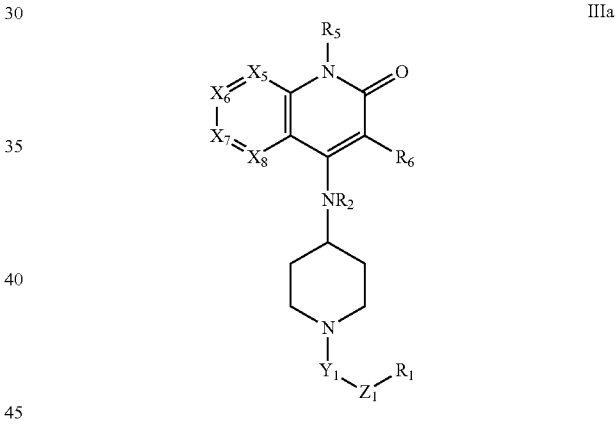

and pharmaceutically acceptable salts, hydrates, solvates, prodrugs, and tautomers thereof;

wherein $Y_1$, $Z_1$, $R_2$, $R_5$, $R_6$, are as defined above for Formula IIIa.

In some embodiments, $Y_1$ is a bond.
In some embodiments, $Y_1$ is —$CH_2$—.
In some embodiments, $Z_1$ is a bond.
In some embodiments, $Z_1$ is —C(O)—.
In some embodiments, $Z_1$ is a —S(O)—.
In some embodiments, $Z_1$ is —S($O_2$)—.
In some embodiments, $R_1$ is a substituted straight chain or branched $C_1$-$C_6$ alkyl.
In some embodiments, $R_1$ is a straight chain or branched $C_2$-$C_6$ alkene.
In some embodiments, $R_1$ is a straight chain or branched $C_2$-$C_6$ alkyne.
In some embodiments, $R_1$ is a $C_3$-$C_4$ cyclic alkyl.
In some embodiments, $R_1$ is a $C_3$-$C_4$ heterocyclic ring.

In some embodiments, R$_1$ is

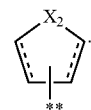

In some embodiments, R$_1$ is

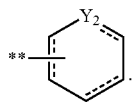

In some embodiments, R$_6$ is —CN.

In other illustrative embodiments, compounds of Formula IIIa are as set forth below:

4-(1-acryloylpiperidin-4-ylamino)-1-methyl-2-oxo-1,2-dihydroquinoline-3-carbonitrile (IIIa-1);
4-(1-acryloylpiperidin-4-ylamino)-1-(4-fluorobenzyl)-2-oxo-1,2-dihydroquinoline-3-carbonitrile (IIIa-2);
1-(4-fluorobenzyl)-2-oxo-4-(1-propioloylpiperidin-4-ylamino)-1,2-dihydroquinoline-3-carbonitrile (IIIa-3);
4-(1-(2-chloroacetyl)piperidin-4-ylamino)-1-(4-fluorobenzyl)-2-oxo-1,2-dihydroquinoline-3-carbonitrile (IIIa-4);
1-(4-fluorobenzyl)-4-(1-(2-fluorothiazole-5-carbonyl)piperidin-4-ylamino)-2-oxo-1,2-dihydroquinoline-3-carbonitrile (IIIa-5);
1-(4-fluorobenzyl)-2-oxo-4-(1-(vinylsulfinyl)piperidin-4-ylamino)-1,2-dihydroquinoline-3-carbonitrile (IIIa-6);
1-methyl-2-oxo-4-(1-(vinylsulfonyl)piperidin-4-ylamino)-1,2-dihydroquinoline-3-carbonitrile (IIIa-7);
4-(1-(cyanomethyl)piperidin-4-ylamino)-1-(4-fluorobenzyl)-2-oxo-1,2-dihydroquinoline-3-carbonitrile (IIIa-8);
1-(4-fluorobenzyl)-2-oxo-4-(1-(thiocyanatomethyl)piperidin-4-ylamino)-1,2-dihydroquinoline-3-carbonitrile (IIIa-9);
1-methyl-2-oxo-4-(1-(4-vinylpyrimidine-2-carbonyl)piperidin-4-ylamino)-1,2-dihydroquinoline-3-carbonitrile (IIIa-10);
4-(1-(1-cyanocyclopropanecarbonyl)piperidin-4-ylamino)-1-methyl-2-oxo-1,2-dihydroquinoline-3-carbonitrile (IIIa-11);
1-methyl-2-oxo-4-(1-(2-(trifluoromethyl)acryloyl)piperidin-4-ylamino)-1,2-dihydroquinoline-3-carbonitrile (IIIa-12);
1-methyl-2-oxo-4-(1-(2-oxopyrrolidine-1-carbonyl)piperidin-4-ylamino)-1,2-dihydroquinoline-3-carbonitrile (IIIa-13);
4-(1-acryloylpiperidin-4-ylamino)-1-(2-(dim ethylamino)ethyl)-2-oxo-1,2-dihydroquinoline-3-carbonitrile (IIIa-14);
4-((1-(2-chloroacetyl)piperidin-4-yl)amino)-1-(4-fluorobenzyl)-2-oxo-1,2-dihydroquinoline-3-carbonitrile (IIIa-15);
4-((1-acryloylpiperidin-4-yl)amino)-1-(4-fluorobenzyl)-2-oxo-1,2-dihydroquinoline-3-carbonitrile (IIIa-16);
1-(4-fluorobenzyl)-2-oxo-4-((1-propioloylpiperidin-4-yl)amino)-1,2-dihydroquinoline-3-carbonitrile (IIIa-17);
4-((1-(2-chloroacetyl)piperidin-4-yl)amino)-1-(2-ethoxyethyl)-2-oxo-1,2-dihydroquinoline-3-carbonitrile (IIIa-18);
4-((1-acryloylpiperidin-4-yl)amino)-7-fluoro-1-(4-fluorobenzyl)-2-oxo-1,2-dihydroquinoline-3-carbonitrile (IIIa-19);
4-((1-(2-chloroacetyl)piperidin-4-yl)amino)-1-(3-(dimethylamino)propyl)-2-oxo-1,2-dihydroquinoline-3-carbonitrile (IIIa-20);
4-((1-(2-chloroacetyl)piperidin-4-yl)amino)-6-fluoro-1-(4-fluorobenzyl)-2-oxo-1, dihydroquinoline-3-carbonitrile (IIIa-21);
4-((1-(2-chloroacetyl)piperidin-4-yl)amino)-1-(4-fluorobenzyl)-2-oxo-1,2-dihydro-1,6-naphthyridine-3-carbonitrile (IIIa-22);
4-((1-(2-chloroacetyl)piperidin-4-yl)amino)-1-(4-fluorobenzyl)-2-oxo-1,2-dihydro-1,7-naphthyridine-3-carbonitrile (IIIa-23);
1-(4-fluorobenzyl)-2-oxo-4-((1-(vinylsulfonyl)piperidin-4-yl)amino)-1,2-dihydroquinoline-3-carbonitrile (IIIa-24);
4-((1-(ethynylsulfonyl)piperidin-4-yl)amino)-1-(4-fluorobenzyl)-2-oxo-1,2-dihydroquinoline-3-carbonitrile (IIIa-25); and
1-(4-fluorobenzyl)-2-oxo-4-((1-(vinylsulfinyl)piperidin-4-yl)amino)-1, -dihydroquinoline-3-carbonitrile (IIIa-26).

In another aspect, the present invention provides compounds of Formula IIIb:

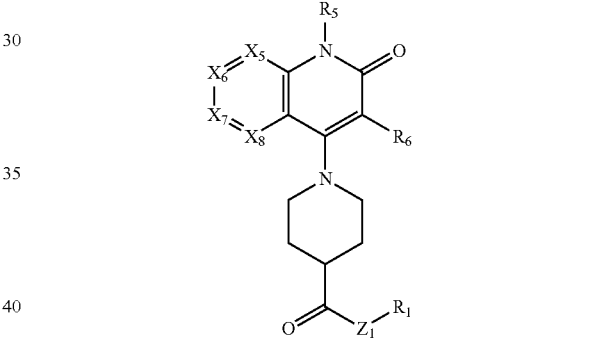

and pharmaceutically acceptable salts, hydrates, solvates, prodrugs, and tautomers thereof;

wherein

Z$_1$, R$_1$, R$_2$, R$_5$, R$_6$ are as defined above for Formula IIIb.

In some embodiments, Z$_1$ is —N(R$_3$)(R$_4$)—.

In some embodiments, Z$_1$ is —O—.

In some embodiments, Z$_1$ is —S—.

In some embodiments, R$_1$ is CN.

In some embodiments, R$_1$ is a straight chain or branched C$_1$-C$_6$ alkyl.

In some embodiments, R$_1$ is a straight chain or branched C$_1$-C$_6$ alkene

In some embodiments, R$_1$ is a straight chain or branched C$_1$-C$_6$ alkyne.

In some embodiments, R$_1$ is a substituted straight chain or branched C$_1$-C$_6$ alkyl.

In some embodiments, R$_1$ is an aromatic or nonaromatic monocyclic heterocycle.

In some embodiments, R$_1$ is a substituted aromatic or nonaromatic monocyclic heterocycle.

In some embodiments, R₁ is

[structure: 5-membered ring with X₂]

In some embodiments, R₁ is

[structure: 6-membered ring with Y₂]

In some embodiments, R₆ is —CN.
In some embodiments, Z₁ is NH.
In other illustrative embodiments, compounds of Formula IIIb are as set forth below:

1-(3-cyano-1-methyl-2-oxo-1,2-dihydroquinolin-4-yl)-N-(cyanomethyl)piperidine-4-carboxamide (IIIb-1);
ethyl 1-(3-cyano-1-methyl-2-oxo-1,2-dihydroquinolin-4-yl)piperidine-4-carboxylate (IIIb-2);
S-pyridin-2-yl 1-(3-cyano-1-methyl-2-oxo-1,2-dihydroquinolin-4-yl)piperidine-4-carbothioate (IIIb-3);
1-(3-cyano-1-methyl-2-oxo-1,2-dihydroquinolin-4-yl)-N-(6-ethynylpyridin-2-yl)piperidine-4-carboxamide (IIIb-4);
4-((4-acryloylcyclohexyl)amino)-1-(4-fluorobenzyl)-2-oxo-1,2-dihydroquinoline-3carbonitrile (IIIb-5);
4-((4-acryloylcyclohexyl)amino)-1-(4-fluorobenzyl)-2-oxo-1,2-dihydro-1,6-naphthyridine-3-carbonitrile (IIIb-6);
1-(4-fluorobenzyl)-2-oxo-4-((4-propioloylcyclohexyl)amino)-1,2-dihydroquinoline-3-carbonitrile (IIIb-7);
4-((4-acryloylcyclohexyl)amino)-2-oxo-1-(2-propoxyethyl)-1,2-dihydroquinoline-3carbonitrile (IIIb-8);
4-((4-acryloylcyclohexyl)amino)-6-fluoro-1-(4-fluorobenzyl)-2-oxo-1,2-dihydroquinoline-3-carbonitrile (IIIb-9);
4-((4-acryloylcyclohexyl)amino)-1-(3-(dimethylamino)propyl)-2-oxo-1,2-dihydroquinoline-3-carbonitrile (IIIb-10);
4-((4-acryloylcyclohexyl)amino)-7-fluoro-1-(4-fluorobenzyl)-2-oxo-1,2-dihydroquinoline-3-carbonitrile (IIIb-11);
4-((3-cyano-1-(4-fluorobenzyl)-2-oxo-1,2-dihydroquinolin-4-yl)amino)-N-(cyanomethyl)cyclohexanecarboxamide (IIIb-12); and
4-((4-acryloylcyclohexyl)amino)-1-(4-fluorobenzyl)-2-oxo-1,2-dihydro-1,7-naphthyridine-3-carbonitrile (IIIb-13).

In another aspect, the present invention provides compounds of Formula IIIc:

[structure IIIc]

and pharmaceutically acceptable salts, hydrates, solvates, prodrugs, and tautomers thereof;
wherein $Z_1$, $R_1$, $R_2$, $R_5$, $R_6$ are as defined above for Formula IIIc.

In some embodiments, $Z_1$ is —C(O)—.
In some embodiments, $Z_1$ is —SO₂.
In some embodiments $R_1$ is a straight chain or branched $C_1$-$C_6$ alkyl.
In some embodiments, $R_1$ is a substituted straight chain or branched $C_1$-$C_6$ alkyl.
In some embodiments, $R_1$ is a straight chain or branched $C_2$-$C_6$ alkene.
In some embodiments, $R_1$ is a substituted straight chain or branched $C_2$-$C_6$ alkene.
In some embodiments, $R_1$ is a straight chain or branched $C_2$-$C_6$ alkyne.
In some embodiments, $R_1$ is a substituted straight chain or branched $C_2$-$C_6$ alkyne.
In some embodiments, $R_1$ is a substituted nonaromatic monocyclic carbocycle.
In some embodiments, $R_1$ is

[structure: 5-membered ring with X₂]

In some embodiments, $R_1$ is

[structure: 6-membered ring with Y₂]

In some embodiments, $R_6$ is —CN.
In other illustrative embodiments, compounds of Formula IIIc are as set forth below:
N-(1-(3-cyano-1-methyl-2-oxo-1,2-dihydroquinolin-4-yl)piperidin-4-yl)acrylamide (IIIc-1);
1-cyano-N-(1-(3-cyano-1-methyl-2-oxo-1,2-dihydroquinolin-4-yl)piperidin-4-yl)cyclopropanecarboxamide (IIIc-2);
(E)-3-chloro-N-(1-(3-cyano-1-methyl-2-oxo-1,2-dihydroquinolin-4-yl)piperidin-4-yl)acrylamide (IIIc-3);

2-chloro-N-(1-(3-cyano-1-methyl-2-oxo-1,2-dihydroquinolin-4-yl)piperidin-4-yl)acetamide (IIIc-4);
N-(1-(3-cyano-1-methyl-2-oxo-1,2-dihydroquinolin-4-yl)piperidin-4-yl)-2-fluoroacetamide (IIIc-5);
N-(1-(3-cyano-1-methyl-2-oxo-1,2-dihydroquinolin-4-yl)piperidin-4-yl)ethenesulfonamide (IIIc-6);
N-(1-(3-cyano-1-methyl-2-oxo-1,2-dihydroquinolin-4-yl)piperidin-4-yl)ethynesulfonamide (IIIc-7);
N-(1-(3-cyano-1-methyl-2-oxo-1,2-dihydroquinolin-4-yl)piperidin-4-yl)-2-(trifluoromethyl)acrylamide (IIIc-8);
N-(1-(3-cyano-1-methyl-2-oxo-1,2-dihydroquinolin-4-yl)piperidin-4-yl)-2-fluorothiazole-5-carboxamide (IIIc-9) and;
4-((1-(2-chloroacetyl)piperidin-4-yl)amino)-1-methyl-2-oxo-1,2-dihydroquinoline-3-carbonitrile (IIIc-10);
4-((1-(2-chloroacetyl)piperidin-4-yl)amino)-1-(4-fluorobenzyl)-2-oxo-1,2-dihydroquinoline-3-carbonitrile (IIIc-11);
4-((1-acryloylpiperidin-4-yl)amino)-1-(4-fluorobenzyl)-2-oxo-1,2-dihydroquinoline-3-carbonitrile (IIIc-12);
4-((1-(2-chloroacetyl)piperidin-4-yl)amino)-1-methyl-2-oxo-1,2-dihydro-1,6-naphthyridine-3-carbonitrile (IIIc-13);
4-((1-(2-chloroacetyl)piperidin-4-yl)amino)-1-(2-ethoxyethyl)-2-oxo-1,2-dihydroquinoline-3-carbonitrile (IIIc-14);
4-((1-acryloylpiperidin-4-yl)amino)-1-(4-fluorobenzyl)-2-oxo-1,2-dihydro-1,6-naphthyridine-3-carbonitrile (IIIc-15);
4-((1-(oxirane-2-carbonyl)piperidin-4-yl)amino)-2-oxo-1-(2-propoxyethyl)-1,2-dihydroquinoline-3-carbonitrile (IIIc-16);
4-((1-(1-cyanocyclopropanecarbonyl)piperidin-4-yl)amino)-1-(4-fluorobenzyl)-2-oxo-1,2-dihydroquinoline-3-carbonitrile (IIIc-17);
4-((1-acryloylpiperidin-4-yl)amino)-1-(4-fluorobenzyl)-2-oxo-1,2-dihydroquinoline-3,6-dicarbonitrile (IIIc-18);
1-methyl-2-oxo-4-((1-propioloylpiperidin-4-yl)amino)-1,2-dihydroquinoline-3-carbonitrile (IIIc-19);
1-(4-fluorobenzyl)-2-oxo-4-((1-propioloylpiperidin-4-yl)amino)-1,2-dihydroquinoline-3-carbonitrile (IIIc-20); and
4-((1-acryloylpiperidin-4-yl)amino)-6-fluoro-1-(4-fluorobenzyl)-2-oxo-1,2-dihydroquinoline-3-carbonitrile (IIIc-21).

In another aspect, the present invention provides compounds of the Formula IIId:

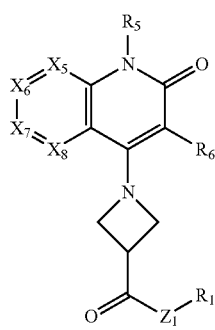

IIId and pharmaceutically acceptable salts, hydrates, solvates, prodrugs, and tautomers thereof;

wherein $R_1$, $R_2$, $R_5$, $R_6$ are as defined above for Formula IIId.
In some embodiments $Z_1$ is a bond.
In some embodiments $Z_1$ is —S—.
In some embodiments $Z_1$ is —N($R_3$)($R_4$).
In some embodiments, $R_1$ is a straight chain or branched $C_1$-$C_6$ alkyl.
In some embodiments, $R_1$ is a straight chain or branched $C_2$-$C_6$ alkene.
In some embodiments, $R_1$ is a straight chain or branched $C_2$-$C_6$ alkyne.
In some embodiments, $R_1$ is

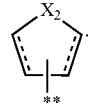

In some embodiments, $R_1$ is

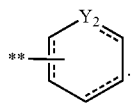

In some embodiments, $R_6$ is —CN.
In other illustrative embodiments, compounds of Formula IIId are as set forth below:
4-(3-acryloylazetidin-1-yl)-1-methyl-2-oxo-1,2-dihydroquinoline-3-carbonitrile (IIId-1);
4-(3-acryloylazetidin-1-yl)-1-(4-fluorobenzyl)-2-oxo-1,2-dihydroquinoline-3-carbonitrile (IIId-2);
4-(3-acryloylazetidin-1-yl)-1-(2-(dimethylamino)ethyl)-2-oxo-1,2-dihydroquinoline-3-carbonitrile (IIId-3);
1-methyl-2-oxo-4-(3-propioloylazetidin-1-yl)-1,2-dihydroquinoline-3-carbonitrile (IIId-4);
4-(3-acryloylazetidin-1-yl)-1-benzyl-2-oxo-1,2-dihydroquinoline-3-carbonitrile (IIId-5);
1-(3-cyano-1-methyl-2-oxo-1,2-dihydroquinolin-4-yl)-N-(cyanomethyl)azetidine-3-carboxamide (IIId-6);
1-methyl-2-oxo-4-(3-(2-(trifluoromethyl)acryloyl)azetidin-1-yl)-1,2-dihydroquinoline-3-carbonitrile (IIId-7);
N-((1-(3-cyano-1-methyl-2-oxo-1,2-dihydroquinolin-4-yl)azetidin-3-yl)methyl)acrylamide (IIId-8);
1-methyl-2-oxo-4-(3-(2-oxopyrrolidine-1-carbonyl)azetidin-1-yl)-1,2-dihydroquinoline-3-carbonitrile (IIId-9);
4-(3-(2-chloroacetyl)azetidin-1-yl)-1-(4-fluorobenzyl)-2-oxo-1,2-dihydroquinoline-3carbonitrile (IIId-10);
ethyl 4-(3-acryloylazetidin-1-yl)-1-methyl-2-oxo-1,2-dihydroquinoline-3-carboxylate (IIId-11);
1-(3-cyano-1-methyl-2-oxo-1,2-dihydroquinolin-4-yl)-N-(6-ethynyl pyridin-2-yl)azetidine-3-carboxamide (IIId-12);
1-(3-cyano-1-methyl-2-oxo-1,2-dihydroquinolin-4-yl)-N-(2-fluorothiazol-5-yl)azetidine-3-carboxamide (IIId-13);
S-pyridin-2-yl 1-(3-cyano-1-methyl-2-oxo-1,2-dihydroquinolin-4-yl)azetidine-3-carbothioate (IIId-14);
(E)-4-(3-(2-chloroacetyl)azetidin-1-yl)-5-ethylidene-1-methyl-6-methylene-2-oxo-1,2,5,6-tetrahydropyridine-3-carbonitrile (IIId-15);
1-(3-cyano-1-(4-fluorobenzyl)-2-oxo-1,2-dihydroquinolin-4-yl)-N-(cyanomethyl)azetidine-3-carboxamide (IIId-16);
1-(3-cyano-1-(2-ethoxyethyl)-2-oxo-1,2-dihydroquinolin-4-yl)-N-(cyanomethyl)azetidine-3-carboxamide (IIId-17);

1-(4-fluorobenzyl)-2-oxo-4-(3-propioloylazetidin-1-yl)-1,2-dihydroquinoline-3-carbonitrile (IIId-18);

4-(3-acryloylazetidin-1-yl)-6-fluoro-1-(4-fluorobenzyl)-2-oxo-1,2-dihydroquinoline-3-carbonitrile (IIId-19);

4-(3-acryloylazetidin-1-yl)-1-(4-fluorobenzyl)-2-oxo-1,2-dihydro-1,6-naphthyridine-3-carbonitrile (IIId-20);

4-(3-acryloylazetidin-1-yl)-1-(4-fluorobenzyl)-2-oxo-1,2-dihydroquinoline-3-carbonitrile (IIId-21);

4-(3-acryloylazetidin-1-yl)-7-fluoro-1-(4-fluorobenzyl)-2-oxo-1,2-dihydroquinoline-3-carbonitrile (IIId-22);

4-(3-acryloylazetidin-1-yl)-6-chloro-1-(4-fluorobenzyl)-2-oxo-1,2-dihydroquinoline-3-carbonitrile (IIId-23); and 1-(4-fluorobenzyl)-2-oxo-4-(3-propioloylazetidin-1-yl)-1,2-dihydro-1,6-naphthyridine-3-carbonitrile (IIId-24).

In another aspect, the present invention provides compounds of the Formula IIIe:

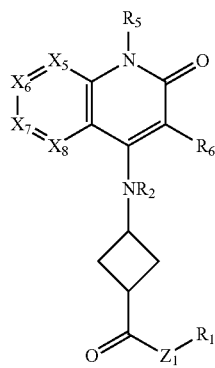

IIIe and pharmaceutically acceptable salts, hydrates, solvates, prodrugs, and tautomers thereof;

wherein $Z_1$, $R_1$, $R_2$, $R_5$, $R_6$ are as defined above for Formula IIIe.

In some embodiments, $Z_1$ is a bond.

In some embodiments, $Z_1$ is —N($R_3$)($R_4$).

In some embodiments, $R_1$ is a straight chain or branched $C_1$-$C_6$ alkyl.

In some embodiments, $R_1$ is a straight chain or branched $C_2$-$C_6$ alkene.

In some embodiments, $R_1$ is , a straight chain or branched $C_2$-$C_6$ alkyne.

In some embodiments, $R_1$ is

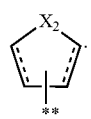

In some embodiments, $R_1$ is

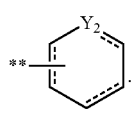

In some embodiments, $R_6$ is —CN.

In other illustrative embodiments, compounds of Formula IIIe are as set forth below:

4-(3-acryloylcyclobutylamino)-1-methyl-2-oxo-1,2-dihydroquinoline-3-carbonitrile (IIIe-1);

4-(3-acryloylcyclobutylamino)-1-(4-fluorobenzyl)-2-oxo-1,2-dihydroquinoline-3-carbonitrile (IIIe-2);

4-(3-acryloylcyclobutylamino)-1-(2-(dimethylamino)ethyl)-2-oxo-1,2-dihydroquinoline-3-carbonitrile (IIIe-3);

1-methyl-2-oxo-4-(3-propioloylcyclobutylamino)-1,2-dihydroquinoline-3-carbonitrile (IIIe-4);

3-(3-cyano-1-methyl-2-oxo-1,2-dihydroquinolin-4-ylamino)-N-(cyanomethyl)cyclobutanecarboxamide (IIIe-5);

1-methyl-2-oxo-4-(3-(2-(trifluoromethyl)acryloyl)cyclobutylamino)-1,2-dihydroquinoline-3-carbonitrile (IIIe-6);

3-(3-cyano-1-methyl-2-oxo-1,2-dihydroquinolin-4-ylamino)-N-(4-vinylpyrimidin-2-yl)cyclobutanecarboxamide (IIIe-7);

1-methyl-2-oxo-4-(3-(2-oxopyrrolidine-1-carbonyl)cyclobutylamino)-1,2-dihydroquinoline-3-carbonitrile (IIIe-8);

4-(3-(2-chloroacetyl)cyclobutylamino)-1-methyl-2-oxo-1,2-dihydroquinoline-3-carbonitrile (IIIe-9);

4-(3-(2-chloro acetyl)cyclobutylamino)-1-(4-fluorobenzyl)-2-oxo-1,2-dihydroquinoline-3-carbonitrile (IIIe-10);

3-(3-cyano-1-methyl-2-oxo-1,2-dihydroquinolin-4-ylamino)-N-(2-fluorothiazol-5-yl)cyclobutanecarboxamide (IIIe-11);

4-(3-acryloylcyclobutylamino)-1-benzyl-2-oxo-1,2-dihydroquinoline-3-carbonitrile (IIIe-12);

ethyl 4-(3-acryloylcyclobutylamino)-1-methyl-2-oxo-1,2-dihydroquinoline-3-carboxylate (IIIe-13);

4-((3-acryloylcyclobutyl)(methyl)amino)-1-methyl-2-oxo-1,2-dihydroquinoline-3-carbonitrile (IIIe-14);

4-((3-acryloylcyclobutyl)amino)-2-oxo-1-(2-propoxyethyl)-1,2-dihydroquinoline-3-carbonitrile (IIIe-15);

4-((3-acryloylcyclobutyl)amino)-1-(4-fluorobenzyl)-2-oxo-1,2-dihydroquinoline-3-carbonitrile (IIIe-16);

1-(4-fluorobenzyl)-2-oxo-4-((3-propioloylcyclobutyl)amino)-1,2-dihydroquinoline-3-carbonitrile (IIIe-17)

3-((3-cyano-2-oxo-1-(2-propoxyethyl)-1,2-dihydroquinolin-4-yl)amino)-N-(cyanomethyl)cyclobutanecarboxide (IIIe-18);

4-((3-acryloylcyclobutyl)amino)-1-(4-fluorobenzyl)-2-oxo-1,2-dihydro-1,6-naphthyridine-3-carbonitrile (IIIe-19);

6-fluoro-1-(4-fluorobenzyl)-2-oxo-4-((3-propioloylcyclobutyl)amino)-1,2-dihydroquinoline-3-carbonitrile (IIIe-20);

4((3-acryloylcyclobutyl)amino)-1-(3-(dimethylamino)propyl)-2-oxo-1,2-dihydroquinoline-3-carbonitrile (IIIe-21

4-((3-acryloylcyclobutyl)amino)-7-fluoro-1-(4-fluorobenzyl)-2-oxo-1,2-dihydroquinoline-3-carbonitrile (IIIe-22);

4-((3-acryloylcyclobutyl)amino)-1-(4-fluorobenzyl)-2-oxo-1,2-dihydro-1,7-naphthyridine-3-carbonitrile (IIIe-23).

In another aspect, the present invention provides compounds of the Formula IIIf

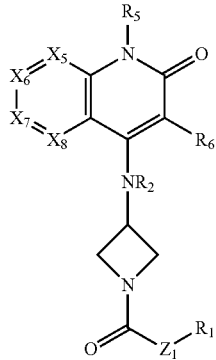

IIIf and pharmaceutically acceptable salts, hydrates, solvates, prodrugs, and tautomers thereof;
wherein $Z_1$, $R_1$, $R_2$, $R_5$, $R_6$ are as defined above for Formula Inf.

In some embodiments, $R_1$ is

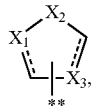

$X_1$ and $X_3$ are each CH; and
each ------- represents a double bond.
In some embodiments, $R_1$ is

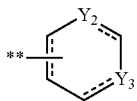

and $Y_3$ is CH and
each ------- represents a double bond.

In other illustrative embodiments, compounds of Formula IIIf are as set forth below:

4-((1-(1-cyanocyclopropanecarbonyl)azetidin-3-yl)amino-1-(4-fluorobenzyl)-2-oxo-1,2-dihydroquinoline-3-carbonitrile (IIIf-1);
1-benzyl-4-((1-(2-chloroacetyl)azetidin-3-yl)amino-2-oxo-1,2-dihydroquinoline-3-carbonitrile (IIIf-2);
4-((1-acryloylazetidin-3-yl)amino)-1-(3-fluorobenzyl)-2-oxo-1,2-dihydroquinoline-3-carbonitrile (IIIf-3);
1-benzyl-2-oxo-4-((1-propioloylazetidin-3-yl)amino)-1,2-dihydroquinoline-3-carbonitrile (IIIf-4);
4-((1-(2-chloroacetyl)azetidin-3-yl)amino)-7-fluoro-1-(3-fluorobenzyl)-2-oxo-1,2-dihydroquinoline-3-carbonitrile (IIIf-5);
4-((1-(2-chloroacetyl)azetidin-3-yl)amino)-1-(4-fluorobenzyl)-2-oxo-1,2-dihydro-1,6-naphthyridine-3-carbonitrile (IIIf-6);
4-((1-(2-chloroacetyl)azetidin-3-yl)amino)-1-(4-fluorobenzyl)-2-oxo-6-(trifluoromethyl)-1,2-dihydroquinoline-3-carbonitrile (IIIf-7);
4-((1-acryloylazetidin-3-yl)amino)-6-fluoro-1-(4-fluorobenzyl)-2-oxo-1,2-dihydroquinoline-3-carbonitrile (IIIf-8);
4-((1-(2-chloroacetyl)azetidin-3-yl)amino)-1-(2-morpholinoethyl)-2-oxo-1dihydroquinoline-3-carbonitrile (IIIf-9);
4-((1-(2-chloroacetyl)azetidin-3-yl)amino)-1-(4-chlorobenzyl)-2-oxo-1,2-dihydroquinoline-3-carbonitrile (IIIf-10);
4-((1-(2-chloroacetyl)azetidin-3-yl)amino)-1-(4-methylbenzyl)-2-oxo-1,2-dihydroquinoline-3-carbonitrile (IIIf-11);
4-((1-acryloylazetidin-3-yl)amino)-1-(4-fluorobenzyl)-2-oxo-1,2-dihydro-1,5-naphthyridine-3-carbonitrile (IIIf-12);
1(2-(dimethylamino)ethyl)-2-oxo-4-((1-propioloylazetidin-3-yl)amino)-1,2-dihydroquinoline-3-carbonitrile (IIIf-13);
4-((1-(2-chloroacetyl)azetidin-3-yl)amino)-1-(2-ethoxyethyl)-7-fluoro-2-oxo-1,2-dihydroquinoline-3-carbonitrile (IIIf-14);
4-((1-(2-chloro acetyl)azetidin-3-yl)amino)-1-(3-(dimethylamino)propyl)-6-fluoro-2-oxo-1,2-dihydroquinoline-3-carbonitrile (IIIf-15);
4-((1-(oxirane-2-carbonyl)azetidin-3-yl)amino)-2-oxo-1-(2-propoxyethyl)-1,2-dihydroquinoline-3-carbonitrile (IIIf-16);
4-((1-(1-cyanocyclopropanecarbonyl)azetidin-3-yl)amino)-1-(2-ethoxyethyl)-2-oxo-1,2-dihydroquinoline-3-carbonitrile (IIIf-17);
4-((1-(2-chloroacetyl)azetidin-3-yl)amino)-1-(4-fluorobenzyl)-2-oxo-1,2-dihydro-1,8-naphthyridine-3-carbonitrile (IIIf-18);
1-(4-fluorobenzyl)-4-((1-(oxirane-2-carbonyl)azetidin-3-yl)amino-2-oxo-1,2-dihydroquinoline-3-carbonitrile (IIIf-19);
1-(4-fluorobenzyl)-4-((1-methacryloylazetidin-3-yl)amino)-2-oxo-1,2-dihydroquinoline-3-carbonitrile (IIIf-20);
4-((1-acryloylazetidin-3-yl)amino)-7-chloro-1-(4-fluorobenzyl)-2-oxo-1,2-dihydroquinoline-3-carbonitrile (IIIf-21);
4-((1-acryloylazetidin-3-yl)amino)-1-(2-(dimethylamino)ethyl)-2-oxo-1,2-dihydroquinoline-3-carbonitrile (IIIf-22);
4-((1-(2-chloroacetyl)azetidin-3-yl)amino)-1-(2-(dimethylamino)ethyl)-7-fluoro-2-oxo-1,2-dihydroquinoline-3-carbonitrile (IIIf-23);
4-((1-(2-chloroacetyl)azetidin-3-yl)amino)-1-(3-(dimethylamino)propyl)-2-oxo-1,2-dihydroquinoline-3-carbonitrile (IIIf-24);
2-oxo-4-((1-propioloylazetidin-3-yl)amino)-1-(2-propoxyethyl)-1,2-dihydroquinoline-3-carbonitrile (IIIf-25);
4-((1-(2-chloroacetyl)azetidin-3-yl)amino)-1-(2-ethoxyethyl)-7-fluoro-2-oxo-1,2-dihydroquinoline-3-carbonitrile (IIIf-26);
1-(4-fluorobenzyl)-2-oxo-4-((1-(vinylsulfonyl)azetidin-3-yl)amino)-1,2-dihydroquinoline-3-carbonitrile (IIIf-27);
4-((1-acryloylazetidin-3-yl)amino)-1-(4-fluorobenzyl)-2-oxo-1,2-dihydroquinoline-3-carbonitrile (IIIf-28);
1-(4-fluorobenzyl)-2-oxo-4-((1-propioloylazetidin-3-yl)amino)-1,2-dihydroquinoline-3-carbonitrile (IIIf-29);
4-((1-acryloylazetidin-3-yl)amino)-7-fluoro-1-(4-fluorobenzyl)-2-oxo-1,2-dihydroquinoline-3-carbonitrile (IIIf-30);
4-((1-acryloylazetidin-3-yl)amino)-1-(4-fluorobenzyl)-2-oxo-1,2-dihydro-1,7-naphthyridine-3-carbonitrile (IIIf-31);
4-((1-(2-chloroacetyl)azetidin-3-yl)amino)-1-(4-fluorobenzyl)-2-oxo-1,2-dihydro-1,6-naphthyridine-3-carbonitrile (IIIf-32);
4-((1-(2-chloroacetyl)azetidin-3-yl)amino)-1-(4-fluorobenzyl)-2-oxo-1,2-dihydro-1,7-naphthyridine-3-carbonitrile (IIIf-33);

1-(4-fluorobenzyl)-2-oxo-4-((1-propioloylazetidin-3-yl) amino)-1,2-dihydro-1,6-naphthyridine-3-carbonitrile (IIIf-34);

4-((1-(2-chloroacetyl)azetidin-3-yl)amino)-1-(2-ethoxyethyl)-2-oxo-1,2-dihydroquinoline-3-carbonitrile (IIIf-35);

4-((1-(2-chloroacetyl)azetidin-3-yl)amino)-2-oxo-1-(2-propoxyethyl)-1,2-dihydroquinoline-3-carbonitrile (IIIf-36);

5-((1-acryloylazetidin-3-yl)amino)-8-(4-fluorobenzyl)-2-methyl-7-oxo-7,8-dihydropyrido[2,3-d]pyrimidine-6-carbonitrile (IIIf-37);

4-((1-acryloylazetidin-3-yl)-amino)-1-(4-fluorobenzyl)-7-methyl-2-oxo-1,2-dihydro-1,6-naphthyridine-3-carbonitrile (III-38);

4-((1-acryloylazetidin-3-yl)-amino)-1-(4-fluorobenzyl)-6-methyl-2-oxo-1,2-dihydro-1,7-naphthyridine-3-carbonitrile (IIIf-39);

4-((1-acryloylazetidin-3-yl)amino)-6,7-difluoro-1-(4-fluorobenzyl)-2-oxo-1,2-dihydroquinoline-3-carbonitrile (IIIf-40);

4-((1-acryloylazetidin-3-yl)amino)-1-(4-fluorobenzyl)-2-oxo-1,2-dihydroquinoline-3,7-dicarbonitrile (IIIf-41);

4-((1-acryloylazetidin-3-yl)amino)-1-(4-fluorobenzyl)-2-oxo-1,2-dihydroquinoline-3,6-dicarbonitrile (IIIf-42);

4-((1-acryloylazetidin-3-yl)amino)-1-(cyclopropylmethyl)-6-fluoro-2-oxo-1,2-dihydroquinoline-3-carbonitrile (IIIf-43);

4-((1-acryloylazetidin-3-yl)amino)-7-chloro-1-(4-fluorobenzyl)-2-oxo-6-(trifluoromethyl)-1,2-dihydroquinoline-3-carbonitrile (IIIf-44); and 4-((1-acryloylazetidin-3-yl)amino)-1-(4-fluorobenzyl)-2-oxo-1,2-dihydroquinoline-3,7-dicarbonitrile (IIIf-45).

In another aspect, the present invention provides compounds of the Formula IIIg

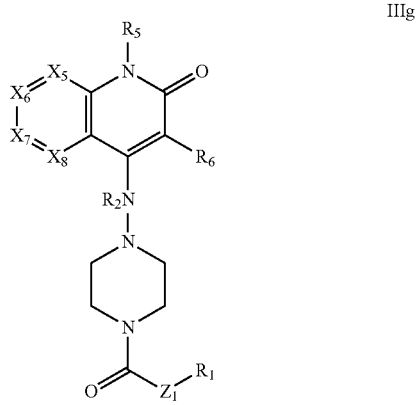

IIIg and pharmaceutically acceptable salts, hydrates, solvates, prodrugs, and tautomers thereof;

wherein $Z_1$, $R_1$, $R_2$, $R_5$, $R_6$ are as defined above for Formula IIIg.

In some illustrative embodiments, compounds of Formula IIIg are as set forth below, 1-(4-fluorobenzyl)-2-oxo-4-(4-(vinylsulfonyl)piperazin-1-yl)-1,2-dihydroquinoline-3-carbonitrile (IIIg-1);

4-(4-acryloylpiperazin-1-yl)-7-fluoro-1-(4-fluorobenzyl)-2-oxo-1,2-dihydroquinoline-3-carbonitrile (IIIg-2);

7-chloro-4-(4-(2-chloroacetyl)piperazin-1-yl)-1-(4-fluorobenzyl)-2-oxo-1,2-dihydroquinoline-3-carbonitrile (IIIg-3);

4-(4-acryloylpiperazin-1-yl)-1-(2-ethoxyethyl)-2-oxo-1,2-dihydroquinoline-3-carbonitrile (IIIg-4);

4-(4-acryloylpiperazin-1-yl)-2-oxo-1-(2-propoxyethyl)-1,2-dihydroquinoline-3-carbonitrile (IIIg-5);

4-(4-acryloylpiperazin-1-yl)-1-(2-(dimethylamino)ethyl)-2-oxo-1,2-dihydroquinoline-3-carbonitrile (IIIg-6);

1-benzyl-4-(4-(2-chloroacetyl)piperazin-1-yl)-2-oxo-1,2-dihydroquinoline-3-carbonitrile (IIIg-7);

1-(2-ethoxyethyl)-2-oxo-4-(4-propioloylpiperazin-1-yl)-1,2-dihydroquinoline-3carbonitrile (IIIg-8);

4-(4-(2-chloroacetyl)piperazin-1-yl)-1-(4-fluorobenzyl)-2-oxo-1,2-dihydro-1,6-naphthyridine-3-carbonitrile (IIIg-9);

1-(4-fluorobenzyl)-2-oxo-4-(4-(vinylsulfonyl)piperazin-1-yl)-1,2-dihydroquinoline-3-carbonitrile (IIIg-10);

4-(4-acryloylpiperazin-1-yl)-7-fluoro-1-(4-fluorobenzyl)-2-oxo-1,2-dihydroquinoline-3-carbonitrile (IIIg-11);

7-chloro-4-(4-(2-chloroacetyl)piperazin-1-yl)-1-(4-fluorobenzyl)-2-oxo-1,2-dihydroquinoline-3-carbonitrile (IIIg-12);

4-(4-acryloylpiperazin-1-yl)-1-(2-ethoxyethyl)-2-oxo-1,2-dihydroquinoline-3-carbonitrile (IIIg-13);

4-(4-acryloylpiperazin-1-yl)-2-oxo-1-(2-propoxyethyl)-1,2-dihydroquinoline-3-carbonitrile (IIIg-14);

4-(4-acryloylpiperazin-1-yl)-1-(2-(dimethylamino)ethyl)-2-oxo-1,2-dihydroquinoline-3-carbonitrile (IIIg-15);

1-benzyl-4-(4-(2-chloroacetyl)piperazin-1-yl)-2-oxo-1,2-dihydroquinoline-3carbonitrile (IIIg-16);

1-(2-ethoxyethyl)-2-oxo-4-(4-propioloylpiperazin-1-yl)-1,2-dihydro carbonitrile (IIIg-17); and 4-(4-(2-chloroacetyl)piperazin-1-yl)-1-(4-fluorobenzyl)-2-oxo-1,2-dihydro-1,7-naphthyridine-3-carbonitrile (IIIg-18).

Methods for using MIF inhibitors

In another aspect, methods of treating a disease associated with high MIF expression is provided, which comprises administering to: a subject in need thereof, a therapeutically-effective amount of a MIF inhibitor. In some embodiments, the disease associated with high. MIF expression is selected from Cardiovascular and Cerebrovascular diseases, including but not limited to Atherosclerosis, restenosis of an atherosclerotic coronary artery, Acute coronary syndrome, myocardial infarction, cardiac-allograft vasculopathy, Stroke; Autoimmune Diseases and Inflammatory Disorders, including but not limited to Asthma, chronic obstructive pulmonary disease, Rheumatoid arthritis, Juvenile rheumatoid arthritis, neuropathic pain, Fibromyalgia, Psoriasis, Psoriatic arthritis, colitis, Crohn's disease, ulcerative colitis, Multiple sclerosis, Alzheimer's disease, autoimmune uveitis, Castleman's disease, Ankylosing spondylitis, Pemphigus, Myasthenia gravis, Guillain-Barre syndrome, hepatitis, otitis, experimental allergic neuritis, Autoimmune glomerulonephritis, organ transplant rejection, Sepsis, Shock, spondylitis, systemic lupus erythematosus, lupus nephritis, Diabetes mellitus type 1, Diabetes mellitus type 2, sclerosis, vasculitis, sarcoidosis, pulmonary inflammation, Acute respiratory distress syndrome, wet and dry age-related macular degeneration; Fibrotic diseases; Metabolic disorders, including but not limited Obesity, steroid-resistance, glucose intolerance, metabolic syndrome; and Neoplasia, including but not limited to angiogenesis, multiple myeloma, leukemia, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast, non-small cell lung carcinoma, melanoma, skin cancer, teratoma, rhabdomyosarcoma, glioma, and metastatic bone disease.

Also described are methods: of inhibiting MIF binding to CD74 in a subject which comprises administering to a subject in need thereof, a pharmaceutically effective amount of a MIF inhibitor. In some embodiments, the method of inhibiting MIF binding to CD74 includes preventing, the interaction between MIF with CD74 alone or MIF with CD74 complexed with CD44, CXCR2, CXCR4 and/or other receptors as receptor signaling heterocomplexes.

Also described are methods of inhibiting MIF-induced activation and signal transduction through CD74, CD44, CXCR2, CXCR4 and/or other receptors in a subject which comprises administering to a subject in need thereof a pharmaceutically effective amount of a MIF inhibitor.

Also described are methods of inhibiting the ability of MIF to form a homomultimer or trimer in a subject which comprises administering to a subject in need thereof a pharmaceutically effective amount of a MIF inhibitor.

Also described are methods of inhibiting MIF tautomerase catalytic activity in a subject which comprises administering to a subject in need thereof a pharmaceutically effective amount of a MIF inhibitor.

Also described are methods of inhibiting MIF biological function in a subject which comprises administering to a subject in need thereof a pharmaceutically effective amount of a MIF inhibitor.

Also described are methods of inhibiting MIF expression, production, or secretion in a subject which comprises administering to a subject in need thereof a pharmaceutically effective amount of a MIF inhibitor.

Also described are methods of inhibiting MIF-induced local or systemic inflammatory cell recruitment, infiltration, proliferation or activation; parenchymal cell damage or cellular transformation; or a combination thereof in a subject which comprises administering to a subject in need thereof a pharmaceutically effective amount of a MIF inhibitor.

Also described are methods of inhibiting MIF binding to extracellular and/or intracellular CD74, CXCR2, CXCR4 and/or other targets which comprises contacting a cell with an effective amount of a MIF inhibitor.

Also described are methods of inhibiting MIF binding to soluble receptor forms of CD74, CXCR2, CXCR4 and/or other targets with an effective amount of a MIF inhibitor.

Also described are methods of inhibiting the ability of MIF to form a homomultimer or trimer in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF biological function in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF expression, production, and/or secretion in a cell which comprises contacting a cell with a pharmaceutically effective amount of a MIF inhibitor.

Also described are methods of inhibiting MIF-induced local and/or systemic inflammatory cell recruitment, infiltration, proliferation or activation; parenchymal cell damage or cellular transformation; or a combination thereof which comprises contacting a cell with an effective amount of a MIF inhibitor.

Also provided in the invention is a method for inhibiting, preventing, or treating a disease, or symptoms of a MIF related disease, in a subject Examples of such disorders include, but are not limited to Cardiovascular and Cerebrovascular diseases, Autoimmune Diseases and Inflammatory Disorders, Fibrotic diseases, Metabolic disorders, and Oncologic diseases.

In some embodiments, the subject is administered an effective amount of a MIF inhibitor.

The invention also includes pharmaceutical compositions useful for treating or preventing a MIF associated disease, or for inhibiting a MIF associated disease, or more than one of these activities. The compositions can be suitable for internal use and comprise an effective amount of a MIF inhibitor and a pharmaceutically acceptable carrier. The MIF inhibitors are especially useful in that they demonstrate very low systemic toxicity or no systemic toxicity.

The MIF inhibitors can each be administered in amounts that are sufficient to treat or prevent but are not limited to Cardiovascular and Cerebrovascular diseases, Autoimmune Diseases and Inflammatory Disorders, Fibrotic diseases, Metabolic disorders, and Oncologic diseases or prevent the development thereof in subjects.

Administration of the MIF inhibitors can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as, by way of non-limiting examples, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (non-limiting examples include bolus and infusion), intraperitoneal, intrathecal, intra-vitreal injection, subcutaneous or intramuscular form, all using forms well known to those skilled in the pharmaceutical arts.

Non-limiting illustrative pharmaceutical compositions are tablets and gelatin capsules comprising a MIF inhibitor and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the MIF inhibitor is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the MIF inhibitors.

The MIF inhibitors can be also formulated as a suppository that can be prepared from fatty emulsions or suspensions; using polyalkylene glycols such as propylene glycol, as the carrier.

In further embodiments, the pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The MIF inhibitors can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

MIF inhibitors can also be delivered by the use of monoclonal antibodies as individual carriers to which the MIF inhibitors are coupled. The MIF inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the MIF inhibitors can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, MIF inhibitors are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the MIF inhibitor by weight or volume.

The dosage regimen utilizing the MIF inhibitor is selected in accordance with a variety of factors including type, species, age, weight, sex, race, diet, concomitant medications, and medical condition of the patient; the severity of the condition to be treated; the route of administration; the renal or hepatic function of the patient; and the particular MIF inhibitor employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the MIF inhibitors can be determined as set forth in Goodman, L. S.; Gilman, A. The Pharmacological Basis of Therapeutics, 5th ed.; MacMillan: New York, 1975, pp. 201-226, the contents of which are hereby incorporated by reference.

MIF inhibitors can also be administered in a single daily dose, or the total daily dosage can be administered in divided doses of two, three or four times daily. Furthermore, MIF inhibitors can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the MIF inhibitor ranges from about 0.1% to about 15%, w/w or w/v.

The MIF inhibitors can also each be administered in amounts that are sufficient to treat or prevent MIF-associated diseases. These diseases include, but are not limited to, cardiovascular and cerebrovascular diseases, autoimmune diseases, inflammatory disorders, fibrotic diseases, metabolic disorders, and oncologic diseases either individually or in combination with one or more agents and or methods for treating and preventing these MIF-associated diseases.

Compounds according to the present invention may be administered in combination with the following non-limiting examples of therapeutic agents and methods for treating and preventing these MIF-associated diseases in any combination that may include, but are not limited to any of the following: glucocorticoids, nonsteroidal antiinflammatory drugs (NSAIDs) (non-limiting examples include acetaminophen, aspirin, capsaicin, diclofenac, diclofenac/misoprostol, efenamic acid, etodolac, felbinac, fenoprofen, flurbiprofen, ketoprofen, ibuprofen, indomethacin, ketorolac, loxoprofen, meclofenamate, meloxicam, nabumetone, naproxen, nimesulide, oxaprozin, piroxicam, sulindac, tolmetin), cyclooxygenase (COX)-2 inhibitors (non-limiting examples include celecoxib, valdecoxib, etoricoxib, lumiracoxib, parecoxib), licofelone (ML3000), disease-modifying antirheumatic drugs (DMARDs), methotrexate, chloroquine, hydroxychloroquine, cyclophosphamide (Cytoxan), inosine monophosphate dehydrogenase (IMPDH) inhibitors (a non-limiting example is mycophenolate mofetil [Cellcept, Myfortic]), sirolimus, everolimus (rapamycin), purine nucleoside phosphorylase inhibitors, de novo purine synthesis inhibitors (non-limiting examples include polygentamate derivatives of methotrexate, antifolate compounds), dihydroorotate dehydrogenase inhibitors (malononitrilamides), prostaglandins PGE2 inhibitors, P2X7 receptor inhibitors, proteinase-activated receptor 2 (PAR-2) inhibitors, inhibitors of activated Complement (non-limiting examples include Eculizumab, Pexelizumab), complement C3/C5 convertase inhibitors (a non-limiting example is Nafamostat mesilate), active convertase inhibitors, complement C5aR antagonists, EP4 agonists, prostaglandin-I2 analogs (non-limiting examples include iloprost, cicaprost, treprostinil), Sulphasalazine (SASP), 5-aminosalicylic acid (5-ASA), immunomodulator drugs (non-limiting examples include azathioprine (AZA), 6-mercaptopurine (6-MP), methotrexate (MTX)), calcineurin inhibitors. (non-limiting examples include cyclosporine, voclosporine, tacrolimus), interleukin-10 (AG011), placenta derived cells (PDA001), mucosal addressin cell adhesion molecule (MAdCAM) inhibitors (PF-00547659), GLP-2 agonists (non-limiting examples include ZP1848, ALX-0600), anti-CD3, CCR9 inhibitors, lenalidomide (Revlimid), recombinant human interleukin-11, CXCR2Antagonists (a non-limiting example is SB-656933), glucagon-like peptide-2 (GLP-2) analogue (Teduglutide), insulin-like growth factor-1 (IGF-1) (Increlex), synthetic guanylhydrazone semapimod (CPSI-2364), intracellular adhesion molecule-1 (ICAM-1) inhibitor (alicaforsen), stem cell therapeutics (a non-limiting example is Prochymal), activated protein C (aPC), vitamin D analogs (a non-limiting example is calcipotriene), retinoids (a non-limiting example is tazarotene), phototherapy (non-limiting examples include broadband ultraviolet B light, narrow band ultraviolet B light, psoralen plus ultraviolet A light), methotrexate, cyclosporine, acitretin, CCR6 inhibitors, CCL20 inhibitors, deoxyspergualin, alkylate deoxyribonucleic acid (DNA) agents, tumor necrosis factor (TNF)-alpha inhibitors (non-limiting examples include etanercept, infliximab, adalimumab, certolizumab pegol (Cimzia), golimumab (CNTO-148)), inhibitors of TNF-alpha converting enzyme, Janus kinase (JAK) 1, 2 and/or 3 inhibitors (non-limiting examples include Tofacitinib, INCB-28050, Ruxolitinib), spleen tyrosine kinase (SYK) inhibitors (a non-limiting example is R-788), caspase inhibitor, chemokine receptor antagonists, protein kinase C (pkc) inhibitors (a non-limiting example is Enzastaurin), p38 mitogen-activated protein kinase (MAPK) inhibitors, caspase inhibitors, NF-κB modulators, B cell inhibitors, Hydroxychloroquine, B-lymphocyte stimulator (BLyS) inhibitors (a non-limiting example is belimumab (Benlysta)), membrane-bound and soluble B-cell activating factor inhibitors (a non-limiting example is LY2127399), inhibitors that antagonize the binding of BLyS and APRIL (a proliferation-inducing ligand) cytokines to B cells in order to prevent B-cell maturation and autoantibody production (a non-limiting example is Atacicept), anti-CD19, CD20 inhibitors (non-limiting examples include Rituximab, Ocrelizumab, Ofatumumab), CD22 inhibitors (a non-limiting example is Epratuzumab), T cell inhibitors (non-limiting examples include Alefacept (Amevive), IPP-201101), interferon inhibitors (non-limiting examples include MEDI-545, rontalizumab, fontalizumab), toll-like receptor inhibitors, prasterone, estrogen receptor antagonist (fulvestrant), cytotoxic T-lymphocyte-associated antigen 4 (CTLA-4)-Ig (a non-limiting example is Abatacept (Orencia)), v-set domain containing T cell activation inhibitor 1 (VTCN1; B7-H4) agonists (AMP-110), interleukin-1 receptor antagonists (AMG 108, Anakinra [Kineret]), interleukin-1 beta antagonists (non-limiting examples include canakinumab, Xoma 052), soluble IL-1 receptors (a non-limiting example is rilonacept), interleukin-2R antagonists (non-limiting examples include basiliximab (Simulect), daclizumab (Zenapax), interleukin-6 receptor antagonists (non-limiting examples include Tocilizumab [Actemra]), calcipotriene/betarnethasone (Taclonex), fumarate (Panaclar/BG-12), interleukin-15 inhibitors, interleukin-17 and interleukin-17 receptor inhibitors (non-limiting examples include Secukinumab, Brodalumab, Ixelcizumab, RG7624), retinoic acid receptor-related orphan nuclear receptor [ROR] modulators (non-limiting examples include SR-1001, SR2211), DHODH inhibitors (a non-limiting example is Vidofludimus), interleukin-18 inhibitors, T helper (Th) 17 cell inhibitors, interleukin 12/interleukin 23 inhibitors (non-limiting examples include Ustekinumab [CNTO-1275], briakinumab [ABT 874]), interleukin-22 inhibitors, interleukin-23 inhibitors (a non-limiting example is ustekinumab), interleukin-12 inhibitors (a non-limiting example is ustekinumab), alpha interferons, beta interferons [Interferon beta-1a (Avonex, Rebif), Interferon beta-1b (Betaseron/Betaferon), Glatiramer acetate (Copaxone), selective adhesion molecule inhibitors, integrin antagonists (Natalizumab [Tysabri], vedolizumab), sphingosine 1-phosphate receptor (S1P-R) agonists (a non-limiting example is Fingolimod [FTY720]), fumarate derivative immunomodulators (a non-limiting example is BG-12), laquinimod, anti-LFA-1 (a non-limiting example is Efalizumab [Raptiva]), MBP-8298, cladribin (a non-limiting example is Mylinax), Novantrone, isoxanol dihydroorotate dehydrogenase (DHODH) and tyrosine kinase inhibitor (a non-limiting example is teriflunomide [HMR-1726]), Revimmune (cyclophosphamide), Fampridine SR (4-aminopyridine), Panaclar (dimethylfumarate), MBP8298 (dirucotide, synthetic peptide version of a portion of human myelin basic protein), Campath (alemtuzumab), anti-CD52, Cladribine, purine analogs, Fingolimod (sphingosine 1-phosphate receptor agonists), Laquinimod, Teriflunomide, de novo pyrimidine synthesis inhibitors (non-limiting examples include brequinar, leflunomide [Arava]), active metabolites of leflunomide, photodynamic therapy [PDT] with verteporfin, Anti-angiogenic factors non-limiting examples include vascular endothelial growth factor A (VEGFA) inhibitors (non-limiting examples include pegaptanib sodium, ranibizumab, bevacizumab), CCR3 inhibitors, anti-CD48, beta 2-agonists, leukotriene modifiers, phosphodiesterase (PDE) inhibitors (non-limiting examples include tetomilast, ibudilast), selective phosphodiesterase-4 (PDE-4) inhibitors (non-limiting examples include rolipram, roflumilast, piclamilast, pentoxifylline), inhibitors targeting IgE (Omalizumab), Th2 cytokine inhibitors (non-limiting examples include suplatast tosilate, sIL-4R, IL-5 inhibitors), Macrotides, Ketolide, adenosine A2B antagonists, kappa B kinase 2 inhibitors, prostanoid and F2-isoprostane antagonists, Nitric oxide donors, inducible nitric oxide synthase inhibitors, toll-like receptor modulators, Lorcaserin, phentermine, topiramate, bupropion, naltrexone, Anti-CD3, Antithymocyte globulin, serine protease inhibitors (a non-limiting example is alpha-1 antitrypsin AAT), tyrosine kinase inhibitors, platelet-derived growth factor receptor (PDGFR) inhibitors, insulin, Antigen-Specific Tolerance inducting agents to Type 1 Diabetes (non-limiting examples include Glutamate Decarboxylase 65 and Heat Shock Protein treatments), cannabinoid receptor 1 (CB1) antagonists, long-acting glucagon-like peptide 1 (GLP1) analogues, dipeptidyl peptidase 4 (DPP4) inhibitors, vasoactive intestinal peptide-pituitary adenylate cyclase-activating polypeptide receptor 2 (VPAC2) agonists, Glucokinase activators, Glucagon receptor antagonists, Cytosolic phosphoenolpyruvate carboxykinase (PEPCK) inhibitors, sodium-glucose co-transporter 2 (SGLT2) inhibitors, salsalate, I B kinase-β (IKKβ)-inhibitors, nuclear factor kappa B inhibitors, interleukin-1 (IL-1) receptor antagonists, IL-1 beta-specific antibody, sirtuin 1 (SIRT1) activators, selective peroxisome proliferator-activated receptor (PPAR) modulators (SPPARMs), 11-hydroxysteroid dehydrogenase type 1 (11βHSD1) inhibitors, PPAR ligands (non-limiting examples include rosiglitazone, pioglitazone, troglitazone), thiazolidinediones, glitazones, Warfarin, coumadin, pradaxa (non-limiting examples include dabigatran etexilate mesylate), anti-thrombotics, Statins, hydroxy-methylglutaryl-coenzyme A reductase (HMG-CoA reductase) inhibitors, ezetimibe, fenofibrates, niacin, amlodipine, Vascular cell-adhesion molecule (VCAM) antagonists, Thromboxane A2 antagonists, prostaglandin D2 receptor 1 antagonists, G-protein-coupled receptor (GPCR) modulators, cannabinoid receptor 1 (also known as CNR1) CB1 receptor antagonists (Rimonabant), cholesteryl ester transfer protein (CETP) inhibitors (JTT-705), chemokine (C—C motif) receptor 2 (CCR2) antagonists, Phospholipase A2 inhibitors, peroxisome proliferator-activated receptor (PPAR) agonists, RNA polymerase inhibitors, Leukotriene synthesis inhibitors, α7 nicotinic receptors (α7 nAChRs) agonists, donepezil, galantamine, rivastigmine, memantine, α-secretase cleavage stimulants, -secretase activity inhibitors, antioxidant therapy, estrogens, NO synthetase inhibitors, anti-β-amyloid (Aβ) (bapineuzumab), Abiraterone, ActRIIA signaling inhibitors (ACE-011), adriamycin, aldesleukin [Proleukin], alemtuzumab, alitretinoin, alkylating agents and microtubule inhibitors (non-limiting examples include Taxol, Temozolomide [Temodar]), allopurinol, allosteric Akt inhibitors (Akti) [MK-2206], altretamine, amifostine, anastrozole (Arimidex), triple angiokinase inhibitor that inhibits VEGF receptors (VEGFR) 1, 2, and 3, fibroblast growth factor receptors, and platelet-derived growth factor receptors (BIBF 1120), angiopoietin ½-neutralizing peptibody (AMG 386), anthracycline (amrubicin), antigen-specific cancer immunotherapeutics (ASCI) (non-limiting examples include MAGE-A3, WT1), antimetabolites (Raltitrexed), Apaziquone (EOquin), aprepitant, aromatase inhibitors (non-limiting examples include letrozole [Ferrara], aromasin), arsenic trioxide, Asparaginase, anaplastic lymphoma kinase (ALK) inhibitor (crizotinib, AP26113), azacitidine (Vidaza), BCG Live, Bcl-2 family inhibitors (a on-limiting example is ABT-263), Bcr-Abl inhibitors (non-limiting examples include nilotinib [Tasigna], AP24534), bendatnustine, bexarotene capsules, bexarotene gel, bleomycin, BRAF signaling inhibitors (a non-limiting example is RG7204), busulfan intravenous, busulfan oral, Cabazitaxel (Jevtana), calusterone, capecitabine (Xeloda), carboplatin, carmustine, carmustine with Polifeprosan 20 Implant, caspase inhibitors, anti-CD23, anti-CD30, anti-CD32, anti-CD33, anti-CD40, chlorambucil, cisplatin, cladribine, c-Met receptor tyrosine kinase inhibitors (ARQ197), clofarabine (Clolar), CS1 inhibitors (a non-limiting example is Elotuzumab), cytotoxic T-lymphocyte-associated antigen 4 (CTLA-4) inhibitors (a non-limiting example is ipilimumab), cyclophosphamide, cytarabine, cytarabine liposomal, dacarbazine, dactinomycin, actinomycin D, Darbepoetin alfa (Aranesp), daunorubicin liposomal, daunorubicin, daunomycin, histone deacetylase (HDAC) inhibitors (non-limiting examples include Istodax, LBH589, Belinostat), decitabine (Dacogen), Delta-like 4 ligand (DLL4) inhibitors (OMP-21M18), Denileukin, diftitox, dexrazoxane, docetaxel (Taxotere), doxorubicin, doxorubicin liposomal, Dromostanolone propionate, DR5 agonists (LBY135), Elliott's B Solution, epidermal growth factor receptor (EGFR) inhibitors (non-limiting examples include Cetuximab [Erbitux], GA201, panitumumab [Vectibix]), epidermal growth factor receptor tyrosine kinase (EGFR-TK) inhibitors (a non-limiting example is gefitinib [Iressa]), EGFR inhibitor-protein-tyrosine kinase inhibitors (a non-limiting example is Erlotinib [Tarceva]), dual EGFR/HER2 receptor tyrosine kinase inhibitors (a non-limiting example is Tovok [BIBW-2992]), elsamitrucin, endothelin-B receptor agonists (a non-limiting example is SPI-1620), epirubicin, Epoetin alfa and beta (non-limiting examples include Procrit, Epogen, NeoRecormon), etoposide phosphate, etoposide (VP-16), exemestane, farnesyltransferase inhibitor (FTI) (a non-limiting example is lonafarnib), fentanyl (non-limiting examples include Fentora, Actiq), floxuridine (intraarterial), fludarabine (non-limiting examples include Fludara, Oforta), fluorouracil (5-FU), fulvestrant (Faslodex), G2 checkpoint abrogator (CBP501), GA101, gemcitabine (Gemzar), gerntuzumab ozogamicin, Gonadotropin-Releasing Hormone (GnRH) agonists (a non-limiting example is goserelin [Zoladex]), goserelin acetate, Granulocyte-Colony Stimulating Factor (non-limiting examples include Filgrastim, Pegfilgastrim), granulocyte macrophage-colony stimulating factor (GM-CSF) (Sargramostim), heat shock protein 90 (Hsp90) inhibitors, hedgehog pathway inhibitor (RG3616), Pan-HER inhibitors (PF-00299804), Herceptin, HPV vaccines (non-limiting examples include Gardasil, Cervarix), human death receptor 5 agonists (a non-limiting example is Conatumumab [AMG 655]), hydroxyurea, Ibritumomab (Zevalin), idarubicin, ifosfamide, imatinib mesylate (Gleevec/Glivec), immunomodulatory drugs (IMiDs) (non-limiting examples include Pomalidomide, Thalidomide, lenalidomide), type 1 insulin-like growth factor receptor (IGF-1R) inhibitors (non-limiting examples include figitumumab, AMG-479, Cixutumumab, dalotuzumab), dual kinase inhibitor of both insulin-like growth factor-1 receptor (IGF-1R) and insulin receptor (IR) (OSI-906), interleukin-2, ipilimumab, irinotecan, Istodax (rotnidepsin), lapatinib (Tykerb), leteprinim, leucovorin, levamisole, levoleucovorin, LaddC, lomustine (CCNU), leuprorelin, leutinizing hormone releasing hormone (LHRH) agonists (non-limiting examples include Goserelin, leuprolide, Bicalutamide [Casodex]) and antagonists (a non-limiting example is Ozarelix), lucanthone, MAGE-A3-inhibitors (non-limiting examples include GSK-1572932A, GSK-2132231A), MAPK/ERK kinase ½ inhibitors (AZD6244), meclorethamine (nitrogen mustard), megestrol acetate, melphalan (L-PAM), mercaptopurine (6-MP), mesna, MET inhibitors (XL184), methotrexate, methoxsalen, midostaurin (PKC412), mifamurtide (Mepact), mitomycin C, mitotane, mitoxantrone, mammalian target of rapamycin (mTOR) inhibitors (non-limiting examples include temsirolimus, ridaforolimus, everolimus [Afinitor]), MEK inhibitors (a non-limiting example is GDC-0973/RG7420), microtubule inhibitors (non-limiting examples include ixabepilone [Ixempra]), Microtubule stabilizers (patupilone [EPO906]), multikinase inhibitors (non-limiting examples include sorafenib [Nexavar], Nelarabine, pazopanib [Votrient]), multitargeted receptor tyrosine kinase inhibitors (TKI) (TKI258), nandrolone phenpropionate, Necitumumab, Neulasta, NK-1 receptor inhibitors, Nofetumomab, Noscapine (CB3304), ondansetron, Oprolvekin, oxaliplatin (Eloxatin), PI3K inhibitors (non-limiting examples include GDC-0941/RG7321, BKM120 and BYL719), Dual PI3K/mTOR Inhibitors (BEZ235), paclitaxel (Abraxane), pamidronate, platelet-derived growth factor receptor alpha (PDGFR-α) inhibitors (IMC-3G3), pegademase, Pegaspargase, Pegfilgrastim, pentostatin, pertuzumab, pipobroman, plicamycin, polo-like: kinase 1 (Plk-1) inhibitors, mithramycin, poly (ADP-ribose) polymerase-1 (PARP1) inhibitors (non-limiting examples include MK-4827, Iniparib [BSI-201]), porfimer sodium, integrins avβ3 and avβ5 inhibitors (cilengitide [EMD121974]), Pemetrexed (Alimta), pralatrexate injection (Folotyn), plerixafor (a non-limiting example is Mozobil), dual pro-apoptotic receptor (PARA) DR4 and DR5 agonists (a non-limiting example is recombinant human Apo2L/TRAIL [Dulanermin]), procarbazine, protein-tyrosine kinase inhibitors (a non-limiting example is dasatinib), proteasome inhibitors (a non-limiting example is. Bortezomib [Velcade]), quinacrine, raf and VEGFR inhibitors (a non-limiting example is RAF265), Receptor activator of nuclear factor-κB (RANKL) inhibitors (a non-limiting example is denosumab), Rasburicase, multitargeted receptor tyrosine kinase (RTK)

inhibitor (a non-limiting example is sunitinib [Sutent]), romidepsin (Istodax), Seocalcitol (CB1089), polyethyleneglycol-SN38 conjugates (EZN-2208), Satraplatin, dual Src and Bcr-Abl kinase inhibitors (a non-limiting example is bosutinib), streptozocin, talbuvidine (LDT), talc, tamoxifen (Nolvadex), T-DM1, temozolomide, teniposide (VM-26), testolactone, therapeutic vaccines (BiovaxID, IRX-2, Rindopepimut (CDX-110), sipuleucel-T [Provenge], TVA immunotherapy, Stimuvax [BLP25 liposome vaccine]), somatostatin analogues (a non-limiting example is pasireotide [SOM230]), taxane (Ortataxel), tasisulam, thalidomide [Thalomid], thioguanine (6-TG), thiotepa, topoisomerase I and II inhibitors, topoisomerase I inhibitors (gimatecan [LBQ707], irinotecan), topotecan (Hycamtin), toremifene, Trabectedin (Yonclelis), Trastuzumab, tretinoin (ATRA), Tositumomab (Bexxar), TRPM8 agonists (D-3263), uracil mustard, recombinant urate-oxidase (Elitek), valrubicin, valtorcitabine (monoval LDC), antagonists of vascular endothelial growth factor receptors 1, 2 and 3 ("VEGFR1-3")/platelet-derived growth factor receptor ("PDGFR")/stem cell factor receptor ("c-kit") (motesanib), vascular endothelial growth factor receptor (VEGFR)/epidermal growth factor receptor (EGFR)/rearranged during transfection (RET) tyrosine kinase inhibitors (vandetanib), vascular endothelial growth factor (VEGF) inhibitors (Cediranib, Ramucirumab), VEGFR/EGFR/HER-2 inhibitors (AEE788), vinblastine, vinorelbine, Wnt signaling inhibitors (OMP-18R5), zoledronate, zoledronic acid and combinations thereof, among others.

Methods of Making

Methods for Making the MIF Inhibitors

Examples of synthetic pathways useful for making MIF inhibitors of the present invention are set forth in the Examples below and generalized in herein.

In Scheme 1, each X is either N or C—$R_1$ wherein $R_1$ is independently H, —Cl, —F, —CN, lower alkyl or $CF_3$ with the proviso that no more than two of X are N. Compounds of formulas 1 or 2, $R_2$=H or lower alkyl are known compounds or can be prepared by known methods. Many such compounds are commercially available. Among commercially available compounds of formula 1 are those listed in chart 1. Transformation of compounds of formula I into compounds of formula 2 is readily achieved by treatment with a carbonylating agent, for example, phosgene, carbonyl diimidiazole, or triphosgene. One example of this process is given in Gibbs, A. C., et al., Journal of Medicinal Chemistry 2010 53, 7979. Compounds of formula 2 can be alkylated by treatment with a strong based, for example NaH in the presence of an inert solvent, for example DMF at a suitable temperature, for example, room temperature to provide an anionic species which upon addition a suitable alkylating agent, $R_5$-Lv, wherein —$R_5$ corresponds to $R_5$ of Formula II of the invention and Lv is a leaving group, for example, an iodide, bromide, or a tosyl group, provides a compound of formula 3. Alternatively, alkylation can be performed by treatment of the compound of formula 2 with an alkylating agent in the presence of carbonate base, for example potassium carbonate in a polar, inert solvent, for example DMF, at a suitable temperature, for example room temperature. Such procedures have been described in US 2007/01977547.

Chart 1 Commerically available anthranillic acid derivatives

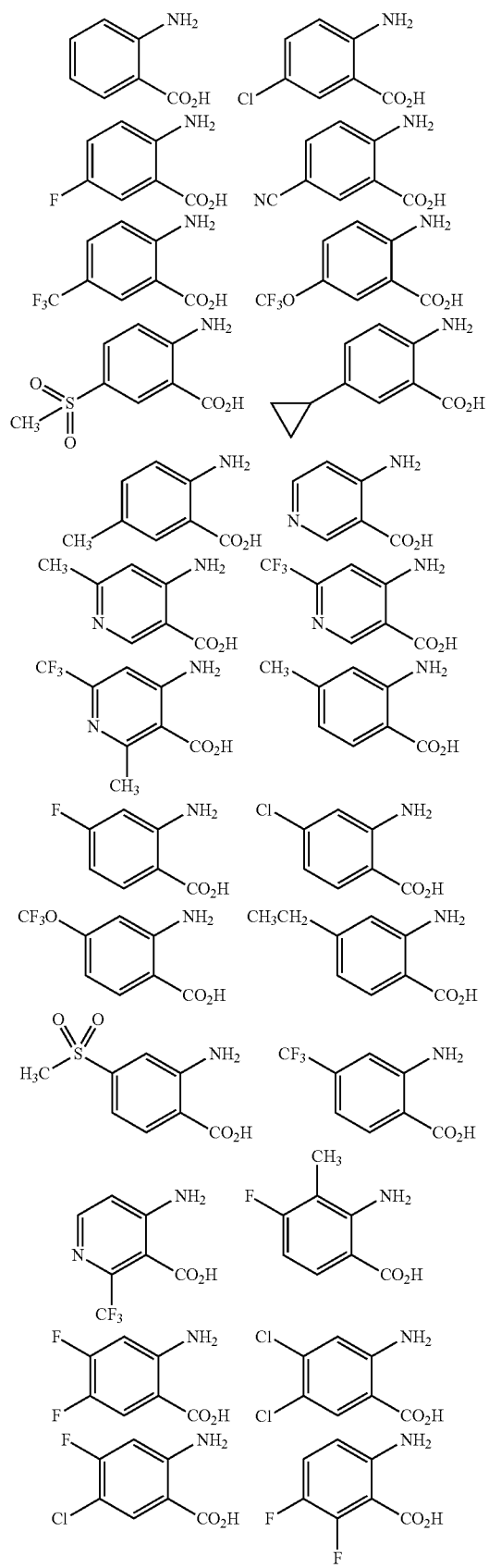

-continued

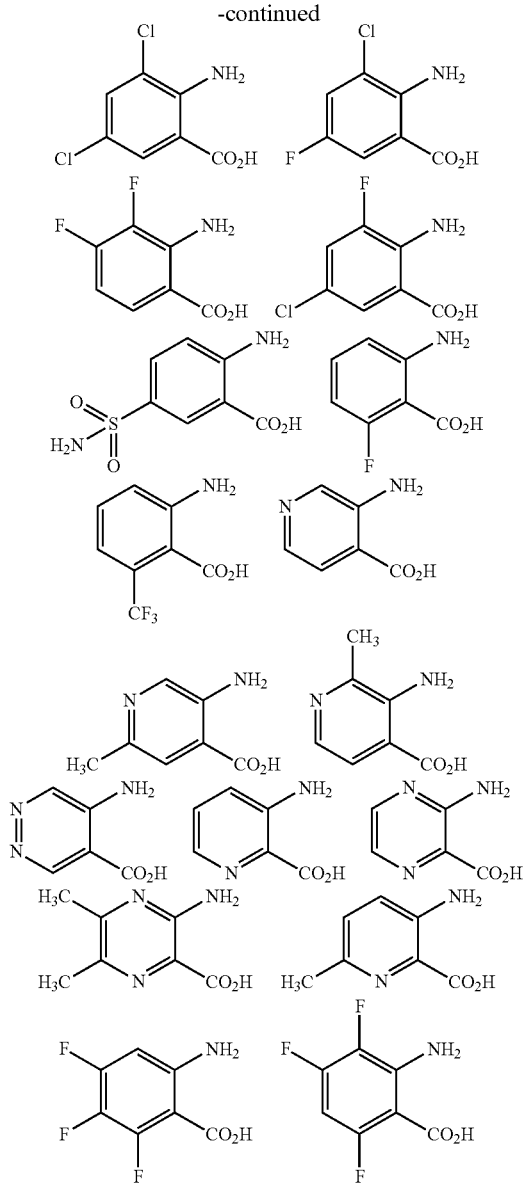

-continued

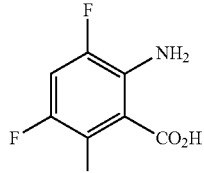

Treatment of compounds of formula 3 with ethyl cyanoacetate in the presence of a base, for example, sodium hydride, in a polar, inert solvent, for example, DMF at a suitable temperature, for example, room temperature, provides a compound of formula 4. Alternatively, in some cases, it may be desirable to initiate the synthesis of 4 starting with an ortho-fluorocarboxylic acid derivative 5. Such compounds are known compounds or can be prepared by known methods. Treatment with a compound of formula 5, $R_2$=lower alkyl, with $R_5$—$NH_2$ in the presence of a high boiling, inert solvent such as DMF at an elevated temperature, for example, 120° C. leads to displacement of the fluoride atom and formation of a compound of formula 6. Compounds of formula 6 can be acylated with an activated derivative of cyanoacetic acid, for example, cyanoacetyl chloride in an inert solvent, for example, methylene chloride at a suitable temperature, for example, room temperature until the reaction is complete. It may be convenient to form cyanoacetyl chloride in situ through the reaction of cyanoacetic acid with oxalyl chloride in methylene chloride in the presence of small quantities of DMF. Cyclization of the thus formed intermediate cyanoacetamide to a compound of formula 4 can be effected by treatment with a mild base, such as potassium carbonate in a polar, solvent, for example DMF at an elevated temperature, for example, 80° C. until the reaction is complete. Compounds of structure 4 are key intermediates in the synthesis of compounds of the invention. Skilled organic chemists will appreciate which route will be the most appropriate for the particular substrate they contemplate and will understand how to modify the reaction conditions to achieve the desired outcome.

Scheme 1

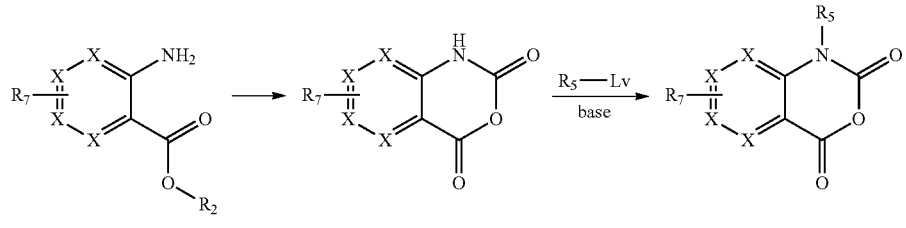

ethyl cyanoacetate
base

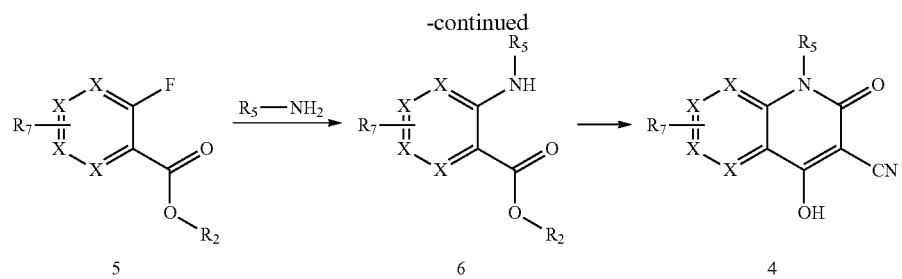

Treatment of 4 with POCl₃ at an elevated temperature, for example around 100° C., leads formation of the chloro derivative 7. In favorable cases, this intermediate can be isolated as a solid by simply dilution with water to precipitate the product, although an extractive workup can also be carded out, if appropriate. When intermediate 7 is reacted with mono-protected diamines of formula 8, (m and n are independently 1 or 2) in the presence of a strong base such as sodium hydride in a: polar aprotic solvent, for example DMF at a suitable temperature, for example, room temperature, a compound of formula 9 is formed. Alternatively, the addition of 7 with the protected diamine 8 can be achieved when the two components are mixed together and heated to elevated temperatures typically in the presence of a tertiary amine base such as triethyl amine or diisopropylethyl amine. For the compounds of formula 8 and 9, PG is a protecting group for the primary amine present. Typically, a Boc group is employed, unless incompatible with other functionality in, the molecule. In that case, a different protecting group may be chosen. Skilled organic chemists will know how to select an appropriate protecting group compatible with the substituents present in the molecule they contemplate. A useful guide to the selection of protecting groups is provided in: Wuts, P. G. M. and Greene, T. W., "Green's Protective Groups in Organic Synthesis, Wiley, 2007.

Removal of the amine protecting group provides the amine substituted intermediate 9. When the protecting group is a tert-butoxycarbonyl moiety, removal can be efficiently effected by treatment with a strong acid. Hydrochloric acid in 1,4-dioxane or trifluoroacetic acid in methylene chloride are commonly used for this process. When hydrochloric acid in 1,4-dioxane is used, the product 10 can often be isolated by concentration of the reaction mixture and addition of diethyl ether to precipitate the product as a hydrochloride salt. Alternatively, an extractive workup may be employed. If a protecting group other than tert-butoxycarbonyl is utilized, appropriate conditions for its removal should be employed and will have been factored into the selection of the protecting group to assure compatibility with other functionality present in the molecule.

Exposure of the amine 10 to activated acid derivatives under standard amide coupling conditions yields the desired compounds of the invention. For example treatment with ethenesulfonyl chloride or ethyne sulfonyl chloride, which are known and commercially available, in the presence of a mild base such as triethylamine or ethyldiisopropyl amine, yields sulfonamides of formulas 11 or 12 respectively.

Scheme 2

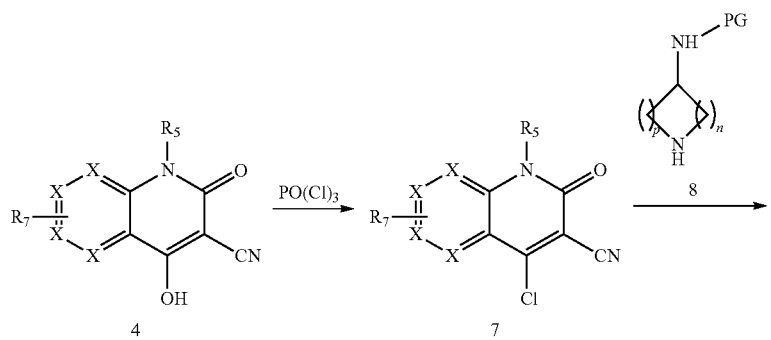

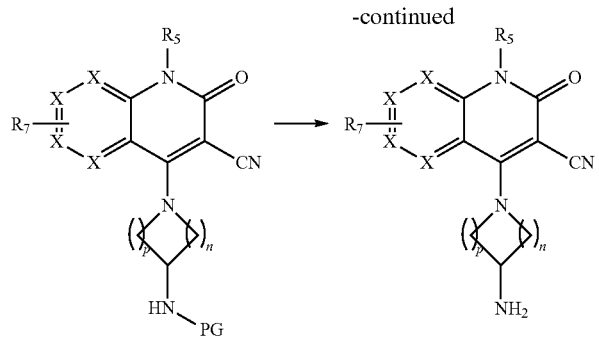

9      10

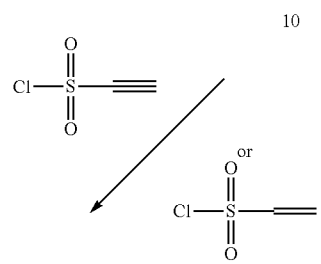

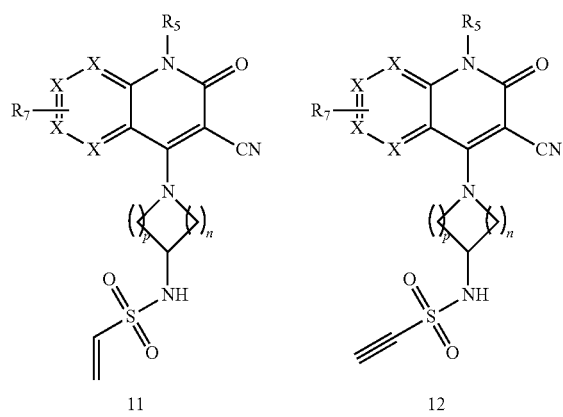

11      12

Using the procedures discussed above and outlined in scheme 2, the following can be synthesized:

N-(1-(3-cyano-1-(4-fluorobenzyl)-2-oxo-1,2-dihydroquinolin-4-yl)piperidin-4-yl)ethenesulfonamide and N-(1-(3-cyano-1-(4-fluorobenzyl)-2-oxo-1,2-dihydroquinolin-4-yl)piperidin-4-yl)ethynesulfonamide As shown in Scheme 3, amines of formula 10 can be reacted with activated acids such as activated forms of acrylic acid. ($R_2$=H or lower alkyl), chloroacetic acid or propiolic acid to give the compounds of the invention 13, 14, and 15 respectively. In these reactions, Lv is a leaving group suitable for acylation reactions and may be either preformed or formed in situ using standard technics for carrying out acylation reactions well known to practicing synthetic organic chemists. Conveniently, Lv may be chloride in which case, the reagents for the preparation of 13 and 14 may be purchased and propynoyl chloride prepared by treatment of propynolic acid with phosphorus pentachloride according to know procedures. See for example: Balfour, W. J. et al., Journal of Organic Chemistry 1974, 39, 725. The acylation reactions may be carried out in an inert solvent, for example, methylene chloride in the presence of a tertiary amine base, for example ethyldiisopropylamine at a suitable temperature, for example, −10° C. initially with the reaction mixture optionally allowed to warm to room temperature as the reaction progresses.

Scheme 3

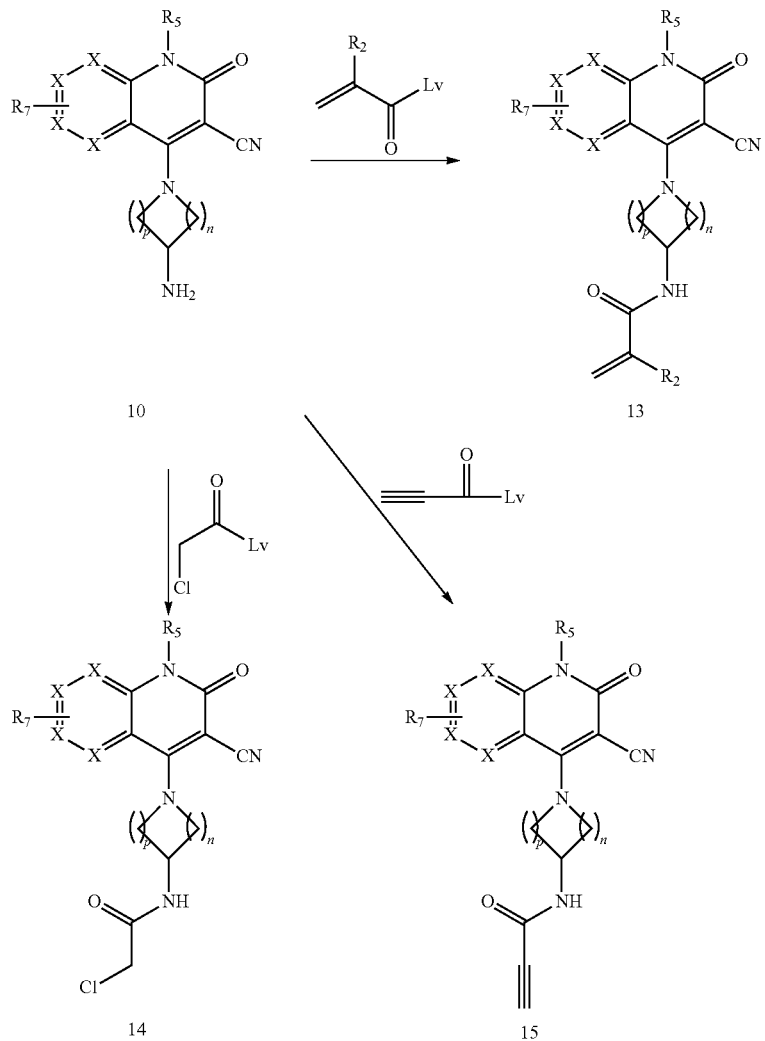

Using the procedures discussed above and outlined in scheme 3, the following can be synthesized:
2-chloro-N-(1-(3-cyano-1-(4-fluorobenzyl)-2-oxo-1,2-dihydroquinolin-4-yl)piperidin-4-yl)acetamide;
2-chloro-N-(1-(3-cyano-1-methyl-2-oxo-1,2-dihydroquinolin-4-yl)piperidin-4-yl)acetamide;
2-chloro-N-(1-(3-cyano-1-methyl-2-oxo-1,2-dihydro-1,6-naphthyridin-4-yl)piperidin-4-yl)acetamide;
2-chloro-N-(1-(3-cyano-1-(2-ethoxyethyl)-2-oxo-1,2-dihydroquinolin-4-yl)piperidin-4-yl)acetamide;
N-(1-(3-cyano-1-(4-fluorobenzyl)-2-oxo-1,2-dihydroquinolin-4-yl)piperidin-4-yl)acrylamide;
N-(1-(3-cyano-1-(4-fluorobenzyl)-2-oxo-1,2-dihydro-1,6-naphthyridin-4-yl)piperidin-4-yl)acrylamide;
N-(1-(3,6-dicyano-1-(4-fluorobenzyl)-2-oxo-1,2-dihydroquinolin-4-yl)piperidin-4-yl)acrylamide;
N-(1-(3-cyano-6-fluoro-1-(4-fluorobenzyl)-2-oxo-1,2-dihydroquinolin-4-yl)piperidin-4-yl)acrylamide;
N-(1-(3-cyano-1-(4-fluorobenzyl)-2-oxo-1,2-dihydroquinolin-4-yl)piperidin-4-yl)propiolamide; and
N-(1-(3-cyano-1-methyl-2-oxo-1,2-dihydroquinolin-4-yl)piperidin-4-yl)propiolamide.

In order to prepare compounds of formulas 19-24, the process shown in Scheme 4 may be employed. Thus, a compound of formula 7 is reacted with mono-protected diamines of formula 16, (m and n are independently 1 or 2) in the presence of a strong base such as sodium hydride in a polar aprotic solvent, for example DMF at a suitable temperature, for example, room temperature, to give a compound of formula 17. Alternatively, the addition of 7 with the protected diamine 16 can be achieved when the two components are mixed together and heated to elevated temperatures typically in the presence of a tertiary amine base such as triethyl amine or diisopropylethyl amine. In the compounds of formula 17 and 18, PG is a protecting group for the secondary amine present. Typically, a Boc group is employed, unless incompatible with other functionality in the molecule. In that case, a different protecting group may be chosen as noted above in the discussion of the synthesis of compound 10.

Removal of the amine protecting group provides the amine of formula 18. When the protecting group is a tert-butoxycarbonyl moiety, removal can be efficiently effected by treatment with a strong acid. Hydrochloric acid in 1,4-dioxane or trifluoroacetic acid in methylene chloride are commonly used for this process. When hydrochloric acid in 1,4-dioxane is used, the reaction can be carried out at room temperature and the product 18 can often be isolated by concentration of the reaction mixture and addition of diethyl ether to precipitate the product as a hydrochloride salt. Alternatively, an extractive workup may be employed. If a protecting group other than tert-butoxycarbonyl is utilized, appropriate conditions for its removal should be employed and these will have been factored into the selection of the protecting group to assure compatibility with other functionality present in the molecule, as discussed above for the preparation of 9.

Exposure of the amine 18 to activated acid derivatives under standard amide coupling conditions yields the desired compounds of the invention. For example dissolution of 18 in an inert solvent, for example, methylene chloride and treatment with ethenesulfonyl chloride or ethyne sulfonyl chloride in the presence of a mild base such as triethylamine or ethyldiisopropyl amine, both of which are known and commercially available, yields sulfonamides of formula 19 or 20 respectively. Conversion of a secondary amine of formula 18 to the amide derivatives 21, 22 and 23, shown in Scheme 4, can be carried out as described above for the conversion of the amine 10 to the amides 13-15.

Scheme 4

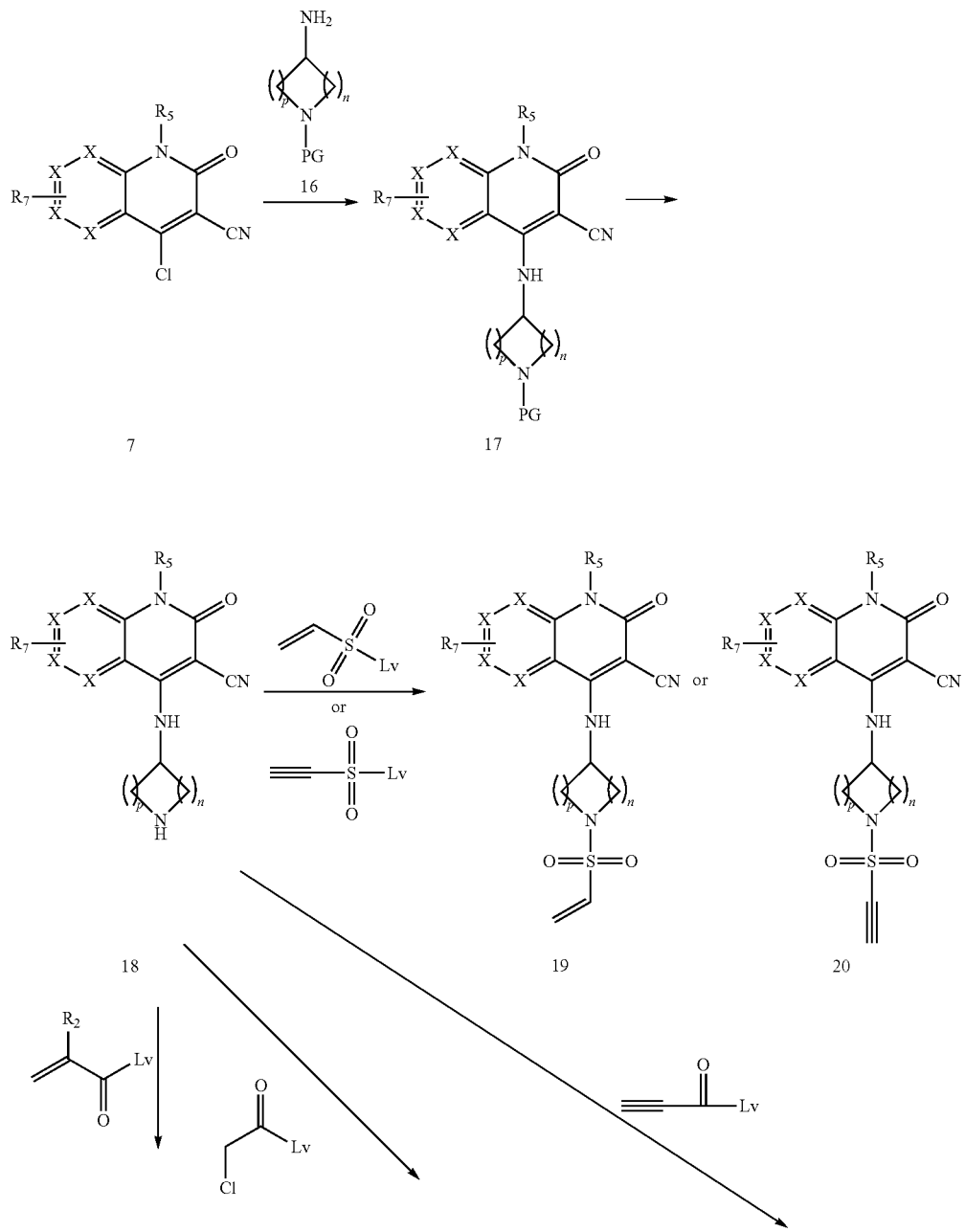

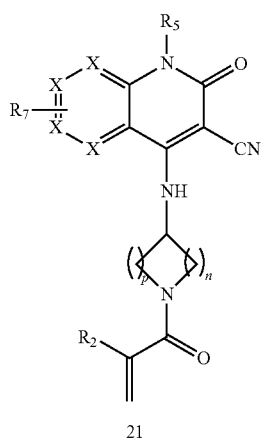
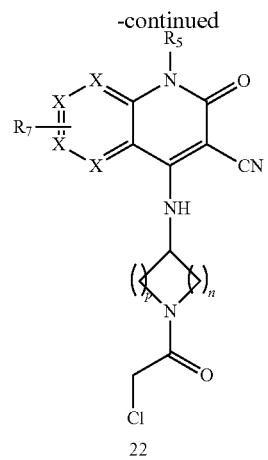
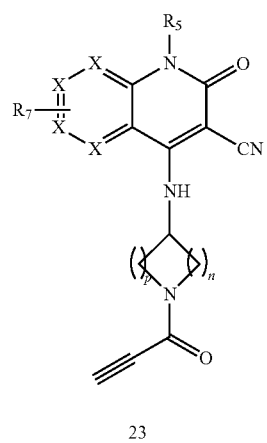

21  22  23

Using the procedures discussed above and outlined in scheme 4, the following can be synthesized:

1-benzyl-4-((1-(2-chloroacetyl)azetidin-3-yl)amino)-2-oxo-1,2-dihydroquinoline-3-carbonitrile;
4-((1-acryloylazetidin-3-yl)amino)-1-(4-fluorobenzyl)-2-oxo-1,2-dihydroquinoline-3-carbonitrile;
1-benzyl-2-oxo-4-((1-propioloylazetidin-3-yl)amino)-1,2-dihydroquinoline-3-carbonitrile;
4-((1-(2-chloroacetyl)azetidin-3-yl)amino)-7-fluoro-1-(3-fluorobenzyl)-2-oxo-1,2-dihydroquinoline-3-carbonitrile;
4-((1-(2-chloroacetyl)azetidin-3-yl)amino)-1-(4-fluorobenzyl)-2-oxo-1,2-dihydro-1,6-naphthyridine-3-carbonitrile;
4-((1-(2-chloroacetyl)azetidin-3-yl)amino)-1-(4-fluorobenzyl)-2-oxo-6-(trifluoromethyl)-1,2-dihydroquinoline-3-carbonitrile
4-((1-(2-chloroacetyl)azetidin-3-yl)amino)-1-(4-chlorobenzyl)-2-oxo-1,2-dihydroquinoline-3-carbonitrile
4-((1-(2-chloroacetyl)azetidin-3-yl)amino)-1-(4-methylbenzyl)-2-oxo-1,2-dihydroquinoline-3-carbonitrile
4-((1-(2-chloroacetyl)azetidin-3-yl)amino)-1-(2-morpholinoethyl)-2-oxo-1,2-dihydroquinoline-3-carbonitrile
4-((1-(2-chloroacetyl)azetidin-3-yl)amino)-1-(2-ethoxyethyl)-7-fluoro-2-oxo-1,2-dihydroquinoline-3-carbonitrile
4-((1-(2-chloroacetyl)azetidin-3-yl)amino)-1-(4-fluorobenzyl)-2-oxo-1,2-dihydro-1,8-naphthyridine-3-carbonitrile
4-((1-(2-chloroacetyl)azetidin-3-yl)amino)-1-(2-ethoxyethyl)-7-fluoro-2-oxo-1,2-dihydroquinoline-3-carbonitrile
4-((1-(2-chloroacetyl)azetidin-3-yl)amino)-1-(2-(dimethylamino)ethyl)-7-fluoro-2-oxo-1,2-dihydroquinoline-3-carbonitrile
4-((1-(2-chloroacetyl)azetidin-3-yl)amino)-1-(4-fluorobenzyl)-2-oxo-6-(trifluoromethyl)-1,2-dihydroquinoline-3-carbonitrile
4-((1-acryloylazetidin-3-yl)amino)-6-fluoro-1-(4-fluorobenzyl)-2-oxo-1,2-dihydroquinoline-3-carbonitrile
4-((1-(2-chloroacetyl)azetidin-3-yl)amino-1-(2-morpholinoethyl)-2-oxo-1,2-dihydroquinoline-3-carbonitrile
4-((1-(2-chloroacetyl)azetidin-3-yl)amino-1-(4-chlorobenzyl)-2-oxo-1,2-dihydroquinoline-3-carbonitrile
4-((1-(2-chloroacetyl)azetidin-3-yl)amino-1-(4-methylbenzyl)-2-oxo-1,2-dihydroquinoline-3-carbonitrile
4-((1-acryloylazetidin-3-yl)amino)-1-(4-fluorobenzyl)-2-oxo-1,2-dihydro-1,5-naphthyridine-3-carbonitrile
4-((1-(2-chloroacetyl)azetidin-3-yl)amino)-1-(4-fluorobenzyl)-2-oxo-1,2-dihydro-1,6-naphthyridine-3-carbonitrile
4-((1-(2-chloroacetyl)azetidin-3-yl)amino)-2-oxo-1-(2-propoxyethyl)-1,2-dihydroquinoline-3-carbonitrile
4-((1-(2-chloroacetyl)azetidin-3-yl)amino)-1-(2-ethoxyethyl)-2-oxo-1,2-dihydroquinoline-3-carbonitrile
4-((1-(2-chloroacetyl)azetidin-3-yl)amino)-1-(4-fluorobenzyl)-2-oxo-1,2-dihydro-1,7-naphthyridine-3-carbonitrile
4-((1-acryloylazetidin-3-yl)amino)-1-(4-fluorobenzyl)-2-oxo-1,2-dihydro-1,7-naphthyridine-3-carbonitrile
4-((1-acryloylazetidin-3-yl)amino)-6-fluoro-1-(4-fluorobenzyl)-2-oxo-1,2-dihydroquinoline-3-carbonitrile
4-((1-acryloylazetidin-3-yl)amino)-1-(4-fluorobenzyl)-2-oxo-1,2-dihydroquinoline-3-carbonitrile
4-((1-acryloylazetidin-3-yl)amino)-1-(4-fluorobenzyl)-2-oxo-1,2-dihydro-1,5-naphthyridine-3-carbonitrile
1-(4-fluorobenzyl)-4-((1-methacryloylazetidin-3-yl)amino-2-oxo-1,2-dihydroquinoline-3-carbonitrile
4-((1-acryloylazetidin-3-yl)amino)-7-chloro-1-(4-fluorobenzyl)-2-oxo-1,2-dihydroquinoline-3-carbonitrile
1-(2-(dimethylamino)ethyl)-2-oxo-4-((1-propioloylazetidin-3-yl)amino)-1,2-dihydroquinoline-3-carbonitrile
1-(4-fluorobenzyl)-2-oxo-4-((1-propioloylazetidin-3-yl)amino)-1,2-dihydroquinoline-3-carbonitrile
1-(2-ethoxyethyl)-2-oxo-4-((1-propioloylazetidin-3-yl)amino)-1,2-dihydroquinoline-3-carbonitrile
1-(4-fluorobenzyl)-2-oxo-4-((1-propioloylazetidin-3-yl)amino)-1,2-dihydro-1,6-naphthyridine-3-carbonitrile
4-((1-(2-chloroacetyl)azetidin-3-yl)amino)-1-(2-ethoxyethyl)-7-fluoro-2-oxo-1,2-dihydroquinoline-3-carbonitrile
4-((1-(2-chloroacetyl)azetidin-3-yl)amino)-1-(3-(dimethylamino)propyl)-6-fluoro-2-oxo-1,2-dihydroquinoline-3-carbonitrile
4-((1-(2-chloroacetyl)azetidin-3-yl)amino)-1-(3-(dimethylamino)propyl)-7-fluoro-2-oxo-1,2-dihydroquinoline-3-carbonitrile The synthesis of epoxides or substituted epoxides of formula 24 (Scheme 5) can be achieved by coupling of a compound of formula 18 with an epoxyacid of formula 26, wherein $R_2$ is H, lower alkyl or phenyl and may be either racemic or enantiomerically pure. Such compounds are commercially available or can be prepared using known procedures. Standard peptide coupling reagents can be employed. One convenient method employs resin bound dicylohexylcarbodiimide (DCC) and 1-hydroxbenzotriazole (HOBt) in THF at room temperature and is described in: Voronkov, M. V., et al., Tetrahedron 2004, 60, 9043. The synthesis of the cyanocyclopropyl derivative 25 may be accomplished by treating an amine of formula 18 with an activated form of commercially available 1-cyanocyclopropane carboxylic acid, 27. One means of achieving activation is conversion to the corresponding acid chloride which can be achieved by treating with reagents suitable for this transformation, for example thionyl chloride under reflux using the procedure described by Lui, X.-H., et al., Bioorganic Medicinal Chemistry Letters 2007, 17, 3784.

4-((1-(1-cyanocyclopropanecarbonyl)azetidin-3-yl)amino)-1-(4-fluorobenzyl)-2-oxo-1,2-dihydroquinoline-3-carbonitrile 4-((1-(1-cyanocyclopropanecarbonyl)piperidin-4-yl)amino)-1-(4-fluorobenzyl)-2-oxo-1,2-dihydroquinoline-3-carbonitrile 1-(2-ethoxyethyl)-4-((1-(oxirane-2-carbonyl)piperidin-4-yl)-amino)-2-oxo-1,2-dihydroquinoline-3-carbonitrile Scheme 5

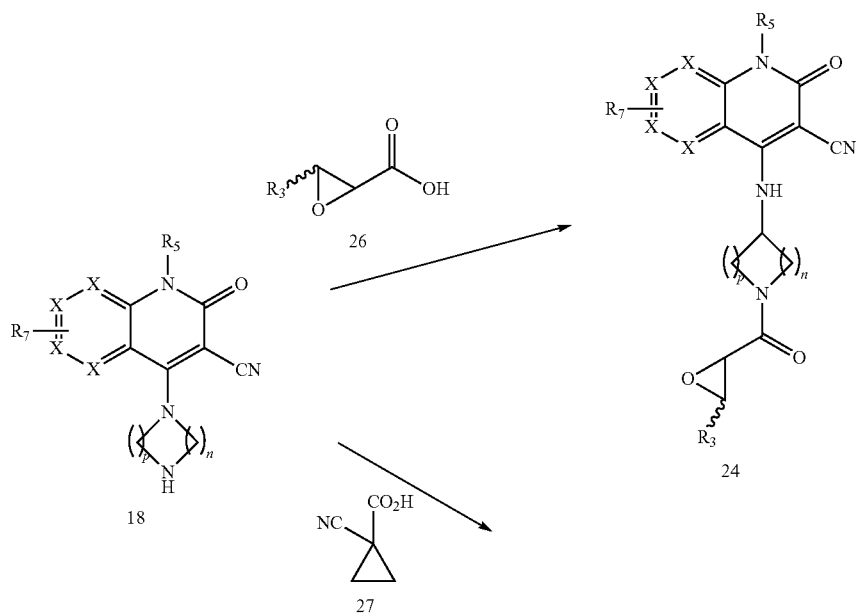

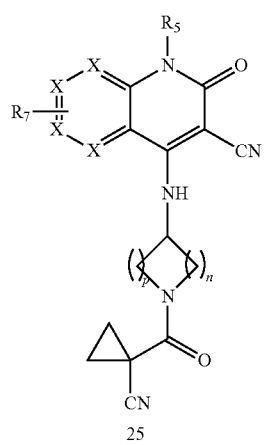

Using the procedures discussed above and outlined in scheme 5, the following can be synthesized:

4-((1-(oxirane-2-carbonyl)azetidin-3-yl)amino-2-oxo-1-(2-propoxyethyl)-1,2-dihydroquinoline-3-carbonitrile 1-(4-fluorobenzyl)-4-((1-(oxirane-2-carbonyl)azetidin-3-yl)amino)-2-oxo-1,2-dihydroquinoline-3-carbonitrile 4-((1-(1-cyanocyclopropanecarbonyl)azetidin-3-yl)amino)-1-(2-ethoxyethyl)-2-oxo-1,2-dihydroquinoline-3-carbonitrile The synthesis of the piperazine derivatives 31-35 can be carried by reaction of a compound of formula 7 with a protected piperazine of formula 28 to give a compound of formula 29, as shown in Scheme 6. The reaction can be carried out under the general reaction conditions employed for the preparation of compounds or formula 9. Removal of the protecting group to give the amine 30 and condensation with the activated acid derivatives shown in Scheme 6 can be carried using the methodology discussed above for the related reactions shown in Schemes 2 and 3.

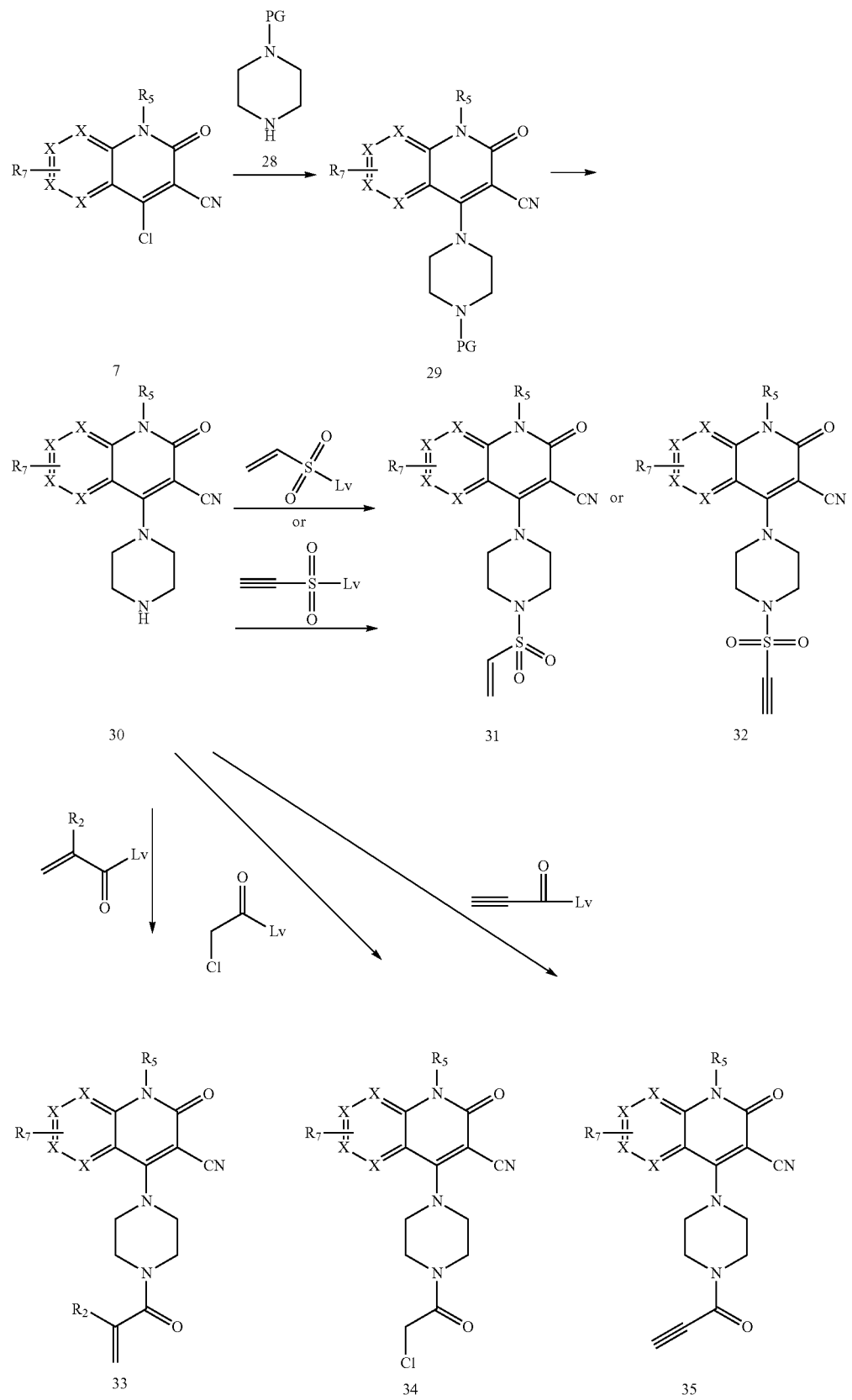

Substituted cycloalkanes 39 and 40 can be prepared as shown in Schemes 7 and 8. When a compound of formula 7 is reacted with primary amines of formula 36, (m and n are independently 1 or 2) in the presence of a strong base such as sodium hydride in a polar aprotic solvent, for example DMF at a suitable temperature, for example, room temperature, a compound of formula 37 is formed. Reaction of compounds of formula 37 with a metalated vinyl derivative, for example, optionally substituted vinyl magnesium bromide or optionally substituted vinyl lithium ($R_2$=H or lower alkyl), 38, in an inert solvent such as diethyl ether or THF at a suitable temperature, for example between −78° C. and 0° C. provides the compound of the invention 39. Similarly, treatment of the compound of formula 37 with an alkynyl magnesium derivative 40 ($R_3$=H or lower alkyl) in an inert solvent, for example THF at a suitable temperature, for example −78° C. provides a compound of formula 41 which is a compound of the invention. Such reactions are well known, for one example, see: Funel, J.-A. and Prunet, J., Journal of Organic Chemistry 2004, 69, 4555.

The preparation of compounds of formula 46 is shown in Scheme 8. A compound of formula 7 can be condensed with , a primary amine of formula 42 (m and n are independently 1 or 2) wherein. PG represents an easily cleavable ester group, for example, a methoxy or tert-butoxy group to give esters of formula 43. Condensation can be carried out using the general procedure described above for the condensation compounds of formula 7 with primary amines of formula 16 shown in Scheme 4. Cleavage of the ester group using mild basic conditions in case a methyl or similar ester is selected, or mild acidic conditions in case an acid sensitive ester such as a tert-butyl ester is selected, will provide an acid of formula 44. Compounds of formula 44 can be converted into the corresponding "Weinreb amides" 37 by coupling with methoxymethyl amine. These condensations have been well characterized in organic chemistry and skilled organic chemists will be able to select suitable conditions compatible with other functionality present in the molecule.

The acid 41 can also be condensed with aminomethyl cyanide, 45, under standard peptide coupling conditions for example in the presence of DCC and HOBt to give the cyanomethyl amides of formula 46.

Using the procedures discussed above and outlined in scheme 4, the following can be synthesized:

4-(4-acryloylpiperazin-1-yl)-1-(2-ethoxyethyl)-2-oxo-1,2-dihydroquinoline-3-carbonitrile 4-(4-acryloylpiperazin-1-yl)-7-fluoro-1-(4-fluorobenzyl)-2-oxo-1,2-dihydroquinoline-3-carbonitrile 4-(4-acryloylpiperazin-1-yl)-2-oxo-1-(2-propoxyethyl)-1,2-dihydroquinoline-3-carbonitrile 4-(4-acryloylpiperazin-1-yl)-1-(2-(dimethylamino)ethyl)-2-oxo-1,2-dihydroquinoline-3-carbonitrile 1-benzyl-4-(4-(2-chloroacetyl)piperazin-1-yl)-2-oxo-1,2-dihydroquinoline-3-carbonitrile 1-(4-fluorobenzyl)-2-oxo-4-(4-(vinylsulfonyl)piperazin-1-yl)-1,2-dihydroquinoline-3-carbonitrile 4-(4-(ethynylsulfonyl)piperazin-1-yl)-1-(4-fluorobenzyl)-2-oxo-1,2-dihydroquinoline-3-carbonitrile 7-chloro-4-(4-(2-chloroacetyl)piperazin-1-yl)-1-(4-fluorobenzyl)-2-oxo-1,2-dihydroquinoline-3-carbonitrile 4-(4-acryloylpiperazin-1-yl)-6-fluoro-1-(4-fluorobenzyl)-2-oxo-1,2-dihydroquinoline-3-carbonitrile 4-(4-acryloylpiperazin-1-yl)-6-chloro-1-(2-(dimethylamino)ethyl)-2-oxo-1,2-dihydroquinoline-3-carbonitrile 4-(4-acryloylpiperazin-1-yl)-1-(4-fluorobenzyl)-2-oxo-1,2-dihydro-1,6-naphthyridine-3-carbonitrile 4-(4-(2-chloroacetyl)piperazin-1-yl)-1-(4-fluorobenzyl)-2-oxo-1,2-dihydro-1,6-naphthyridine-3-carbonitrile 4-(4-(2-chloroacetyl)piperazin-1-yl)-1-(4-fluorobenzyl)-2-oxo-1,2-dihydro-1,7-naphthyridine-3-carbonitrile 1-(2-ethoxyethyl)-2-oxo-4-(4-propioloylpiperazin-1-yl)-1,2-dihydroquinoline-3-carbonitrile 1-(4-fluorobenzyl)-2-oxo-4-(4-propioloylpiperazin-1-yl)-1,2-dihydroquinoline-3-carbonitrile Scheme 7

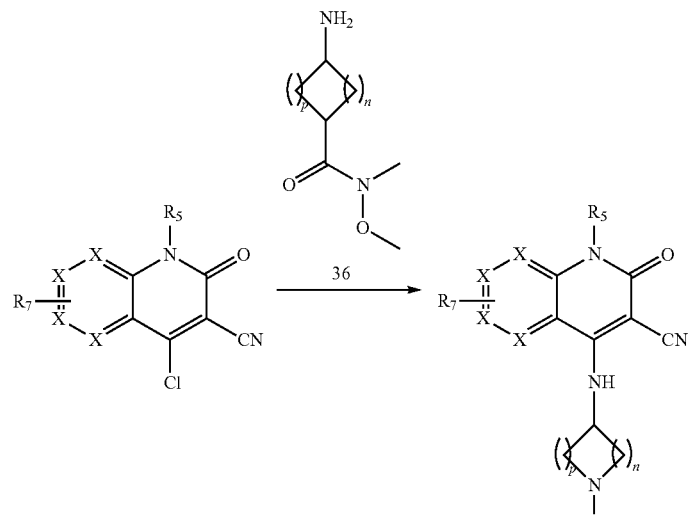

-continued
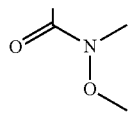
37
7 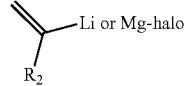
38
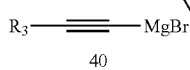
40
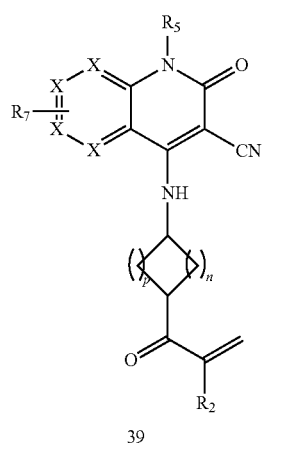
39
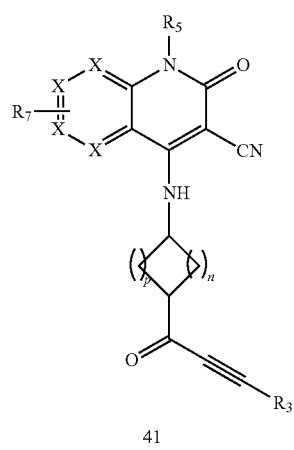
41
Scheme 8
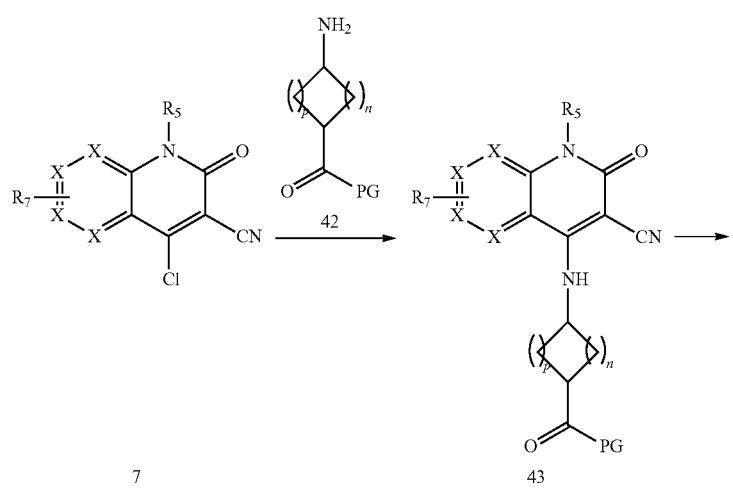
7    43

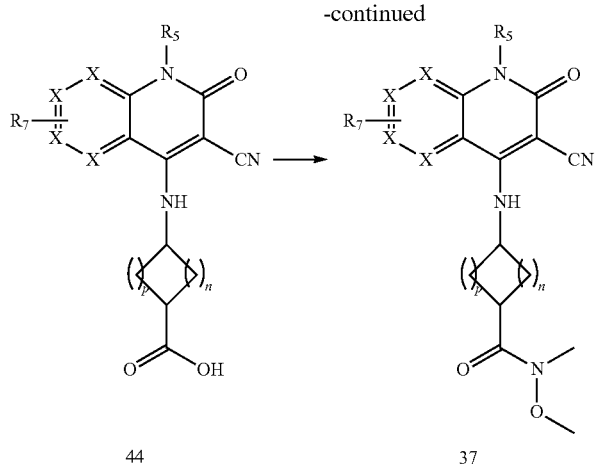

44 → 37

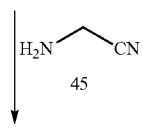
45

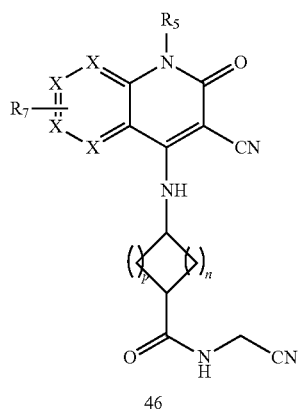
46

Using the procedures discussed above and outlined in schemes 7 and 8, the following can be synthesized:

4-((4-acryloylcyclohexyl)amino)-1-(4-fluorobenzyl)-2-oxo-1,2-dihydroquinoline-3-carbonitrile 4-((4-acryloylcyclohexyl)amino)-1-(4-fluorobenzyl)-2-oxo-1,2-dihydro-1,6-naphthyridine-3-carbonitrile 1-(4-fluorobenzyl)-2-oxo-4-((4-propioloylcyclohexyl)amino)-1,2-dihydroquinoline-3-carbonitrile 4-((4-acryloylcyclohexyl)amino)-6-fluoro-1-(4-fluorobenzyl)-2-oxo-1,2-dihydroquinoline-3-carbonitrile 4-((4-acryloylcyclohexyl)amino)-1-(4-fluorobenzyl)-2-oxo-1,2-dihydro-1,7-naphthyridine-3-carbonitrile 4-((4-acryloylcyclohexyl)amino)-1-(2-ethoxyethyl)-2-oxo-1,2-dihydro-1,7-naphthyridine-3-carbonitrile 4-((4-acryloylcyclohexyl)amino)-1-(3-(dimethylamino)propyl)-2-oxo-1,2-dihydroquinoline-3-carbonitrile N-cyano-4-((3-cyano-1-(4-fluorobenzyl)-2-oxo-1,2-dihydroquinolin-4-yl)amino)cyclohexanecarboxamide 3-((3-cyano-2-oxo-1-(2-propoxyethyl)-1,2-dihydroquinolin-4-yl)amino)-N-(cyanomethyl)cyclobutanecarboxamide 4-((3-acryloylcyclobutyl)amino)-2-oxo-1-(2-propoxyethyl)-1,2-dihydroquinoline-3-carbonitrile 4-((3-acryloylcyclobutyl)amino)-1-(4-fluorobenzyl)-2-oxo-1,2-dihydroquinoline-3-carbonitrile 4-((3-acryloyl cyclobutyl)amino)-1-(4-fluorobenzyl)-2-oxo-1,2-dihydro-1,6-naphthyridine-3-carbonitrile 6-fluoro-1-(4-fluorobenzyl)-2-oxo-4-((3-propioloylcyclobutyl)amino)-1,2-dihydroquinoline-3-carbonitrile 1-(4-fluorobenzyl)-2-oxo-4-((3-propioloylcyclobutyl)amino)-1,2-dihydroquinoline-3-carbonitrile 4-((3-acryloylcyclobutyl)amino)-7-fluoro-1-(4-fluorobenzyl)-2-oxo-1,2-dihydroquinoline-3-carbonitrile 4-((3-acryloylcyclobutyl)amino)-1-(4-fluorobenzyl)-2-oxo-1,2-dihydro-1,7-naphthyridine-3-carbonitrile 4-((3-acryloylcyclobutyl)amino)-1-(3-(dimethylamino)propyl)-2-oxo-1,2-dihydroquinoline-3-carbonitrile Scheme 9
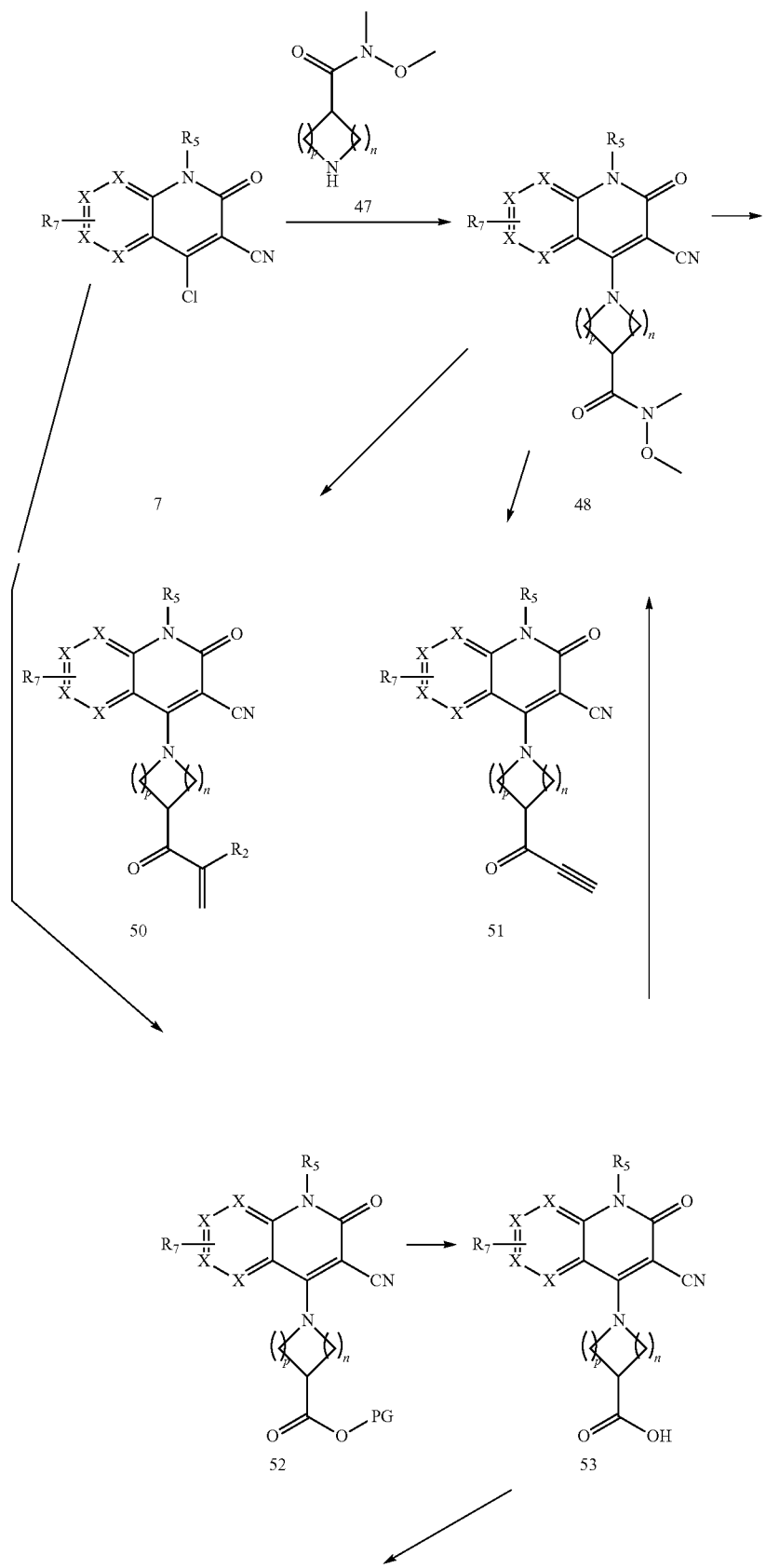

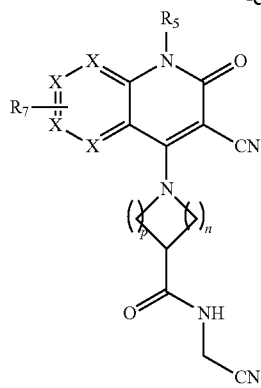

54

Compounds of formulas 52-54 can be prepared as shown in scheme 9 using the methodologies described in the discussion of schemes 7 and 8.

Using the procedures discussed above and outlined in schemes 7 and 8, the following can be synthesized:

1-(3-cyano-1-(4-fluorobenzyl)-2-oxo-1,2-dihydroquinolin-4-yl)-N-(cyanomethyl)azetidine-3-carboxamide
1-(3-cyano-1-(2-ethoxyethyl)-2-oxo-1,2-dihydroquinolin-4-yl)-N-(cyanomethyl)azetidine-3-carboxamide
1-(3-cyano-1-(4-fluorobenzyl)-2-oxo-1,2-dihydroquinolin-4-yl)-N-(cyanomethyl)piperidine-4-carboxamide
1-(4-fluorobenzyl)-2-oxo-4-(3-propioloylazetidin-1-yl)-1,2-dihydro-1,6-naphthyridine-3-carbonitrile
1-(4-fluorobenzyl)-2-oxo-4-(3-propioloylazetidin-1-yl)-1,2-dihydroquinoline-3-carbonitrile
4-(3-acryloylazetidin-1-yl)-1-(4-fluorobenzyl)-2-oxo-1,2-dihydroquinoline-3-carbonitrile
4-(3-acryloylazetidin-1-yl)-1-(4-fluorobenzyl)-2-oxo-1,2-dihydro-1,6-naphthyridine-3-carbonitrile
4-(4-acryloylpiperidin-1-yl)-1-(4-fluorobenzyl)-2-oxo-1,2-dihydroquinoline-3-carbonitrile
4-(4-acryloylpiperidin-1-yl)-1-(4-fluorobenzyl)-2-oxo-1,2-dihydro-1,6-naphthyridine-3-carbonitrile
4-(4-acryloylpiperidin-1-yl)-1-(4-fluorobenzyl)-2-oxo-1,2-dihydro-1,7-naphthyridine-3-carbonitrile
4-(4-acryloylpiperidin-1-yl)-7-fluoro-1-(4-fluorobenzyl)-2-oxo-1,2-dihydroquinoline-3-carbonitrile
4-(4-acryloylpiperidin-1-yl)-6-fluoro-1-(4-fluorobenzyl)-2-oxo-1,2-dihydroquinoline-3-carbonitrile
4-(3-acryloylazetidin-1-yl)-6-fluoro-1-(4-fluorobenzyl)-2-oxo-1,2-dihydroquinoline-3-carbonitrile
4-(4-acryloylpiperidin-1-yl)-1-(2-ethoxyethyl)-2-oxo-1,2-dihydroquinoline-3-carbonitrile
4-(4-acryloylpiperidin-1-yl)-1-(3-(dimethylamino)propyl)-2-oxo-1,2-dihydroquinoline-3-carbonitrile
4-(3-acryloylazetidin-1-yl)-6-chloro-1-(4-fluorobenzyl)-2-oxo-1,2-dihydroquinoline-3-carbonitrile
4-(3-acryloylazetidin-1-yl)-7-fluoro-1-(4-fluorobenzyl)-2-oxo-1,2-dihydroquinoline-3-carbonitrile

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The methodologies described herein and below are designed to (1) quantitate and describe the nature of the physical interaction between MIF and candidate compounds, (2) determine the biological consequence resulting from the interaction of MIF with the candidate compound, (3) evaluate the impact of the candidate compound in animal models of MIF mediated disease.

Example A

Tautomerase Activity

Native human MIF exhibits the ability to catalyze a tautomerase reaction, the physiological importance of which remains controversial. The ability of candidate compounds to inhibit this tautomerase activity is quantitated by wing hydroxyphenyl pyruvic acid (HPP) as a substrate and following the increase in absorbance due to the enzymatic formation of the HPP enol-borate complex at 300 nm in the absence and presence of a test compound. The $IC_{50}$ value of compounds was determined by plotting the initial velocities determined at 300 nm as a function of a test compound's concentration. Assays were carried out in a 96 or 384 well plate format.

Representative MIF inhibitors were tested in the assay described above and the results tabulated in Table 1 wherein "A" represents ≤1 µM; "B" represents >1 µM and ≤100 µM; "C" represents >100 µM

| Compound | Tautomerase $IC_{50}$ [uM] |
| --- | --- |
| 2 | B |
| 4 | C |
| 1 | B |
| 3 | C |
| 5 | A |
| 6 | A |
| 7 | A |
| 8 | A |

-continued

| Compound | Tautomerase IC$_{50}$ [uM] |
|---|---|
| 5 | |
| 6 | |
| 8 | |

Example B

Interaction of Candidate Compound with MIF

Direct binding of candidate compounds with MIF are quantitated using surface plasmon resonance (Biacore analysis), a technique that measures biomolecular interactions through refractive index changes on a biospecific chip surface. For these experiments, recombinant human MIF (rhMIF) expressed with an amino terminal biotin tag is immobilized on a streptavidin bioactive surface. The candidate compound is passed over the chip surface at various concentrations and binding quantitated in a time and concentration dependent manner. Association (k+1) and dissociation (k−1) rate constants as well as equilibrium dissociation constants (KD) are generated on each candidate compound.

Example C

MIF:CD74 Binding Inhibitory Activity

The productive interaction between MIF and its receptors has been demonstrated to be critical for the initiation of MIF biological activity. CD74 represents one of the key receptors for MIF that is expressed on, the cell surface of immune cells including macrophages. The interaction between CD74 and MIF is quantitated using surface plasmon resonance (Biacore analysis), a technique that measures biomolecular interactions through refractive index changes on a biospecific chip surface. The extracellular domain of recombinant human CD74 (residues 73-232) expressed with a biotin tag is immobilized on a streptavidin bioactive surface. rhMIF is passed over the immobilized CD74 at various concentrations and the binding affinity of the CD74:MIF interaction in the absence of compound determined. The ability of compounds to block the MIF:CD74 complex is examined by co-injecting a mixture of MIF and varied concentrations of compound over immobilized CD74. The IC$_{50}$ for compounds are determined by plotting the decrease in the maximal refractive index in the absence of compound versus the concentration of compound. Control experiments are carried out to establish that compounds are not binding to CD74 directly.

Example D

MIF:CXCR2 and CXCR4 Binding Inhibitory Activity

Cold competition radioligand binding studies are utilized to quantitate the MIF:CXCR4 binding inhibitory activity of candidate compounds. The ability of unlabeled rhMIF to compete with $^{125}$I-CXCL12 (the cognate CXCR4 ligand) binding to Jurkat T cells endogenously expressing CXCR4 will be quantitated in a concentration dependent manner and the inhibitory constant for this interaction (Ki) determined. Candidate compound modulation of this binding is determined following 30 minutes of preincubation with MIF. The impact of candidate compounds on the potency of MIF competing with tracer CXCL12 binding to CXCR4 on Jurkat cells is quantitated in a concentration dependent manner using assay conditions that take into account the multiple equilibria present in the reaction. Control experiments are carried out to establish that candidate compounds are not binding to CXCR4.

A similar approach is used to evaluate the effect of candidate compounds on MIF:CXCR2 binding. In this example, radioligand binding studies quantitating the affinity (Ki) of unlabeled rhMIF to compete with tracer levels of $^{125}$I-CXCL8 (the cognate CXCR2 ligand) for binding to human CXCR2 ectopically expressed on the surface of HEK293 cells will be studied. Candidate compound modulation of this binding is determined following a preincubation with MIF. The impact of candidate compounds on the potency of MIF competing with tracer CXCL8 binding to CXCR2 will be quantitated in a concentration dependent manner using assay conditions that take into account the multiple equilibria present in the reaction.

Example E

Effect of Candidate Compounds on Cytokine Production from Human Cells

MIF is secreted by monocytes/macrophages, activated T cells and several effector cells that play an important role in the perpetuation of inflammatory responses of the disease pathogenesis of several autoimmune and inflammatory disorders. MIF promotes the production of proinflammatory mediators such as tumor necrosis factor-α (TNF-α), interleukin (IL)-1β, IL-6 and IL-8 acting in an autocrine and paracrine function in the induction of proinflammatory responses. MIF has also been reported to stimulate the production of IL-17, a T helper 17 (Th17)-specific cytokine critical to the pathogenesis of several autoimmune and inflammatory diseases. The benefits of neutralizing MIF have demonstrated preclinical efficacy in animal models of several autoimmune and inflammatory diseases which are associated with down-regulated inflammatory responses and inhibition of cytokine production in these disease models. Mono-Mac-6 Cells: The cellular efficacy of compound candidates is determined using the human monocytic cell line, Mono-Mac-6 cells (MM6 cells) as it has been shown that MM6 cells abundantly express MIF receptors CD74 and CXCR4. MIF-mediated signal transduction through these receptors may be important for the production of inflammatory mediators, including TNF-α, IL-1β, IL-6, IL-8, interferon-γ (IFN-γ) and prostaglandin E2 (PGE2) in these cells. To induce the production of inflammatory mediators, MM6 cells will be plated at a final concentration of $5 \times 10^5$ cells/ml in RPMI 1640 medium containing 1% heat-inactivated low-pyrogen fetal bovine serum, 2 mM GlutaMAX-I, 1% non-essential amino acids, 1% sodium pyruvate, 100 units/ml penicillin G and 100 μg/ml streptomycin (Gibco BRL Life Technologies). Cells will be stimulated with 100 ng/ml rhMIF purchased commercially or generated in house with or without inhibitor for 20 h at 37° C. with 5% CO2. The supernatants are stored at 20° C. until they are to be assayed. The levels of inflammatory mediators will be determined using commercial :ELISA kits (eBiosciences). Human Peripheral Blood Mononuclear Cells (PBMCs): The cellular efficacy of compound candidates in inhibiting the production of proinflammatory mediators TNF-α, IL-1β, IL-6 and IL-8 following lipopolysaccharide (LPS) and rhMIF stimulation, and the production of T helper 17 (Th17)-specific cytokines IL-17F and IL-22 following anti-CD3/anti-CD28 stimulation, are determined in human PBMCs. To induce the production of proinflammatory cytokine mediators, cryopreserved human PBMCs (Cellular Technology Ltd.) are plated at a final concentration of $2 \times 10^5$ cells/ml in RPMI 1640 medium containing 1% heat-inactivated fetal bovine serum, 1% L-Glutamine and 1% Penicillin/Streptomycin (Lonza). Cells are pre-incubated with or without inhibitor compounds dissolved in DMSO for 1 hour, then stimulated with LPS (Sigma Aldrich) or rhMIF to yield final concentrations of <0.1% DMSO, 100 ng/ml LPS and the compound concentration of interest. The potency of the compound candidates in inhibiting cytokine production is compared, to other small molecule MIF inhibitor standards ISO-1 (EMD Chemicals) N-acetyl-p-benzoquinone imine (NAPQI) and Ibudilast (TCI America). Cells were incubated for 20 hours at 37° C., 5% $CO_2$. For the Th17-specific cytokine production assay, cells are stimulated with 5 ug/mL plate immobilized anti-CD3 (eBioscience) and 2 ug/mL soluble anti-CD28 (eBioscience) in the presence or absence of inhibitor compounds dissolved in DMSO to yield final compound concentrations of interest at <0.1% DMSO. Cells were incubated for 72 hours at 37° C. and 5% $CO_2$. The supernatants are stored at −20° C. until they are to be assayed by ELISA. Cell viability is determined using PrestoBlue™ Cell Viability Reagent (Invitrogen). The cytokine production levels of TNF-α, IL-1β, IL-6, IL-8, IL-17F and IL-22 are determined using commercial ELISA kits (eBiosciences). Human Rheumatoid Arthritis Synovial Fibroblast (RASF) Cell Line: RASF cells are cultured in Dulbecco's modified Eagle's medium with 15% FBS, 1% glutamine, and 1% penicillin/streptamycin (all from Gibco (Invitrogen), Gaithersburg, Md.). Experiments are performed with cells between passages 7 to 10, using trypsin with 0.25% ethylene diamine tetraacetic acid (EDTA) (Gibco) to detach cells. IL-1 or MIF are pre-incubated for 15 minutes with compounds dissolved in dimethyl sulfoxide (DMSO). The mixtures are then added to cells to yield final concentrations of 1% DMSO, 1 ng/ml IL-1 or 1 ug/ml MIF. RASFs are incubated with or without stimuli at 37° C. for 20 h then culture supernatants were assessed for IL-6 production by ELISA.

Representative MIF inhibitor compound candidates and control standards were tested in the assay described above, specifically, human PBMCs were stimulated with either LPS or anti-CD3/anti-CD28. Representative MIF inhibitor compound candidates and control standards were preincubated at a final concentration of 25 uM and 2.5 uM for 1 hour prior to LPS-stimulation and inhibition of IL-1β, IL-6, IL-8 and TNF-α production was determined at 20 hours. Additionally, representative MIF inhibitor compound candidates were pre-incubated at a final concentration of 2.5 uM at time of anti-CD3/anti-CD28 stimulation and inhibition of IL-17F and IL-22 production was determined after 72 hours. The results are tabulated in Tables 2a, 2b and 2c below wherein "D" represents ≤10% inhibition; "E" represents >10% inhibition and ≤50% inhibition; and "F" represents >50% inhibition and ≤70% inhibition; and "G" represents >70% inhibition.

Table 2a shows percent Inhibition of proinflammatory cytokine (IL-1β, IL-6, IL-8 and TNF-α) production [LPS-stimulated PBMCs] by compound candidates and MIF-inhibitor standards at 25 uM (ISO-1 at 50 uM):

| Compound [25 uM] | IL-1β | IL-6 | IL-8 | TNF-α |
|---|---|---|---|---|
| 2 | G | D | D | G |
| 4 | F | D | D | E |
| 1 | G | G | F | G |
| 3 | E | D | D | E |
| 5 | G | D | D | F |
| 6 | E | E | D | E |
| 7 | G | D | D | G |
| 8 | G | E | D | E |
| ISO-1 | G | F | E | G |
| Ibudilast | G | D | D | G |
| NAPQI | G | D | D | G |

Table 2b shows percent inhibition of proinflammatory cytokine (IL-1β, IL-6, IL-8 and TNF-α) production [LPS-stimulated PBMCs] by compound candidates and MIF-inhibitor standards at 2.5 uM (ISO-1 at 5.0 uM)

| Compound | IL-1β | IL-6 | IL-8 | TNF-α |
|---|---|---|---|---|
| 2 | G | D | D | E |
| 4 | E | E | D | D |
| 1 | G | E | E | E |
| 3 | F | D | D | D |
| 5 | F | E | D | E |
| 6 | E | E | D | E |
| 7 | F | E | D | E |

-continued

| Compound | IL-1β | IL-6 | IL-8 | TNF-α |
|---|---|---|---|---|
| 8 | F | D | D | E |
| ISO-1 | F | D | D | E |
| Ibudilast | F | D | D | G |
| NAPQI | E | D | D | D |

Table 2c. shows percent inhibition of Th17-specific cytokine (IL-17F, IL-22) production [anti-CD3/anti-CD28-stimulated PBMCs] by compound candidates at 2.5 uM

| Compound | IL-17F | IL-22 |
|---|---|---|
| 2 | G | E |
| 1 | G | G |

There was no direct correlation observed between the compound candidates' potency on enzyme tautomerase activity inhibition (Table 1) and the ability of candidate compounds to inhibit cellular cytokine production in vitro (Tables 2a, 2b). Compound candidates demonstrate more potent cytokine inhibitory properties compared to other small molecule MIF inhibitors. ISO-1, NAPQI and Ibudilast. Inhibition of LPS-induced PBMC production of IL-1β and TNF-α was seen by compounds designed to be reversible and irreversible inhibitors irrespective of its' $IC_{50}$ potency on tautomerase inhibition. These experimental results are in line with scientific data reporting that inhibition of MIF tautomerase activity is not tantamount to complete inhibition of MIF biological properties. The irreversible inhibitor Compound 1, however, demonstrates a more complete cytokine inhibitory profile with consistently more pronounced and concomitant inhibition of the additional proinflammatory cytokines IL-6 and IL-8 in addition to TNF-α, and IL-1β, and of the Th17-specific cytokines IL-17F and IL-22. The unique anti-inflammatory properties of particular compounds such as Compound 2 implicate the biological implications of covalent binding of small molecule MIF inhibitor compounds to pharmacophoric sites beyond the enzyme tautomerase site that may impact cytokine signal transduction through MIF receptors.

Example F

Absence of Cellular Toxicity

No significant cellular toxicity was observed using the PrestoBlue™ cell viability assay for either compound candidates tested or comparator standards at all concentrations tested that demonstrate cytokine inhibition, thereby providing evidence for mechanistic specificity versus overt toxicity responsible for cytokine regulation.

Example G

Evaluation of Time Dependence in the MIF Tautomerase Activity Assay

The MIF tautomerase and cytokine inhibitor Compound 1 was designed as a potential irreversible inhibitor of MIF tautomerase activity. In an effort to investigate this mechanism, time dependent inhibitor analysis was carried out. In this experiment MIF was preincubated [P.I.] with Compound 1 for either 0 minutes, 20 minutes or 60 minutes followed by tautomerase enzyme activity determination. Time dependent inhibition was noted with a progressive left shift in $IC_{50}$ potency as a function of preincubation time from 24 uM (0 minutes, no preincubation [P.I.]) to 6 uM (20 minutes P.I.) and 3 uM (60 minutes P.I.). This time dependent inhibition is indicative of irreversible or slowly reversible inhibitory mechanisms and the left shift is highly suggestive of slow/tight (covalent) binding.

FIG. 1 shows that the potency of Compound 1 left-shifted as a function of time from $IC_{50}$=24 uM to $IC_{50}$=3 uM, confirming time-dependence. Compound 1 was preincubated with MIF as indicated (0 min-60 min) and, a tautomerase dose-response analysis was carried out.

Example H

Distinguishing Reversible from Irreversible Inhibition of MIF-inhibitor Dilution. Irreversible Inhibitors are Typically Time-dependent As described above, to determine time-dependence, initial velocities are measured as a function of pre-incubation time. Assuming the enzyme concentration is significantly less than the inhibitor concentrations being employed, an approximate first-order decay of activity with time will suggest a time-dependent inhibitor. Such a time-dependent inhibitor can interact either reversibly or irreversibly with the enzyme. Functional irreversibility can be demonstrated by pre-incubating enzyme with excess inhibitor, diluting to an inhibitor concentration significantly below the $IC_{50}$, and measuring the resulting activity compared to that given by the same final concentrations of enzyme and inhibitor, but without pre-incubation. If the pre-incubated sample maintains a lower activity, this suggests functional irreversibility.

Example I

Determination of Inhibitor MIF Enzyme Covalent Adduct Formation

Because very tight-binding, reversible interactions can appear functionally irreversible, the presence of a covalent bond between inhibitor and enzyme should be confirmed by a physical method. This is particularly important if there is some question about the inhibitor's ability to form such an adduct. A covalent linkage between inhibitor and enzyme can often be verified by mass spectrometry of the intact protein compared with inhibitor-treated enzyme. If this is not possible, comparison of reversed-phase HPLC elution profiles of tryptic peptides from inhibitor-treated and untreated enzyme can identify a uniquely-eluting peptide containing the covalently attached inhibitor. LC-MS-MS can additionally be used to identify the unique peptide sequence and point of inhibitor attachment. If the inhibitor has a distinct fluorescence or UV absorbance, a denaturing chromatographic technique such as reversed-phase HPLC can be used to separate free inhibitor from protein and determine if the protein shows spectroscopic properties suggestive of the inhibitor. Finally, modification of the enzyme with inhibitor may alter its gross reversed-phase HPLC elution position, providing evidence of a covalent linkage, since a non-covalent association would not be expected to be stable under these conditions.

Example J

Quantifying the Potency of Irreversible Inhibition of MIF

An appropriate measure of the potency of an irreversible inhibitor is the ratio, $k_{inact}/K_i$, where $k_{inact}$ (having units of inverse time) is the maximum rate of inactivation that is approached with increasing inhibitor concentration and $K_i$ is the concentration of inhibitor at which a half-maximal ($0.5*k_{inact}$) inactivation rate is observed. The ratio $k_{inact}/K_i$ is essentially the second-order rate constant for the reaction of enzyme and inhibitor to form inactivated enzyme. It correctly describes the observed rate when the concentration of inhibitor is significantly below the value of $K_i$. Several methods are available to measure $k_{inact}/K_i$. The simplest in concept is to pre-incubate enzyme and inhibitor for various lengths of time and then measure the residual activity under conditions of dilution and time such that no additional inactivation takes place during the assay. The residual activities are plotted versus time and an observed inactivation rate ($k_{obs}$) calculated by fitting an exponential decay function to the data at each inhibitor concentration. The values of $k_{obs}$ are then plotted versus inhibitor concentration ([I]) and fit to the expression, $k_{obs}=k_{inact}*[I]/(K_i+[I])$, to determine $k_{inact}$ and $K_i$. Values of $k_{obs}$ can also be obtained directly from progress curves (plots of product versus time) at various inhibitor concentrations by fitting an exponential rise function. Values of $k_{inact}$ and $K_i$ are then determined by fitting to the expression, $k_{obs}=k_{inact}*[I]/(K_{i(app)}+[I])$, where $K_{i(app)}$ is $K_i*(1+[S]/K_s)$, where [S] is the concentration of any substrate which is competitive to the inhibitor in the assay and $K_s$ is the $K_m$ for that substrate. Finally, it is possible to fit either rate or progress curve data using, global equations that calculate $k_{inact}$ and $K_i$ directly without the use of the intermediate plot of $k_{obs}$ versus [I]. These are preferable in that they do not give preferential weight to of $k_{obs}$ values at high inhibitor concentrations. If global equations are used it is still desirable to examine the plot of $k_{obs}$ and [I] to see if $k_{obs}$ varies as expected with [I].

Example K

In Vivo Pharmacodynamtic Analysis

The ability of candidate compounds to impact cytokine production in vivo will be determined in an acute murine endotoxic shock model. In this model, mice (4-6/group) are injected with low levels of lipopolysaccharide (LPS) to induce cytokine production in a MIF dependent manner. Compounds will be administered either orally or through interperitoneal injection (1-20 mg/kg) using an appropriate vehicle 1 to 24 hours prior to LPS challenge. Serum cytokines (IL-1β, TNF-α, IL-6, etc.) will be quantitated from blood drawn 60-240 minutes following challenge by ELISA.

Compounds

The following non-limiting compound examples serve to illustrate further embodiments of the MIF inhibitors. It is to be understood that any embodiments listed in the Examples section are embodiments of the MIF inhibitors and, as such, are suitable for use in the methods and compositions described above.

Example L

Synthesis of 4-[1-(2-Chloro-acetyl)-azetidin-3-ylamino]-1-(4-fluoro-benzyl)-2-oxo-1,2-dihydro-quinoline-3-carbonitrile, Compound 1

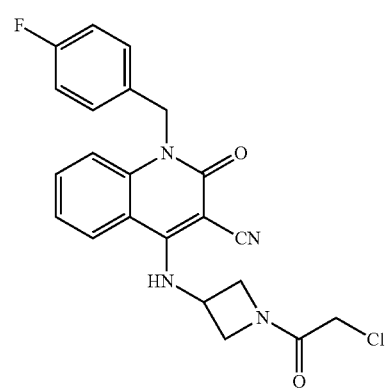

1

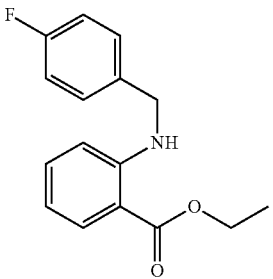

Compound A

Step 1: Synthesis of
2-(4-Fluoro-benzylamino)-benzoic acid ethyl ester,
Compound A To a stirred solution of commercially available 2-Fluoro-benzoic acid ethyl ester (1 g, 6.01 mmol) and 4-Fluoro-benzylamine (0.828 g, 6.62 mmol) in dry N,N'-dimethylformamide (10 mL) in a screw cap vial was added diisopropylethylamine (0.854 g, 6.62 mmole, 1.1 mL). The resulting solution was heated to 120° C. for 4 hours. Reaction mixture was cooled to room temperature, diluted with water and extracted with ethyl acetate (25 mL×3). Combined organic phase was washed consecutively with water, brine before drying over sodium sulfate. Organic phase was evaporated and the residue was purified by flash chromatography to afford 2-(4-Fluoro-benzylamino)-benzoic acid ethyl ester as a clear liquid (1.23 g, 75%, LCMS calc M+H 274, obs M+H 274).

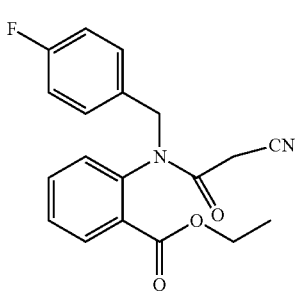

Compound B

Step 2: Synthesis of 2-[2-Cyano-acetyl)-(4-fluoro-benzyl)-amino]-benzoic acid ethyl ester, Compound B To a stirred mixture of commercially available cyanoacetic acid (1 eq, 0.170 g, 2.0 mmole) in dichloromethane was added oxalylchloride (0.253 g, 2.0 mmole, 0.169 mL) and 2 drops dimethylformamide. The reaction was stirred for 2 hours at RT until homogenous solution developed. 2-(4-Fluoro-benzylamino)-benzoic acid ethyl ester (1 eq, 0.500 g, 1.82 mmole) was added and the resulting solution, was allowed to stir at RT overnight. Reaction mixture was diluted with saturated sodium bicarbonate water (20 mL) and extracted with ethyl acetate (25 mL×3). Combined organic phase was washed consecutively with water, brine before drying over sodium sulfate. Organic phase was evaporated and the residue was purified by flash chromatography to afford 2-[(2-Cyano-acetyl)-(4-fluoro-benzyl)-amino]-benzoic acid ethyl ester as an off white solid (0.423 g, 68%, LCMS calc M+H 341, obs M+H 341).

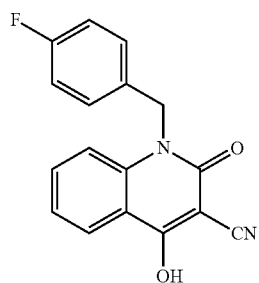

Compound C

Step 3: Synthesis of 1-(4-Fluoro-benzyl)-4-hydroxy-2-oxo-1,2-dihydro-quinoline-3-carbonitrile, compound C To a stirred solution of 2-[(2-Cyano-acetyl)-(4-fluoro-benzyl)-amino]-benzoic acid ethyl ester (1 eq, 0.500 g, 1.47 mmole) in dimethylformamide (25 mL) was added potassium carbonate (1.5 eq, 0.305 g, 2.2 mmole) the resulting mixture was heated to 80° C. for 4 hours. Reaction mixture was diluted with 1N HCl aq (25 mL) and extracted with ethyl acetate (25 mL×3). Combined organic phase was washed consecutively with water, brine before drying over sodium sulfate. Organic phase was evaporated and the residue was purified by flash chromatography to afford Synthesis of 1-(4-Fluoro-benzyl)-4-hydroxy-2-oxo-1,2-dihydro-quinoline-3-carbonitrile as a pale yellow solid (0.410 g, 95%, LCMS calc M+H 295, obs M+H 295).

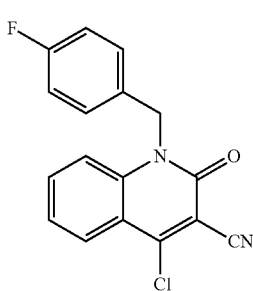

Compound D

Step 4: Synthesis of 4-Chloro-1-(4-fluoro-benzyl)-2-oxo-1,2-dihydro-quinoline-3-carbonitrile, compound D To 1-(4-Fluoro-benzyl)-4-hydroxy-2-oxo-1,2-dihydro-quinoline-3-carbonitrile (1 eq, 0.250 g, 0.85 mmole) was added POCl$_3$ neat. The resulting solution was heated to 100° C. for 8 hours, Reaction mixture was added dropwise to water (20 mL) which had been heated to 80° C. then cooled to RT and extracted with ethyl acetate (25 mL×3). Combined organic phase was washed consecutively with water, brine before drying over sodium sulfate. Organic phase was evaporated and the residue was purified by flash chromatography to afford 4-Chloro-1-(4-fluoro-benzyl)-2-oxo-1,2-dihydro-quinoline-3-carbonitrile as a yellow solid (0.156 g, 59%. LCMS calc M+H 313, obs M+H 313).

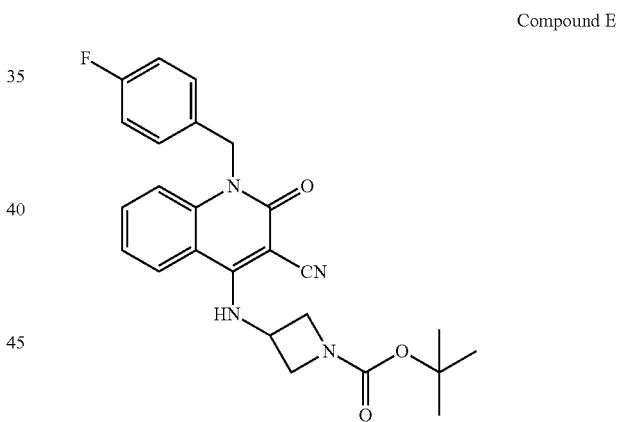

Compound E

Step 5: Synthesis of 3-[3-Cyano-1-(4-fluoro-benzyl)-2-oxo-1,2-dihydro-quinolin-4-ylamino]-azetidine-1-carboxylic acid tert-butyl ester, compound E To a stirred solution of 4-Chloro-1-(4-fluoro-benzyl)-2-oxo-1,2-dihydro-quinoline-3-carbonitrile (1 eq, 0.250 g, 0.80 mmole) in N,N'-dimethylformamide was added commercially available 3-Amino-azetidine-1-carboxylic acid tert-butyl ester (1.1 eq 0.151 g, 0.88 mmole) and treated with 60% NaH oil dispersion. (1.5 eq, 0.029 g, 1.2 mmole). After stirring for 2 h, reaction was quenched with 10% HCl aq. (1 ml) then H$_2$O (5 ml). A solid formed that was collected and dried. No further purification was necessary, afforded 3-[3-Cyano-1-(4-fluoro-benzyl)-2-oxo-1,2-dihydro-quinolin-4-ylamino]-azetidine-1-carboxylic acid tert-butyl ester as a pale yellow solid (0.322 g, 90%, calc M+H 449, obs M+H 449).

Compound F

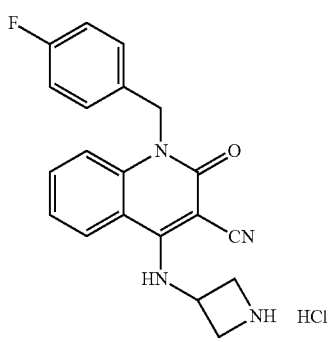

Step 6: Synthesis of 4-(Azetidin-3-ylamino)-1-(4-fluoro-benzyl)-2-oxo-1,2-dihydro-quinoline-3-carbonitrile hydrochloride salt, Compound F To a solution of 3-[3-Cyano-1-(4-fluoro-benzyl)-2-oxo-1,2-dihydro-quinolin-4-ylamino]-azetidine-1-carboxylic acid tert-butyl ester (0.250 g, 0.56 mmole) in 1,4-dioxane (2 mL) was treated with 4N HCl in dioxane (5.0 ml). Reaction stirred for 24 h before concentrating to residue and triturating with diethyl ether to afford 4-(Azetidin-3-ylamino)-1-(4-fluoro-benzyl)-2-oxo-1,2-dihydro-quinoline-3-carbonitrile hydrochloride salt as a yellow solid (0.194 g, quantitative yield, calc M+H 349, obs M+H 349).

Compound 1

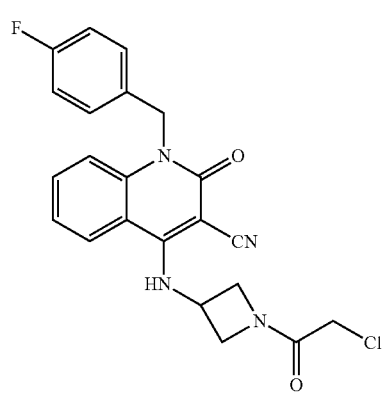

Step 7: Synthesis of 4-[1-(2-Chloro-acetyl)-azetidin-3-ylamino]-1-(4-fluoro-benzyl)-2-oxo-1,2-dihydro-quinoline-3-carbonitrile, compound 1

To a suspension of 4-(Azetidin-3-ylamino)-1-(4-fluoro-benzyl)-2-oxo-1,2-dihydro-quinoline-3-carbonitrile hydrochloride salt (1 eq, 0.150 g, 0.43 mmole) in dichloromethane at −10° C. was added chloroacetyl chloride (1.1 eq, 0.054 g, 0.474 mmole) followed by the addition of N,N'-diisopropylethylamine (1.5 eq, 0.083 g, 0.646 mmole, 0.110 mL). The resulting solution stirred at −10° C. for 1 hour then warmed to RT and stirred for an additional 2 hours. The reaction was quenched into ice cooled water and extracted with ethyl acetate (25 mL×3). Combined organic phase was washed consecutively with water, brine before drying over sodium sulfate. Organic phase was evaporated and the residue was purified by flash chromatography to afford 4-[1-(2-Chloro-acetyl)-azetidin-3-ylamino]-1-(4-fluoro-benzyl)-2-oxo-1,2-dihydro-quinoline-3-carbonitrile as a yellow solid (0.027 g, 15% calc M+H 425, obs M+H 425).

Example M

Synthesis of 4-(4-acryloylpiperazin-1-yl)-1-(4-fluorobenzyl)-2-oxo-1,2-dihydroquinoline-3-carbonitrile, Compound 2

Compound G

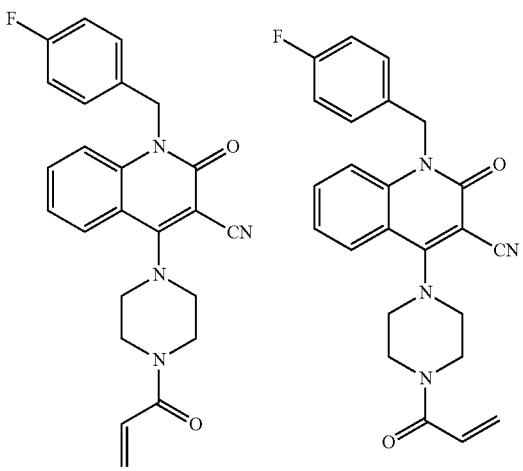

Step 1: Synthesis of 4-[3-Cyano-1-(4-fluoro-benzyl)-2-oxo-1,2-dihydro-quinolin-4-yl]-piperazine-1-carboxylic acid tert-butyl ester To a stirred solution of 4-Chloro-1-(4-fluoro-benzyl)-2-oxo-1,2-dihydro-quinoline-3-carbonitrile, compound C, (1 eq, 0.250 g, 0.80 mmole) in N,N'-dimethylformamide was added commercially available piperazine-1-carboxylic acid tert-butyl ester (1.1 eq, 0.164 g, 0.88 mmole) and treated with 60% NaH oil dispersion (1.5 eq, 0.029 g, 1.2 mmole). After stirring for 2 h, reaction was quenched with 10% HCl aq, (1 ml) then H₂O (5 ml), A solid formed that was collected and dried. No further purification was necessary, afforded 4-[3-Cyano-1-(4-fluoro-benzyl)-2-oxo-1,2-dihydro-quinolin-4-yl]-piperazine-1-carboxylic acid tert-butyl ester as a pale yellow solid (0.325 g, 88%, calc M+H 463, obs M+H 463).

Compound H

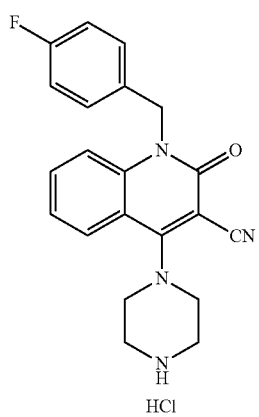

HCl

Step 2: Synthesis of 1-(4-Fluoro-benzyl)-2-oxo-4-piperazin-1-yl-1,2-dihydro-quinoline-3-carbonitrile hydrochloride salt To a solution of 4-[3-Cyano-1-(4-fluoro-benzyl)-2-oxo-1,2-dihydro-quinolin-4-yl]-piperazine-1-carboxylic acid tert-butyl ester (0.250 g, 0.54 mmole) in 1,4-dioxane (2mL) was treated with 4N HCl in dioxane (5.0 ml). Reaction stirred for 24 h before concentrating to residue and triturating with diethyl ether to afford 1-(4-Fluoro-benzyl)-2-oxo-4-piperazin-1-yl-1,2-dihydro-quinoline-3-carbonitrile hydrochloride salt as a yellow solid (0.195 g, quantitative yield, calc M+H 363, obs M+H 363).

Compound 2

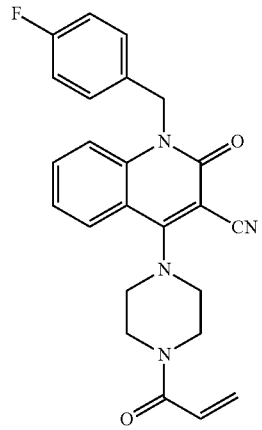

Step 3: Synthesis of 4-(4-Acryloyl-piperazin-1-yl)-1-(4-fluoro-benzyl)-2-oxo-1,2-dihydro-quinoline-3-carbonitrile To a suspension of 1-(4-Fluoro-benzyl)-2-oxo-4-piperazin-1-yl-1,2-dihydro-quinoline-3-carbonitrile hydrochloride salt (1 eq, 0.150 g, 0.41 mmole) in dichloromethane at −10° C. was added acryloyl chloride (1.1 eq, 0.054 g, 0.45 mmole) followed by the addition of diisopropylamine (1.5 eq, 0.083 g, 0.62 mmole, 0.103 mL). The resulting solution stirred at 10° C. for 1 hour then warmed to RT and stirred for an additional 2 hours. The reaction was quenched into ice cooled water and extracted with ethyl acetate (25 mL×3). Combined organic phase was washed consecutively with water, brine before drying over sodium sulfate. Organic phase was evaporated and the residue was purified by flash chromatography to afford 4-(4-Acryloyl-piperazin-1-yl)-1-(4-fluoro-benzyl)-2-oxo-1,2-dihydro-quinoline-3-carbonitrile as a yellow solid (0.043 g, 25% calc M+H 417, obs M+H 417).

Example N

Synthesis of 4-(1-Acryloyl-azetidin-3-ylamino)-1-(2-ethoxy-ethyl)-2-oxo-1,2-dihydro-quinoline-3-carbonitrile, Compound 3

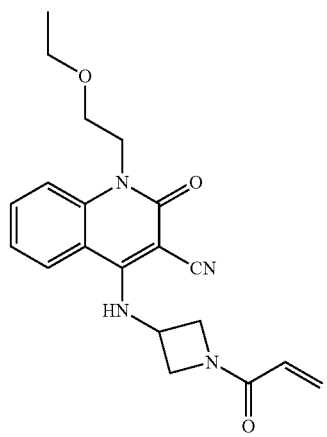

Compound I

Step 1: Synthesis of 2-(2-Ethoxy-ethylamino)-benzoic acid ethyl ester, compound I.

To a stirred solution of commercially available 2-Fluoro-benzoic acid ethyl ester (1 g, 6.01 mmol) and 2-Ethoxy-ethylamine (0.500 g, 2.97 mmole) in dry N,N'dimethylformamide (10 mL) in a screw cap vial was added diisopropylethylamine (1.1 eq, 0.223 g, 3.27 mmole, 1.1 mL). The resulting solution was heated to 120° C. for 4 hours. Reaction mixture was cooled to room temperature, diluted with water and extracted with ethyl acetate (25 mL×3). Combined organic phase was washed consecutively with water, brine before drying over sodium sulfate. Organic phase was evaporated and the residue was purified by flash chromatography to afford 2-(2-Ethoxy-ethylamino)-benzoic acid ethyl ester as a clear liquid (0.493 g, 70%, LCMS calc M+H 238, obs M+H 238).

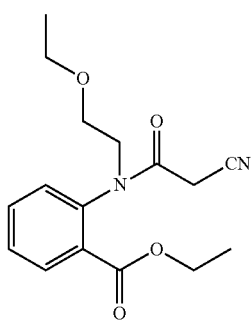

Compound J

Step 2: Synthesis of 2-[(2-Cyano-acetyl)-(2-ethoxy-ethyl)-amino]-benzoic acid ethyl ester, compound J To a stirred mixture of commercially available cyanoacetic acid (1.1 eq, 0.118 g, 1.39 mmole) in dichloromethane was added oxalylchloride (0.353 g, 2.78 mmole, 0.236 mL) and 2 drops N,N'-dimethylformamide). The reaction was stirred for 2 hours at RT until homogenous solution developed. 2-(2-Ethoxy-ethylamino)-benzoic acid ethyl ester (1 eq, 0.300 g, 1.26 mmole) was added and the resulting solution was allowed to stir at RT overnight. Reaction mixture was diluted with saturated sodium bicarbonate water (20 mL) and extracted with ethyl acetate (25 mL×3). Combined organic phase was washed consecutively With water, brine before drying over sodium sulfate. Organic phase was evaporated and the residue was purified by flash chromatography to afford 2-[(2-Cyano-acetyl)-(2-ethoxy-ethyl)-amino]-benzoic acid ethyl ester as clear liquid (0.292 g, 76%, LCMS calc M+H 305, obs M+H 305).

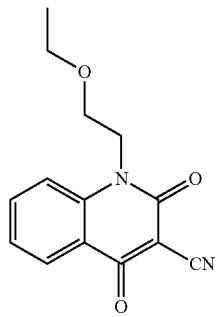

Compound K

Step 3: Synthesis of 1-(2-Ethoxy-ethyl)-4-hydroxy-2-oxo-1,2-dihydro-quinoline-3-carbonitrile, compound K To a stirred solution of 2-[(2-Cyano-acetyl)-(2-ethoxy-ethyl)-amino]-benzoic acid ethyl ester (1 eq, 0.200 g, 0.66 mmole) in dimethylformamide (25 mL) was added potassium carbonate (1.5 eq, 0.136 g, 0.99 mmole) the resulting mixture was heated to 80° C. for 4 hours. Reaction mixture was diluted with 1N HCl aq (25 mL) and extracted with ethyl acetate (25 mL×3). Combined organic phase was washed consecutively with water, brine before, drying over sodium sulfate. Organic phase was evaporated and the residue was purified by flash chromatography to afford 1-(2-Ethoxy-ethyl)-4-hydroxy-2-oxo-1,2-dihydro-quinoline-3-carbonitrile as a pale yellow solid (0.161 g, 95%, LCMS calc M+H 259, obs M+H 259).

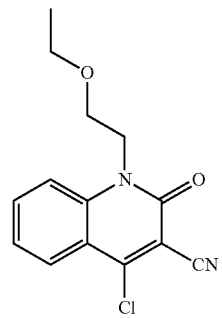

Compound L

Step 4: Synthesis of 4-Chloro-1-(2-ethoxy-ethyl)-2-oxo-1,2-dihydro-quinoline-3-carbonitrile, compound L To 1-(2-Ethoxy-ethyl)-4-hydroxy-2-oxo-1,2-dihydro-quinoline-3-carbonitrile (1 eq, 0,150 g, 0.58 mmole) was added POCl$_3$ neat. The resulting solution was heated to 100° C. for 8 hours. Reaction mixture was added dropwise to water (20 mL) which had been heated to 80° C. then cooled to RT and extracted with ethyl acetate (25 mL×3). Combined, organic phase was Washed consecutively with water, brine before drying over sodium sulfate. Organic phase was evaporated and the residue was purified by flash chromatography to afford 4-Chloro-1-(2-ethoxy-ethyl)-2-oxo-1,2-dihydro-quinoline-3-carbonitrile as a yellow solid (0.109 g, 68%. LCMS calc M+H 277, obs M+H 277).

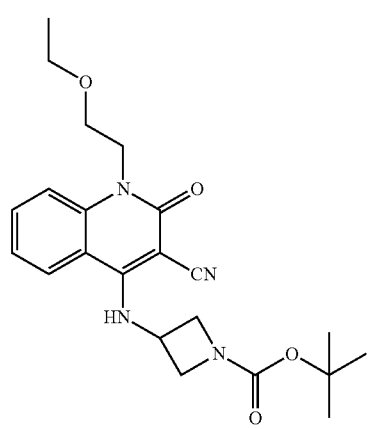

Compound M

Step 5: Synthesis of 3-[3-Cyano-1-(2-ethoxy-ethyl)-2-oxo-1,2-dihydro-quinolin-4-ylamino]-azetidine-1-carboxylic acid tert-butyl ester To a stirred solution of 4-Chloro-1-(2-ethoxy-ethyl)-2-oxo-1,2-dihydro-quinoline-3-carbonitrile (1 eq, 0.100 g, 0.36 mmole) in N,N'-dimethylfomamide was added commercially available 3-Amino-azetidine-1-carboxylic acid tert-butyl ester (1.1 eq, 0.068 g, 0.39 mmole) and treated with 60% NaH oil dispersion (1.5 eq, 0.013 g, 0.54 mmole). After stirring for 2 h, reaction was quenched with 10% HCl aq. (1 ml) then H₂O (5 ml). A solid formed that was collected and dried. No further purification was necessary, afforded 3-[3-Cyano-1-(2-ethoxy-ethyl)-2-oxo-1,2-dihydro-quinolin-4-ylamino]-azetidine-1-carboxylic acid tert-butyl ester as a pale yellow solid (0.133 g, 90%, calc M+H 413, obs M+H 413).

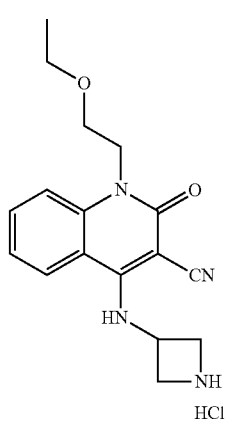

Compound N

Step 6: Synthesis of 4-(Azetidin-3-ylamino)-1-(2-ethoxy-ethyl)-2-oxo-1,2-dihydro-quinoline-3-carbonitrile hydrochloride salt To a solution of 3-[3-Cyano-1-(2-ethoxy-ethyl)-2-oxo-1,2-dihydro-quinolin-4-ylamino]-azetidine-1-carboxylic acid tert-butyl ester (0.120 g, 0.29 mmole) in 1,4-dioxane (2 mL) was treated with 4N HCl in dioxane (5.0 ml). Reaction stirred for 24 h before concentrating to residue and triturating with diethyl ether to afford 4-(Azetidin-3-ylamino)-1-(2-ethoxy-ethyl)-2-oxo-1,2-dihydro-quinoline-3-carbonitrile hydrochloride salt as a yellow solid (0.100 g, quantitative yield, calc M+H 313, obs M+H 313).

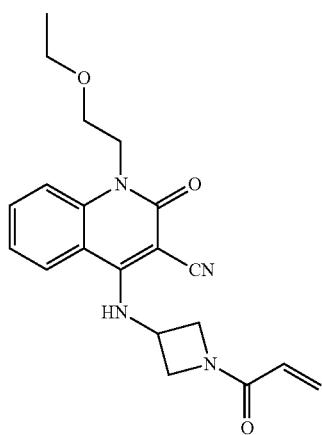

Compound 3

Step 7: Synthesis of 4-(1-Acryloyl-azetidin-3-ylamino)-1-(2-ethoxy-ethyl)-2-oxo-1,2-dihydro-quinoline-3-carbonitrile To a suspension of 4-(Azetidin-3-ylamino)-1-(2-ethoxy-ethyl)-2-oxo-1,2-dihydro-quinoline-3-carbonitrile hydrochloride salt (1 eq, 0.050 g, 0.16 mmole) in dichloromethane at −10° C. was added acryloyl chloride (1.1 eq, 0.005 g, 0.055 mmole) followed by the addition of diisopropylamine (1.5 eq, 0.031 g, 0.075 mmole, 0.05mL). The resulting solution stirred at −10° C. for 1 hour then warmed to RT and stirred for an additional 2 hours. The reaction was quenched into ice cooled water and extracted with ethyl acetate (25 mL×3). Combined organic phase was washed consecutively with water, brine before drying over sodium sulfate. Organic phase was, evaporated and the residue was purified by flash chromatography to afford 4-(1-Acryloyl-azetidin-3-ylamino)-1-(2-ethoxy-ethyl)-2-oxo-1,2-dihydro-quinoline-3-carbonitrile as a yellow solid (0.008 g, 28% calc M+H 367, obs M+H 367).

Example O

Synthesis of 4-(1-Acryloyl-piperidin-4-ylamino)-1-methyl-2-oxo-1,2-dihydro-quinoline-3-carbonitrile, Compound 4

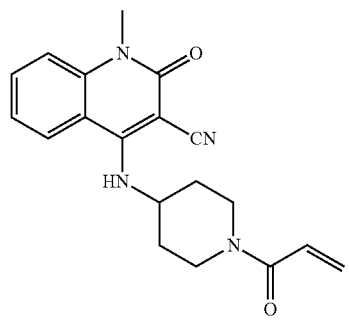

Compound O

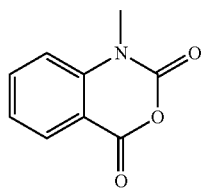

Step 1: Synthesis of 1-methyl-2H-3,1-benzoxazine-2,4(1H)-dione, compound O

Commercially available 2H-3,1-benzoxazine-2,4(1H)-dione (61.3 mmol, 1.0 eq)) was taken up in N,N'-dimethylformamide (120 ml) then treated with portion wise addition of sodium hydride (60% oil dispersion, 67.4 mmol, 1.1 eq). After stirring 30 min, methyl iodide (64.4 mmol, 1.05 ml) was dripped in over 5 min. The reaction stirred at rt for 15 h. To quench, a mixture of saturated NR₄Cl:H20 (1:1, 100 ml) was added. After stirring for 30 min, a solid formed that was collected by vacuum filtration and dried to afford 6.5 g (60% yield) of compound I as a yellow solid. ¹H-NMR (DMSO-d₆): 8.1-8.0 (m, 1H), 7.9-7.8 (in 1H), 7.5 (d, J=8.7 Hz, 1H), 7.4-7.3 (m, 1H), 3.5 (s, 3H); LC/MS m/z calc M+H 178, obs M+H 178.

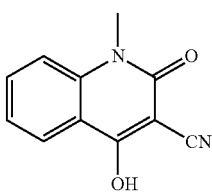

Compound P

Step 2: Synthesis of 4-hydroxy-1-methyl-2-oxo-1,2-dihydroquinoline-3-carbonitrile; compound P Compound O, (2.50 g, 14.1 mmol) was dissolved in N,N'-dimethylformamide (30 ml) and then treated with ethylcyano acetate (1.58 ml, 14.8 mmol) followed by portion wise addition of sodium hydride (60% oil dispersion, 16.9 mmol, 2.2 eq). The reaction stirred 15 h at rt and was then quenched by the addition of 10% HClaq (15 ml). The mixture stirred 30 min resulting in a yellow solid which was filtered, washed with water, and dried to afford 1.75 g (62%) of compound P. $^1$H-NMR (DMSO-$d_6$): 8.1 (d, J=8.1 Hz, 1H), 7.6 (t,J=7.2, 1H), 7.5 (d, J=8.1 Hz, 1H), 7.2 (t, J=7.8 Hz, 1H), 3.6 (s, 3H); LC/MS m/z calc M+H 200, obs M+H 201.

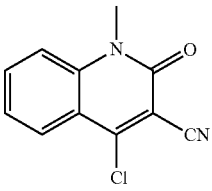

Compound Q

Step 3: Synthesis of 4-chloro-1-methyl-2-oxo-1,2-dihydroquinoline-3-carbonitrile; compound Q Compound P (1.13 g, 5.64 mmol): was taken up in N,N'-dimethylacetamide (10 ml). The solution was then treated with lithium chloride (1.20 g, 5.0 eq) and p-toluenesulfonyl chloride (1.29 g, 1.20 eq). The mixture stirred at rt for 1 h and was then quenched with 10% HCl aq (10 ml). After stirring for 30 min, a solid formed which was collected by vacuum filtration, washed with water (2×), and dried for product, compound III as a white solid (1.12 g, 91% yield; calc M+H 219, obs M+H 219).

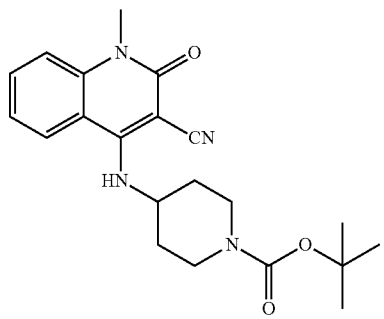

Compound R

Step 4: tert-butyl 4-((3-cyano-1-methyl-2-oxo-1,2-dihydroquinolin-4-yl)amino)piperidine-1-carboxylate carboxylate, compound R Using the general procedure outline in example 1, step 5 the title compound was obtained as a viscous oil.

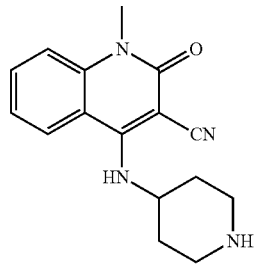

Compound S

Step 5: 1-methyl-2-oxo-4-(piperidin-4-ylamino)-1,2-dihydroquinoline-3-carbonitrile, compound S Using the general procedure outline in example 1, step 6 the title compound was obtained as a white solid.

Compound 4

Step 6: Synthesis of 4-(1-Acryloyl-piperidin-4-ylamino)-1-methyl-2-oxo-1,2-dihydro-quinoline-3-carbonitrile To a suspension of 1-Methyl-2-oxo-4-(piperidin-4-ylamino)-1,2-dihydro-quinoline-3-carbonitrile hydrochloride salt (leg, 0.020 g, 0.07 mmole) in dichloromethane at −10° C. was added acryloyl chloride (1.1 eq, 0.007 g, 0.077 mmole) followed by the addition of N,N'-diisopropylethylamine (1.5 eq, 0.014 g, 0.011 mmole, 0.02 mL). The resulting solution stirred at −10° C. for 1 hour then warmed to RT and stirred for an additional 2 hours. The reaction was quenched into ice cooled water and extracted with ethyl acetate (25 mL×3). Combined organic phase was washed consecutively with water, brine before drying over sodium sulfate. Organic phase was evaporated and the residue was purified by flash chromatography to afford 4-(1-Acryloyl-piperidin-4-ylamino)-1-methyl-2-oxo-1,2-dihydro-quinoline-3-carbonitrile as a yellow solid (0.004 g, 32% calc M+H 337, obs M+H 337).

The present invention is not to be limited in scope by the specific embodiments disclosed in the examples which are intended as illustrations of a few aspects of the invention and Equivalents Those skilled in the art will recognize, or be able to ascertain, using no more than routine experimentation, numerous equivalents to the specific embodiments described specifically herein. Such equivalents are intended to be encompassed, in the scope of the following claims.

The invention claimed is:
1. A compound of Formula III:

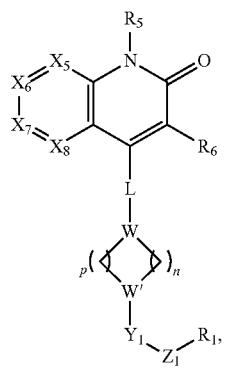

or a pharmaceutically acceptable salt, hydrate, solvate or tautomer thereof, wherein:
each of $X_5$, $X_6$, $X_7$, and $X_8$ is independently $CR_7$ or N;
L is a bond or $NR_2$;
one of W or W' is N and the other is CH;
each n and p is independently 1, 2, or 3;
$Y_1$ is a bond, —C(O)— or —$NR_2$—;
$Z_1$ is a bond, —C(O)—, —N($R_3$)— or —$SO_2$—;
$R_1$ is —$C_1$-$C_6$ alkyl, branched or unbranched optionally substituted with halogen or —CN,
—$C_2$-$C_6$ alkene branched or unbranched,
—$C_2$-$C_6$ alkyne, optionally substituted with —$C_1$-$C_3$ alkyl,
—$C_3$-$C_4$ cycloalkyl, optionally substituted with —$C_1$-$C_3$ alkyl or —CN, or
—a nonaromatic monocyclic heterocycle, optionally substituted with —$C_1$-$C_3$ alkyl;
$R_2$ is H or —$C_1$-$C_6$ alkyl;
$R_3$ is H or —$C_1$-$C_6$ alkyl;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$alkyl)-$NR_8R_9$, —($C_1$-$C_3$ alkyl)heteroaryl or —($C_1$-$C_3$ alkyl)aryl, wherein $R_5$ is optionally substituted;
$R_6$ is selected from the group consisting of —CN, —$NO_2$, —$CO_2H$, C(O)-Rx; —$CO_2Rx$; and
—$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$ or $SO_2$-alkyl;
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_8$ and $R_9$ are optionally substituted; and
$Y_1$ and $Z_1$ are not both a bond.
2. The compound of claim 1, wherein $R_6$ is —CN.
3. The compound of claim 1, wherein p is 2 and n is 2.
4. The compound of claim 1, wherein p is 1 and n is 1.
5. The compound of claim 1, wherein $R_1$ is —$CH_2Cl$, —$CH_2CN$, —CH=$CH_2$, —C($CF_3$)=$CH_2$, —C($CH_3$)=$CH_2$, —CH=CH($CH_3$), —CH=CH(Cl), —CN, oxiran-2-yl or 1-cyanocyclopropyl.
6. The compound of claim 1, having the Formula IIIa:

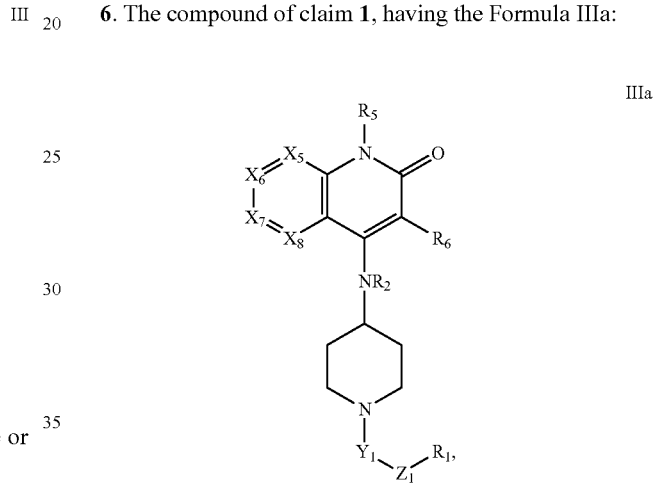

or a pharmaceutically acceptable salt, hydrate, solvate or tautomer thereof,
wherein:
each of $X_5$, $X_6$, $X_7$, and $X_8$ is independently $CR_7$ or N;
$Y_1$ is a bond or —C(O)—;
$Z_1$ is a bond, —C(O)—, —N($R_3$)— or —$SO_2$—;
$R_1$ is —$C_1$-$C_6$ alkyl, branched or unbranched optionally substituted with halogen or —CN,
—$C_2$-$C_6$ alkene branched or unbranched,
—$C_2$-$C_6$ alkyne, optionally substituted with —$C_1$-$C_3$ alkyl,
—$C_3$-$C_4$ cycloalkyl, optionally substituted with —$C_1$-$C_3$ alkyl or —CN, or
a nonaromatic monocyclic heterocycle, optionally substituted with —$C_1$-$C_3$ alkyl;
$R_2$ is H or —$C_1$-$C_6$alkyl;
$R_3$ is —H or —$C_1$-$C_6$ alkyl;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is CN;
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$ or $SO_2$-alkyl; and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_8$ and $R_9$ are optionally substituted.

7. The compound of claim 1, having the Formula IIIb:

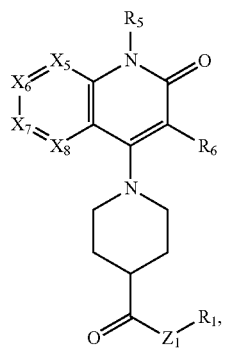

IIIb or a pharmaceutically acceptable salt, hydrate, solvate or tautomer thereof, wherein:

each of $X_5$, $X_6$, $X_7$, and $X_8$ is independently $CR_7$ or N;

$Z_1$ is a bond or $NR_3$-;

$R_1$ is —$C_1$-$C_6$ alkyl, branched or unbranched optionally substituted with halogen or —CN, —$C_2$-$C_6$ alkene branched or unbranched, —$C_2$-$C_6$ alkyne, optionally substituted with —$C_1$-$C_3$ alkyl, —$C_3$-$C_4$ cycloalkyl, optionally substituted with —$C_1$-$C_3$ alkyl or —CN, or a nonaromatic monocyclic heterocycle, optionally substituted with —$C_1$-$C_3$ alkyl;

$R_3$ is —H or —$C_1$-$C_6$ alkyl;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is CN;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$alkyl), —$OCF_3$, —$SO_2NH_2$ or $SO_2$-alkyl; and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_8$ and $R_9$ are optionally substituted.

8. The compound of claim 1, having the Formula IIIc:

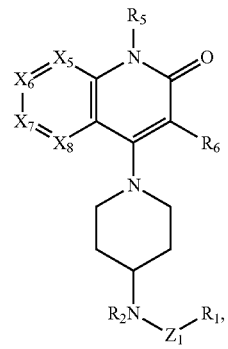

IIIc or a pharmaceutically acceptable salt, hydrate, solvate or tautomer thereof, wherein:

each of $X_5$, $X_6$, $X_7$, and $X_8$ is independently $CR_7$ or N;

$Z_1$ is —CO— or —$SO_2$—;

$R_1$ is —$C_1$-$C_6$ alkyl, branched or unbranched optionally substituted with halogen or —CN —$C_2$-$C_6$ alkene branched or unbranched, —$C_2$-$C_6$ alkyne, optionally substituted with —$C_1$-$C_3$ alkyl, —$C_3$-$C_4$ cycloalkyl, optionally substituted with —$C_1$-$C_3$ alkyl or —CN, or a nonaromatic monocyclic heterocycle, optionally substituted with —$C_1$-$C_3$ alkyl;

$R_2$ is H or —$C_1$-$C_6$ alkyl;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is selected from the group consisting of —CN, —$NO_2$, —$CO_2H$, C(O)—Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$ or —$SO_2$-alkyl; and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_3$ and $R_9$ are optionally substituted.

9. The compound of claim 1, having the Formula IIId:

IIId or a pharmaceutically acceptable salt, hydrate, solvate or tautomer thereof, wherein:

each of $X_5$, $X_6$, $X_7$, and $X_8$ is independently $CR_7$ or N;

$Z_1$ is a bond or $NR_3$-;

$R_1$ is —$C_1$-$C_6$ alkyl, branched or unbranched optionally substituted with halogen or —CN,
 —$C_2$-$C_6$ alkene branched or unbranched,
 —$C_2$-$C_6$ alkyne, optionally substituted with —$C_1$-$C_3$ alkyl,
 —$C_3$-$C_4$ cycloalkyl, optionally substituted with —$C_1$-$C_3$ alkyl or —CN, or
 a nonaromatic monocyclic heterocycle, optionally substituted with —$C_1$-$C_3$ alkyl;

$R_3$ is —H or —$C_1$-$C_6$ alkyl;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is CN;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$ or $SO_2$-alkyl; and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_8$ and $R_9$ are optionally substituted.

10. The compound of claim 1, having the Formula IIIe:

IIIe or a pharmaceutically acceptable salt, hydrate, solvate or tautomer thereof, wherein:

each of $X_5$, $X_6$, $X_7$, and $X_8$ is independently $CR_7$ or N;

$Z_1$ is a bond or $NR_3$—;

$R_1$ is —$C_1$-$C_6$ alkyl, branched or unbranched optionally substituted with halogen or —CN,
 —$C_2$-$C_6$ alkene branched or unbranched,
 —$C_2$-$C_6$ alkyne, optionally substituted with —$C_1$-$C_3$ alkyl,
 —$C_3$-$C_4$ cycloalkyl, optionally substituted with —$C_1$-$C_3$ alkyl or —CN, or
 a nonaromatic monocyclic heterocycle, optionally substituted with —$C_1$-$C_3$ alkyl;

$R_2$ is H or —$C_1$-$C_6$ alkyl;

$R_3$ is —H, or —$C_1$-$C_6$ alkyl;

$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;

$R_6$ is selected from the group consisting of —CN, —$NO_2$, —$CO_2H$, C(O)-Rx; —$CO_2Rx$; and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S;

$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$alkyl), —$OCF_3$, —$SO_2NH_2$ or —$SO_2$-alkyl; and $R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_s$ and $R_9$ are optionally substituted.

11. The compound of claim 1, having the Formula IIIf:

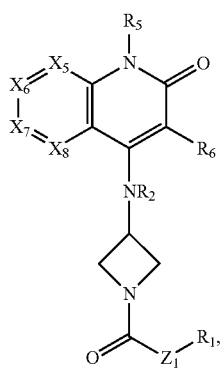

or a pharmaceutically acceptable salt, hydrate, solvate or tautomer thereof,
wherein:
each of $X_5$, $X_6$, $X_7$, and $X_8$ is independently $CR_7$ or N;
$Z_1$ is a bond or $NR_3$;
$R_1$ is —$C_1$-$C_6$ alkyl, branched or unbranched optionally substituted with halogen or —CN,
—$C_2$-$C_6$ alkene branched or unbranched,
—$C_2$-$C_6$ alkyne, optionally substituted with —$C_1$-$C_3$ alkyl or
—$C_3$-$C_4$ cycloalkyl, optionally substituted with —$C_1$-$C_3$ alkyl or —CN, or
a nonaromatic monocyclic heterocycle, optionally substituted with —$C_1$-$C_3$ alkyl;
$R_2$ is H or —$C_1$-$C_6$ alkyl;
$R_3$ is H or —$C_1$-$C_6$ alkyl;
$R_5$ is H, —$C_1$-$C_6$ alkyl, —$C_2$-$C_6$ alkene, —($C_0$-$C_3$ alkyl)-($C_3$-$C_6$)cycloalkyl, —($C_2$-$C_6$ alkyl)-O—($C_1$-$C_3$ alkyl), —($C_2$-$C_6$ alkyl)-O—($C_3$-$C_6$)cycloalkyl, —($C_2$-$C_6$ alkyl)-O-aryl, —($C_2$-$C_6$ alkyl)-O-heteroaryl, —($C_2$-$C_6$ alkyl)-$NR_8R_9$, —($C_1$-$C_3$ alkyl)heteroaryl or —($C_1$-$C_3$ alkyl)aryl, wherein $R_5$ is optionally substituted;
$R_6$ is —CN;
$R_7$ is H, F, Cl, —$CF_3$, —CN, —$CO_2$-alkyl, —$C_1$-$C_6$ alkyl, —$C_3$-$C_7$(cycloalkyl), —O—($C_1$-$C_6$ alkyl), —$OCF_3$, —$SO_2NH_2$ or —$SO_2$-alkyl; and
$R_8$ and $R_9$ are each independently H, —$C_1$-$C_6$ alkyl, —($C_0$-$C_6$ alkyl)aryl, $C_0$-$C_3$ alkyl)-$C_3$-$C_6$(cycloalkyl), —C(O)—$C_1$-$C_3$ alkyl, —C(O)—$C_2$-$C_3$ alkene; or $R_3$ and $R_4$, when taken together with the nitrogen to which they are attached, can form a heterocycle containing from one to three heteroatoms selected from N, O, and S, and wherein $R_8$ and $R_9$ are optionally substituted.

12. The compound of claim 1, wherein the compound is selected from the group consisting of:
1-methyl-2-oxo-4-(4-propioloylpiperidin-1-yl)-1,2-dihydroquinoline-3-carbonitrile;
4-(4-(3-chloropropioloyl)piperidin-1-yl)-1-methyl-2-oxo-1,2-dihydroquinoline-3-carbonitrile;
4-(4-acryloylpiperidin-1-yl)-1-methyl-2-oxo-1,2-dihydroquinoline-3-carbonitrile;
4-(4-methacryloylpiperidin-1-yl)-1-methyl-2-oxo-1,2-dihydroquinoline-3-carbonitrile;
(E)-4-(4-but-2-enoylpiperidin-1-yl)-1-methyl-2-oxo-1,2-dihydroquinoline-3-carbonitrile;
4-(4-(2-chloroacety)piperidin-1-yl)-1-methyl-2-oxo-1,2-dihydroquinoline-3-carbonitrile;
1-methyl-2-oxo-4-(4-(2-oxopyrrolidine-1-carbonyl)piperidin-1-yl)-1,2-dihydroquinoline-3-carbonitrile;
1-methyl-4-(4-(2-(methylsulfonyl)vinyl)piperidin-1-yl)-2-oxo-1,2-dihydroquinoline-3-carbonitrile;
4-(1-(3-cyano-1-methyl-2-oxo-1,2-dihydroquinolin-4-yl)piperidin-4-yl)-N-methylbut-2-ynamide;
N-(1-(3-cyano-1-methyl-2-oxo-1,2-dihydroquinolin-4-yl)piperidin-4-yl)methyl)acrylamide;
N-(1-(3-cyano-1-methyl-2-oxo-1,2-dihydroquinolin-4-yl)piperidin-4-yl)methacrylamide;
N-(1-(3-cyano-1-methyl-2-oxo-1,2-dihydroquinolin-4-yl)piperidin-4-yl)propiolamide;
N-acryloyl-N-(1-(3-cyano-1-methyl-2-oxo-1,2-dihydroquinolin-4-yl)piperidin-4-yl)acrylamide;
4-(4-(cyanomethylamino)piperidin-1-yl)-1-methyl-2-oxo-1,2-dihydroquinolin-3-carbonitrile;
1-methyl-2-oxo-4-(4-(3-vinyl-1H-pyrazol-5-ylamino)piperidin-1-yl)-1,2-dihydroquinoline-3-carbonitrile;
4-(1-acryloylpiperidin-4-ylamino)-1-methyl-2-oxo-1,2-dihydroquinoline-3-carbonitrile;
4-(1-acryloylpiperidin-4-ylamino)-1-(4-fluorobenzyl)-2-oxo-1,2-dihydroquinoline-3-carbonitrile;
1-(4-fluorobenzyl)-2-oxo-4-(1-propioloylpiperidin-4-ylamino)-1,2-dihydroquinoline-3-carbonitrile;
4-(1-(2-chloroacetyl)piperidin-4-ylamino)-1-(4-fluorobenzyl)-2-oxo-1,2-dihydroquinoline-3-carbonitrile;
1-methyl-2-oxo-4-(1-(vinylsulfonyl)piperidin-4-ylamino)-1,2-dihydroquinolin-3-carbonitrile;
4-(1-(cyanomethyl)piperidin-4-ylamino)-1-(4-fluorobenzyl)-2-oxo-1,2-dihydroquinoline-3-carbonitrile;
4-(1-(1-cyanocyclopropanecarbonyl)piperidin-4-ylamino)-1-methyl-2-oxo-1,2-dihydroquinoline-3-carbonitrile;
1-methyl-2-oxo-4-(1-(2-(trifluoromethyl)acryloyl)piperidin-4-ylamino)-1,2-dihydroquinoline-3-carbonitrile;
1-methyl-2-oxo-4-(1-(2-oxopyrrolidine-1-carbonyl)piperidin-4-ylamino)-1,2-dihydroquinoline-3-carbonitrile;
4-(1-acryloylpiperidin-4-ylamino)-1-(2-(dimethylamino)ethyl)-2-oxo-1,2-dihydroquinoline-3-carbonitrile;
N-((1-(3-cyano-1-methyl-2-oxo-1,2-dihydroquinolin-4-yl)azetidin-3-yl)methyl)ethenesulfonamide;
N-((3-(3-cyano-1-methyl-2-oxo-1,2-dihydroquinolin-4-ylamino)cyclobutyl)methyl)ethenesulfonamide;
1-methyl-2-oxo-4-(3-(vinylsulfonyl)azetidin-1-yl)-1,2-dihydroquinoline-3-carbonitrile;
N-((3-(3-cyano-1-methyl-2-oxo-1,2-dihydroquinolin-4-ylamino)cyclobutyl)methyl)acrylamide; 1-(3-cyano-1-methyl-2-oxo-1,2-dihydroquinolin-4-yl)-N-(cyanomethyl)piperidine-4-carboxamide;
N-(1-(3-cyano-1-methyl-2-oxo-1,2-dihydroquinolin-4-yl)piperidin-4-yl)acrylamide;
1-cyano-N-(1-(3-cyano-1-methyl-2-oxo-1,2-dihydroquinolin-4-yl)piperidin-4-yl)cyclopropanecarboxamide;
(E)-3-chloro-N-(1-(3-cyano-1-methyl-2-oxo-1,2-dihydroquinolin-4-piperidin-4-yl)acrylamide;
2-chloro-N-(1-(3-cyano-1-methyl-2-oxo-1,2-dihydroquinolin-4-yDpiperidin-4-yl)acetamide;
N-(1-(3-cyano-1-methyl-2-oxo-1,2-dihydroquinolin-4-yl)piperidin-4-yl)-2-fluoroacetamide;
N-(1-(3-cyano-1-methyl-2-oxo-1,2-dihydroquinolin-4-yl)piperidin-4-yl)ethenesulfonamide;
N-(1-(3-cyano-1-methyl-2-oxo-1,2-dihydroquinolin-4-yl)piperidin-4-yl)ethynesulfonamide;
N-(1-(3-cyano-1-methyl-2-oxo-1,2-dihydroquinolin-4-yl)piperidin-4-yl)-2-(trifluoromethyl)acrylamide;

4-(3-acryloylazetidin-1-yl)-1-methyl-2-oxo-1,2-dihydroquinoline-3-carbonitrile;
4-(3-acryloylazetidin-1-yl)-1-(4-fluorobenzyl)-2-oxo-1,2-dihydroquinoline-3-carbonitrile;
4-(3-acryloylazetidin-1-yl)-1-(2-(dimethylamino)ethyl)-2-oxo-1,2-dihydroquinoline-3-carbonitrile;
1-methyl-2-oxo-4-(3-propioloylazetidin-1-yl)-1,2-dihydroquinoline-3-carbonitrile;
4-(3-acryloylazetidin-1-yl)-1-benzyl-2-oxo-1,2-dihydroquinoline-3-carbonitrile;
1-(3-cyano-1-methyl-2-oxo-1,2-dihydroquinolin-4-yl)-N-(cyanomethyl)azetidine-3-carboxamide;
1-methyl-2-oxo-4-(3-(2-(trifluoromethyl)acryloyl)azetidin-1-yl)-1,2-dihydroquinoline-3-carbonitrile;
N-((1-(3-cyano-1-methyl-2-oxo-1,2-dihydroquinolin-4-yl)azetidin-3-yl)methyl)acrylamide;
1-methyl-2-oxo-4-(3-(2-oxopyrrolidine-1-carbonyl)azetidin-1-yl)-1,2-dihydroquinoline-3-carbonitrile;
4-(3-(2-chloroacetyl)azetidin-1-yl)-1-(4-fluorobenzyl)-2-oxo-1,2-dihydroquinoline-3-carbonitrile;
(E)-4-(3-(2-chloroacetyl)azetidin-1-yl)-5-ethylidene-1-methyl-6-methylene-2-oxo-1,2,5,6-tetrahydropyridine-3-carbonitrile;
4-(3-acryloylcyclobutylamino)-1-methyl-2-oxo-1,2-dihydroquinoline-3-carbonitrile;
4-(3-acryloylcyclobutylamino)-1-(4-fluorobenzyl)-2-oxo-1,2-dihydroquinoline-3-carbonitrile;
4-(3-acryloylcyclobutylamino)-1-(2-(dimethylamino)ethyl)-2-oxo-1,2-dihydroquinoline-3-carbonitrile;
1-methyl-2-oxo-4-(3-propioloylcyclobutylamino)-1,2-dihydroquinoline-3-carbonitrile;
3-(3-cyano-1-methyl-2-oxo-1,2-dihydroquinolin-4-ylamino)-N-(cyanomethyl)cyclobutanecarboxamide;
1-methyl-2-oxo-4-(3-(2-(trifluoromethyl)acryloyl)cyclobutylamino)-1,2-dihydroquinoline-3-carbonitrile;
3-(3-cyano-1-methyl-2-oxo-1,2-dihydroquinolin-4-ylamino)-N-(4-vinylpyrimidin-2-yl)cyclobutanecarboxamide;
1-methyl-2-oxo-4-(3-(2-oxopyrrolidine-1-carbonyl)cyclobutylamino)-1,2-dihydroquinoline-3-carbonitrile;
4-(3-(2-chloroacetyl)cyclobutylamino)-1-methyl-2-oxo-1,2-dihydroquinoline-3-carbonitrile;
4-(3-(2-chloroacetyl)cyclobutylamino)-1-(4-fluorobenzyl)-2-oxo-1,2-dihydroquinoline-3-carbonitrile;
4-(3-acryloylcyclobutylamino)-1-benzyl-2-oxo-1,2-dihydroquinoline-3-carbonitrile;
4((3-acryloylcyclobutyl)(methyl)amino)-1-methyl-2-oxo-1,2-dihydroquinoline-3-carbonitrile;
4(1-(1-cyanocyclopropanecarbonyl)azetidin-3-yl)amino)-1-(4-fluorobenzyl)-2-oxo-1,2-dihydroquinoline-3-carbonitrile;
1-benzyl-4((1-(2-chloroacetyl)azetidin-3-yl)amino)-2-oxo-1,2-dihydroquinoline-3-carbonitrile;
4-((1-acryloylazetidin-3-yl)amino)-1-(3-fluorobenzyl)-2-oxo-1,2-dihydroquinoline-3-carbonitrile;
1-benzyl-2-oxo-4-((1-propioloylazetidin-3-yl)amino)-1,2-dihydroquinoline-3-carbonitrile;
4-((1-(2-chloroacetyl)azetidin-3-yl)amino)-7-fluoro-1-(3-fluorobenzyl)-2-oxo-1,2-dihydroquinoline-3-carbonitrile;
4-((1-(2-chloroacetyl)azetidin-3-yl)amino)-1-(4-fluorobenzyl)-2-oxo-1,2-dihydro-1,6-naphthyridine-3-carbonitrile;
4-((1-(2-chloroacetyl)azetidin-3-yl)amino)-1-(4-fluorobenzyl)-2-oxo-6-(trifluoromethyl)-1,2-dihydroquinoline-3-carbonitrile;
4-((1-acryloylazetidin-3-yl)amino)-6-fluoro-1-(4-fluorobenzyl)-2-oxo-1,2-dihydroquinoline-3-carbonitrile;
4-((1-(2-chloroacetyl)azetidin-3-yl)amino)-1-(2-morpholinoethyl)-2-oxo-1,2-dihydroquinoline-3-carbonitrile;
4-((1-(2-chloroacetyl)azetidin-3-yl)amino)-1-(4-chlorobenzyl)-2-oxo-1,2-dihydroquinoline-3-carbonitrile;
4-((1-(2-chloroacetyl)azetidin-3-yl)amino)-1-(4-methylbenzyl)-2-oxo-1,2-dihydroquinoline-3-carbonitrile;
4-((1-acryloylazetidin-3-yl)amino)-1-(4-fluorobenzyl)-2-oxo-1,2-dihydro-1,5-naphthyridine-3-carbonitrile;
1-(2-(dimethylamino)ethyl)-2-oxo-4-((1-propioloylazetidin-3-yl)amino)-1,2-dihydroquinoline-3-carbonitrile;
4-((1-(2-chloroacetyl)azetidin-3-yl)amino)-1-(2-ethoxyethyl)-7-fluoro-2-oxo-1,2-dihydroquinoline-3-carbonitrile;
4-((1-(2-chloroacetyl)azetidin-3-yl)amino)-1-(3-(dimethylamino)propyl)-6-fluoro-2-oxo-1,2-dihydroquinoline-3-carbonitrile;
4-((1-(oxirane-2-carbonyl)azetidin-3-yl)amino)-2-oxo-1-(2-propoxyethyl)-1,2-dihydroquinoline-3-carbonitrile;
4-((1-(1-cyanocyclopropanecarbonyl)azetidin-3-yl)amino)-1-(2-ethoxyethyl)-2-oxo-1,2-dihydroquinoline-3-carbonitrile;
4-((1-(2-chloroacetyl)azetidin-3-yl)amino)-1-(4-fluorobenzyl)-2-oxo-1,2-dihydro-1,8-naphthpidine-3-carbonitrile;
1-(4-fluorobenzyl)-4-4-((1-(oxirane-2-carbonyl)azetidin-3-yl)amino)-2-oxo-1,2-dihydroquinoline-3-carbonitrile
1-(4-fluorobenzyl)-4-((1-methacryloylazetidin-3-yl)amino)-2-oxo-1,2-dihydroquinoline-3-carbonitrile
4-((1-acryloylazetidin-3-yl)amino)-7-chloro-1-(4-fluorobenzyl)-2-oxo-1,2-dihydroquinoline-3-carbonitrile
4-((1-acryloylazetidin-3-yl)arnino)-1-(2-(dimethylamino)ethyl)-2-oxo-1,2-dihydroquinoline-3-carbonitrile
4-((1-(2-chloroacetyl)azetidin-3-yl)amino)-1-(2-(dimethylamino)ethyl)-7-fluoro-2-oxo-1,2-dihydroquinoline-3-carbonitrile
4-((1-(2-chloroacetyl)azetidin-3-yl)amino)-1-(3-(dimethylamino)propyl)-2-oxo-1,2-dihydroquinoline-3-carbonitrile
2-oxo-4-((1-propioloylazetidin-3-yl)amino)-1-(2-propoxyethyl)-1,2-dihydroquinoline-3-carbonitrile;
4-((1-(2-chloroacetyl)azetidin-3-yl)amino)-1-(2-ethoxyethyl)-7-fluoro-2-oxo-1,2-dihydroquinoline-3-carbonitrile;
1-(4-fluorobenzyl)-2-oxo-4-((1-(vinylsulfonyl)azetidin-3-yl)amino)-1,2-dihydroquinoline-3-carbonitrile;
4-((1-acryloylazetidin-3-yl)amino)-1-(4-fluorobenzyl)-2-oxo-1,2-dihydroquinoline-3-carbonitrile;
1-(4-fluorobenzyl)-2-oxo-4-((1-propioloylazetidin-3-yl)amino)-1,2-dihydroquinoline-3-carbonitrile;
4-((1-acryloylazetidin-3-yl)amino)-7-fluoro-1-(4-fluorobenzyl)-2-oxo-1,2-dihydroquinoline-3-carbonitrile;
4-((1-acryloylazetidin-3-yl)amino)-1-(4-fluorobenzyl)-2-oxo-1,2-dihydro-1,7-naphthyridine-3-carbonitrile;
4-((1-(2-chloroacetyl)azetidin-3-yl)amino)-1-(4-fluorobenzyl)-2-oxo-1,2-dihydro-1,6-naphthyridine-3-carbonitrile;
4((1-(2-chloroacetyl)azetidin-3-yl)amino)-1-(4-fluorobenzyl)-2-oxo-1,2-dihydro-1,7-naphthyridine-3-carbonitrile;
1-(4-fluorobenzyl)-2-oxo-4-((1-propioloylazetidin-3-yl)amino)-1,2-dihydro-1,6-naphthyridine-3-carbonitrile;
4-((1-(2-chloroacetyl)azetidin-3-yl)amino)-1-(2-ethoxyethyl)-2-oxo-1,2-dihydroquinoline-3-carbonitrile;

4-((1-(2-chloroacetyl)azetidin-3-yl)amino)-2-oxo-1-(2-propoxyethyl)-1,2-dihydroquinoline-3-carbonitrile;
5-((1-acryloylazetidin-3-yl)amino)-8-(4-fluorobenzyl)-2-methyl-7-oxo-7,8-dihydropyrido [2,3-d]pyrimidine-6-carbonitrile;
4-((1-acryloylazetidin-3-yl)amino)-1-(4-fluorobenzyl)-7-methyl-2-oxo-1,2-dihydro-1,6-naphthyridine-3-carbonitrile;
4-((1-acryloylazetidin-3-yl)amino)-1-(4-fluorobenzyl)-6-methyl-2-oxo-1,2-dihydro-1,7-naphthyridine-3-carbonitrile;
4-((1-acryloylazetidin-3-yl)amino)-6,7-difluoro-1-(4-fluorobenzyl)-2-oxo-1,2-dihydroquinoline-3-carbonitrile;
4-((1-acryloylazetidin-3-yl)amino)-1-(4-fluorobenzyl)-2-oxo-1,2-dihydroquinoline-3,7-dicarbonitrile;
4-((1-acryloylazetidin-3-yl)amino)-1-(4-fluorobenzyl)-2-oxo-1,2-dihydroquinoline-3,6-dicarbonitrile;
4-((1-acryloylazetidin-3-yl)amino)-1-(cyclopropylmethyl)-6-fluoro-2-oxo-1,2-dihydroquinoline-3-carbonitrile;
4-((1-acryloylazetidin-3-yl)amino)-7-chloro-1-(4-fluorobenzyl)-2-oxo-6-(trifluoromethyl)-1,2-dihydroquinoline-3-carbonitrile;
4-((1-acryloylazetidin-3-yl)amino)-1-(4-fluorobenzyl)-2-oxo-1,2-dihydroquinoline-3,7-dicarbonitrile;
1-(4-fluorobenzyl)-2-oxo-4-(4-(vinylsulfonyl)piperazin-1-yl)-1,2-dihydroquinoline-3-carbonitrile;
4-(4-acryloylpiperazin-1-yl)-7-fluoro-1-(4-fluorobenzyl)-2-oxo-1,2-dihydroquinoline-3-carbonitrile;
7-chloro-4-(4-(2-chloroacetyl)piperazin-1-yl)-1-(4-fluorobenzyl)-2-oxo-1,2-dihydroquinoline-3-carbonitrile;
4-(4-acryloylpiperazin-1-yl)-1-(2-ethoxyethyl)-2-oxo-1,2-dihydroquinoline-3-carbonitrile;
4-(4-acryloylpiperazin-1-yl)-2-oxo-1-(2-propoxyethyl)-1,2-dihydroquinoline-3-carbonitrile;
4-(4-acryloylpiperazin-1-yl)-1-(2-(dimethylamino)ethyl)-2-oxo-1,2-dihydroquinoline-3-carbonitrile;
1-benzyl-4-(4-(2-chloroacetyl)piperazin-1-yl)-2-oxo-1,2-dihydroquinoline-3-carbonitrile;
1-(2-ethoxyethyl)-2-oxo-4-(4-propioloylpiperazin-1-yl)-1,2-dihydroquinoline-3-carbonitrile;
4-(4-(2-chloroacetyl)piperazin-1-yl)-1-(4-fluorobenzyl)-2-oxo-1,2-dihydro-1,6-naphthyridine-3-carbonitrile;
1-(4-fluorobenzyl)-2-oxo-4-(4-(vinylsulfonyl)piperazin-1-yl)-1,2-dihydroquinoline-3-carbonitrile;
4-(4-acryloylpiperazin-1-yl)-7-fluoro-1-(4-fluorobenzyl)-2-oxo-1,2-dihydroquinoline-3-carbonitrile;
7-chloro-4-(4-(2-chloroacetyl)piperazin-1-yl)-1-(4-fluorobenzyl)-2-oxo-1,2-dihydroquinoline-3-carbonitrile;
4-(4-acryloylpiperazin-1-yl)-1-(2-ethoxyethyl)-2-oxo-1,2-dihydroquinoline-3-carbonittile;
4-(4-acryloylpiperazin-1-yl)-2-oxo-1-(2-propoxyethyl)-1,2-dihydroquinoline-3-carbonitrile;
4-(4-acryloylpiperazin-1-yl)-1-(2-(dimethylamino)ethyl)-2-oxo-1,2-dihydroquinoline-3-carbonitrile;
1-benzyl-4-(4-(2-chloroacetyl)piperazin-1-yl)-2-oxo-1,2-dihydroquinoline-3-carbonitrile;
1-(2-ethoxyethyl)-2-oxo-4-(4-propioloylpiperazin-1-yl)-1,2-dihydroquinoline-3-carbonitrile; and
4-(4-(2-chloroacetyl)piperazin-1-yl)-1-(4-fluorobenzyl)-2-oxo-1,2-dihydro-1,7-naphthyridine-3-carbonitrile.

13. The compound according to claim 1, wherein said compound is selected from the group consisting of:
4-((1-acryloylpiperidin-4-yl)amino)-1-methyl-2-oxo-1,2-dihydroquinoline-3-carbonitrile;
4-((1-acryloylazetidin-3-yl)amino)-1-(2-ethoxyethyl)-2-oxo-1,2-dihydroquinoline-3-carbonitrile;
4-((1-(2-chloroacetyl)azetidin-3-yl)amino)-1-(4-fluorobenzyl)-2-oxo-1,2-dihydroquinoline-3-carbonitrile; and
4-(4-acryloylpiperazin-1-yl)-1-(4-fluorobenzyl)-2-oxo-1,2-dihydroquinoline-3-carbonitrile.

14. A pharmaceutical formulation, comprising a pharmaceutically effective amount of a compound according claim 1 and a pharmaceutically acceptable carrier.

\* \* \* \* \*